(12) United States Patent
Sadar et al.

(10) Patent No.: US 9,862,667 B2
(45) Date of Patent: *Jan. 9, 2018

(54) DIGLYCIDIC ETHER DERIVATIVE THERAPEUTICS AND METHODS FOR THEIR USE

(75) Inventors: Marianne D. Sadar, West Vancouver (CA); Nasrin R. Mawji, Burnaby (CA); Jun Wang, New Westminster (CA); Raymond J. Andersen, Vancouver (CA); David E. Williams, Vancouver (CA); Mike Leblanc, Vancouver (CA)

(73) Assignees: THE UNIVERSITY OF BRITISH COLUMBIA, Vancouver (CA); BRITISH COLUMBIA CANCER AGENCY BRANCH, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/999,037

(22) PCT Filed: Jul. 2, 2009

(86) PCT No.: PCT/CA2009/000902
§ 371 (c)(1),
(2), (4) Date: May 31, 2011

(87) PCT Pub. No.: WO2010/000066
PCT Pub. Date: Jan. 7, 2010

(65) Prior Publication Data
US 2011/0230556 A1 Sep. 22, 2011

Related U.S. Application Data

(60) Provisional application No. 61/129,537, filed on Jul. 2, 2008.

(51) Int. Cl.
| | | |
|---|---|---|
| *A61K 31/225* | (2006.01) | |
| *A61K 31/075* | (2006.01) | |
| *C07C 39/367* | (2006.01) | |
| *A61K 31/09* | (2006.01) | |
| *C07C 43/23* | (2006.01) | |
| *C07C 229/12* | (2006.01) | |

(52) U.S. Cl.
CPC ............ *C07C 39/367* (2013.01); *A61K 31/09* (2013.01); *A61K 31/225* (2013.01); *C07C 43/23* (2013.01); *C07C 229/12* (2013.01); *C07B 2200/07* (2013.01)

(58) Field of Classification Search
USPC .................. 514/548, 721; 435/375; 568/609
See application file for complete search history.

(56) References Cited

U.S. PATENT DOCUMENTS

| | | |
|---|---|---|
| 2,571,217 A | 10/1951 | Davis et al. |
| 2,890,189 A | 6/1959 | Greenlee |
| 3,162,615 A | 12/1964 | Bremmer |
| 4,284,574 A | 8/1981 | Bagga |
| 4,369,298 A | 1/1983 | Kida et al. |
| 4,855,184 A | 8/1989 | Klun et al. |
| 4,904,760 A | 2/1990 | Gaku et al. |
| 5,043,375 A | 8/1991 | Henning et al. |
| 5,155,196 A | 10/1992 | Kolb et al. |
| 5,362,615 A | 11/1994 | Hagemann et al. |
| 5,403,697 A | 4/1995 | Doessel et al. |
| 5,753,730 A | 5/1998 | Nagata et al. |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

Bo-Ying Oncogene (2004) 23, 3350-3360.*

(Continued)

*Primary Examiner* — Shirley V Gembeh
(74) *Attorney, Agent, or Firm* — Cooley LLP

(57) ABSTRACT

This invention provides compound having a structure of Formula I or Formula II. Uses of such compounds for treatment of various indications, including prostate cancer as well as methods of treatment involving such compounds are also provided.

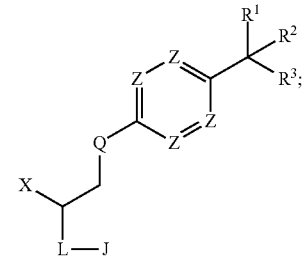

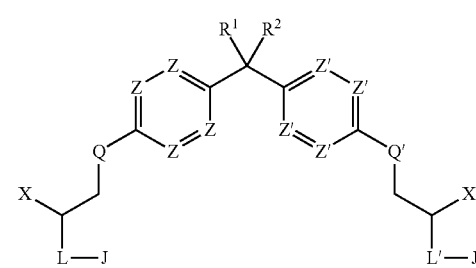

45 Claims, 10 Drawing Sheets

(56) References Cited

U.S. PATENT DOCUMENTS

| | | |
|---|---|---|
| 5,998,674 A | 12/1999 | Taketani et al. |
| 6,218,430 B1* | 4/2001 | Allegretto et al. ......... 514/475 |
| 6,245,117 B1 | 6/2001 | Nishikawa et al. |
| 7,183,323 B2 | 2/2007 | Chinn et al. |
| 7,595,345 B2 | 9/2009 | Bunel et al. |
| 7,674,795 B2 | 3/2010 | Mailliet et al. |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 2003/0092724 A1 | 5/2003 | Kao et al. |
| 2003/0105268 A1 | 6/2003 | Boriack et al. |
| 2004/0049004 A1 | 3/2004 | Boriack et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2016/0068466 A1 | 3/2016 | Andersen et al. |

FOREIGN PATENT DOCUMENTS

| | | |
|---|---|---|
| CA | 2 339 775 A1 | 3/2000 |
| CA | 2 606 262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EP | 0056175 A1 | 7/1982 |
| EP | 0 293 768 A1 | 12/1988 |
| EP | 0515128 A1 | 11/1992 |
| FR | 1389005 | 2/1965 |
| JP | B-S45-008432 | 3/1970 |
| JP | S56-5472 A | 1/1981 |
| JP | 63-196675 | 8/1988 |
| JP | H01-503541 | 11/1989 |
| JP | H02-4815 | 1/1990 |
| JP | 6-049473 A2 | 4/1994 |
| JP | 9-176240 A | 7/1997 |
| JP | H10133427 A | 5/1998 |
| JP | A-H10-316803 | 12/1998 |
| JP | 11-166087 A2 | 6/1999 |
| JP | 2000-072705 A2 | 3/2000 |
| JP | 2001-511170 A | 8/2001 |
| JP | 2005-325301 A | 11/2005 |
| JP | 2006-208607 A | 8/2006 |
| JP | 2006-265351 A2 | 10/2006 |
| JP | 2007-513089 A | 5/2007 |
| JP | 2007-290980 | 11/2007 |
| PL | 135932 | 9/1984 |
| PL | 141793 B1 | 8/1987 |
| WO | WO 88/09782 | 12/1988 |
| WO | WO 98/34930 A1 | 8/1998 |
| WO | WO 00/01813 A2 | 1/2000 |
| WO | WO 00/10958 A | 3/2000 |
| WO | WO 01/88013 A2 | 11/2001 |
| WO | WO 02/05813 A2 | 1/2002 |
| WO | WO 03/004481 A1 | 1/2003 |
| WO | WO 2005/042464 A1 | 5/2005 |
| WO | WO 2005/077967 A1 | 8/2005 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/179867 A1 | 11/2014 |
| WO | WO 2015/031984 A1 | 3/2015 |
| WO | WO 2016/058080 A1 | 4/2016 |
| WO | WO 2016/058082 A1 | 4/2016 |
| WO | WO 2016/112455 A1 | 7/2016 |
| WO | WO 2016/141458 A1 | 9/2016 |

OTHER PUBLICATIONS

Nakazawa et al. (Food and Chemical Toxicology 40(2002) 1827-1832).*

Patani et al. (isosteres in Medicinal Chemistr; Chem Rev. 1996, 3147-3176).*

Moreira-Lima (Current Medicinal Chemistry, 2005, 12, 23-49).*

Yong et al. , 200; 32(1):15-22.*

Satoh, et al. (2004) "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen" Food Chem. Toxicol. 42(6):983-993.

Schaffer A. et al, "Migration from can coatings: Part 3. Synthesis, identification and quantification of migrating epoxy-based substances below 1000 Da," Food Addit. Contam., 2004, 21 (4), pp. 390-405.

Fehlberg S. et al., "Bisphenol A diglycidyl ether induces apoptosis in tumor cells independently of peroxisome proliferator-activated receptor y, in caspase-dependent and -independent manners," Biochem. J., 2002, 362, pp. 573-578.

Taskeen, A. et al., "Analysis of bisphenol A in canned food: A mini review," Asian Journal of Chemistry, 22(5):4133-4135 (2010).

Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), The EFSA Journal, 86:1-40 (2004).

Wetherill, Y. B. et al., "In vitro molecular mechanisms of bisphenol A action," Reproductive Toxicology, 24:178-198 (2007).

Poustka, J. et al., "Determination and occurrence of bisphenol A, bisphenol A diglycidyl ether, and bisphenol F diglycidyl ether, including their derivatives, in canned foodstuffs from the Czech retail market," Czech J. Food Sci., 25(4):221-229 (2006).

Gallart-Ayala, H. et al., "The analysis of bisphenol A-diglycidyl ether (BADGE), bisphenol F-diglycidyl ether (BFDGE) and their derivatives in canned food and beverages by LC-MS/MS," Thermo Fisher Scientific Inc., (2011), 4 pages.

Myung, J-K et al., "An androgen receptor N-terminal domain antagonist for treating prostate cancer," The Journal of Clinical Investigation, 123(7):2948-2960 (2013).

Auzou et al., *European Journal of Medicinal Chemistry*, 9(5):548-554 (1974) (with English Abstract).

Balbay, M.D. et al., "Highly Metastatic Human Prostate Cancer Growing within the Prostate of Athymic Mice Overexpresses Vascular Endothelial Growth Factor", *Clinical Cancer Research*, 5:783-789 (1999).

Berge, S.M. et al., "Pharmaceutical Salts", *Pharmaceutical Sciences*, 66(1):1-19 (1977).

Berger, U. et al. , "Identification of Derivatives of Bisphenol A Diglycidyl Ether and Novolac Glycidyl Ether in Can Coatings by Liquid Chromatography/Ion Trap Mass Spectrometry," Journal of AOAC International, *Food Chemical Contaminants*, 83(6):1367-1376 (2000).

Biles, J.E. et al., "Determination of the Diglycidyl Ether of Bisphenol A and its Derivatives in Canned Foods", *J. Agric. Food Chem.*, 47:1965-1969 (1999).

Bisson, W.H. et al., "Discovery of antiandrogen activity of nonsteroidal scaffolds of marketed drugs", *PNAS*, 104(29):11927-11932 (2007).

(56) References Cited

OTHER PUBLICATIONS

Blaszczyk, N. et al., "Osteoblast-Derived factors Induce Androgen-Independent Proliferation and Expression of Prostate-Specific Antigen in Human Prostate Cancer Cells", *Clin. Cancer Res.*, 10:1860-1869 (2004).
Bohler, Paul et al., "Identification of Migrants from Coatings of Food Cans and Tubes: Reaction Products of Bisphenol-A-Diglycidyl Ether (BADGE) with Phenols and Solvents", *Mitt. Gebiete Lebensm. Hyg.*, 89:529-547 (1998).
Bruckheimer, E.M. et al., "Apoptosis in prostate carcinogenesis A growth regulator and a therapeutic target", *Cell Tissue Res*, 301:153-162 (2000).
Chang, C. et al., "Development of Peptide Antagonists for the Androgen Receptor Using Combinatorial Peptide Phage Display", *Molecular Endocrinology*, 19(10):2478-2490 (2005).
Clinton, G.M. et al., "Estrogen action in human ovarian cancer", *Critical Reviews in Oncology/Hematology*, 25:1-9 (1997).
Culig, Zoran et al., "Androgen Receptor Activation in Prostatic Tumor Cell Lines by Insulin-like Growth Factor-I, Keratinocyte Growth Factor, and Epidermal Growth Factor", *Cancer Research*, 54:5474-5478 (1994).
Das, Debasish et al., "Sulfonic acid functionalized mesoporous MCM-41 silica as a convenient catalyst for Bisphenol-A synthesis", *Chemical Communications*, pp. 2178-2179 (2001).
Dehm, S. et al., "Ligand-independent Androgen Receptor Activity is Activation Function-2-independent and Resistant to Antiandrogens in Androgen Refractory Prostate Cancer Cells", *The Journal of Biological Chemistry*, 281(38):27882-27893 (2006).
Dehm, S. et al., "Splicing of a Novel Androgen Receptor Exon Generates a Constitutively Active Androgen Receptor that Mediates Prostate Cancer Therapy Resistance", *Cancer Research*, 68:5469-5477 (2008).
Edmondson, J. M. et al., "The human ovarian surface epithelium is an androgen responsive tissue", *British Journal of Cancer*, 86:879-885 (2002).
Estebanez-Perpiñá, E. et al., "A surface on the androgen receptor that allosterically regulates coactivator binding," *PNAS*, 104 (41):16074-16079 (2007).
Estebanez-Perpiñá, E. et al., "The Molecular Mechanisms of Coactivator Utilization in Ligand-dependent Transactivation by the Androgen Receptor," *The Journal of Biological Chemistry*, 280(9):8060-8068 (2005).
Gleave, Martin et al., "Acceleration of Human Prostate Cancer Growth in Vivo by Factors Produced by Prostate and Bone Fibroblasts", *Cancer Research*, 51:3753-3761 (1991).
Gregory, Christopher et al., "Epidermal Growth Factor Increases Coactivation of the Androgen Receptor in Recurrent Prostate Cancer", *The Journal of Biological Chemistry*, 279(8):7119-7130 (2004).
Guinan, P.D. et al., "Impotence Therapy and Cancer of the Prostate", *The American Journal of Surgery*, 131:599-600 (1976).
Haggstrom, Stina et al., "Testosterone Induces Vascular Endothelial Growth Factor Synthesis in the Ventral Prostate in Castrated Rats", *The Journal of Urology*, 161:1620-1625 (1999).
Harper et al., "Expression of Androgen Receptor and Growth Factors in Premalignant Lesions of the Prostate", *Journal of Pathology*, 186:169-177 (1998).
He, B. et al., "Activation Function 2 in the Human Androgen Receptor Ligand Binding Domain Mediates Interdomain Communication with the $NH_2$-terminal Domain", *The Journal of Biological Chemistry*, 274(52):37219-37225 (1999).
He, B. et al., "Structural Basis for Androgen Receptor Interdomain and Coactivator Interactions Suggests a Transition in Nuclear Receptor Activation Function Dominance", *Molecular Cell*, 16:425-438, 2004.
Heinlein, Cynthia A., et al., "Androgen Receptor in Prostate Cancer", *Endocrine Reviews*, 25(2):276-308 (2004).
Helzlsouer, Kathy J., et al., "Serum Gonadotropins and Steroid Hormones and the Development of Ovarian Cancer", *JAMA*, 274(24):1926-1930 (1995).

Horoszewicz, J.S. et al., "LNCaP Model of Human Prostatic Carcinoma", *Cancer Research*, 43:1809-1818 (1983).
Huber, P.R. et al., "Prostate Specific Antigen. Experimental and Clinical Observations", *Scand. J. Urol Nephrol.*, 104:33-39 (1987).
Hur, E. et al., "Recognition and Accommodation at the Androgen Receptor Coactivator Binding Interface", *PLoS Biology*, 2(9): 1303-1312 (2004).
Isaacs, J.T., et al., "New Biochemical Methods to Determine Androgen Sensitivity of Prostatic Cancer: The Relative Enzymatic Index (REI)", *Prostate Cancer and Hormone Receptors*, pp. 133-144 (1979).
Isaacs, J.T., "Antagonistic Effect of Androgen on Prostatic Cell Death", *The Prostate*, 5:545-557 (1984).
Jackson, J. A. et al., "Prostatic Complications of Testosterone Replacement Therapy", *Arch Intern Med.*, 149:2365-2366 (1989).
Jenster, G. et al., "Domains of the Human Androgen Receptor Involved in Steroid Binding, Transcriptional Activation, and Subcellular Localization", *Molecular Endocrinology*, 5:1396-1404 (1991).
Jia, L. et al., "Androgen Receptor Signaling: Mechanism of Interleukin-6 Inhibition", *Cancer Research*, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", *Cancer Research*, 65:8003-8008 (2005).
Kaighn, M.E. et al., "Prostate Carcinoma: Tissue Culture Cell Lines", *National Cancer Institute Monograph* No. 49, pp. 17-21 (1978).
Kemppainen, J. A. et al., "Distinguishing Androgen Receptor Agonists and Antagonists: Distinct Mechanisms of Activation by Medroxyprogesterone Acetate and Dihydrotestosterone", *Mol. Endocrinol.*, 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", *American Journal of Pathology*, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", *J. Am. Chem. Soc.*, 123:6809-6818 (2001).
Kumar, S. et al., "Synthesis of new crown analogs derived from bisphenol," *Indian Journal Chemistry*, 36B:656-661 (1997).
Langley, E. et al., "Evidence for an Anti-parallel Orientation of the Ligand-activated Human Androgen Receptor Dimer", *The Journal of Biological Chemistry*, 270(50):29983-29990 (1995).
Lannoye, G.S. et al., "N-Fluoroalkylated and N-alkylated analogs of the dopaminergic D-2 receptor antagonist raclopride", *J. Med. Chem.*, 33(9):2430-2437 (1990).
Loren, J.C. et al., "Synthesis of achiral and racemic catenanes based on terpyridine and a directionalized terpyridine mimic, pyridyl-phenanthroline", *Org. Biomol. Chem.*, 3(17):3105-3116 (2005).
Louie, M.C. et al., "Androgen-induced recruitment of RNA polymerase II to a nuclear receptor—p160 coactivator complex", *PNAS*, 100(5)2226-2230 (2003).
Martin, S.J. et al., "A new precursor for the radiosynthesis of [$^{18}$F]FLT", *Nuclear Medicine and Biology*, 29:263-273 (2002).
Masiello, D. et al., "Bicalutamide Functions as an Androgen Receptor Antagonist by Assembly of a Transcriptionally Inactive Receptor", *The Journal of Biological Chemistry*, 277(29):26321-26326 (2002).
Melnyk, O. et al., "Neutralizing Ant-Vascular Endothelial Growth Factor Antibody Inhibits Further Growth of Established Prostate Cancer and Metastases in a Pre-Clinical Model", *The Journal of Urology*, 161:960-963 (1999).
Miller, J.I. et al., "The Clinical Usefulness of Serum Prostate Specific Antigen After Hormonal Therapy of Metastatic Prostate Cancer", *The Journal of Urology*, 147:956-961 (1992).
Mitsiades, C.S. et al., "Molecular biology and cellular physiology of refractoriness to androgen ablation therapy in advanced prostate cancer", *Expert Opin. Investig. Drugs*, 10(6):1099-1115 (2001).
Nakazawa, H. et al., "In vitro assay of hydrolysis and chlorohydroxy derivatives of bisphenol A diglycidyl ether for estrogenic activity", *Food and Chemical Toxicology*, 40:1827-1832 (2002).

(56) References Cited

OTHER PUBLICATIONS

Nazareth, L.V. et al, "Activation of the Human Androgen Receptor through a Protein Kinase A Signaling Pathway", *The Journal of Biological Chemistry*, 271(33):19900-19907 (1996).
Noble, R. L., "The development of prostatic adenocarcinoma in Nb Rats following prolonged sex hormone administration", *Cancer Research*, 37:1929-1933 (1977).
Noble, R. L., "Sex steroids as a cause of adenocarcinoma of the dorsal prostate in Nb Rats, and their influence on the growth of transplants", *Oncology*, 34:138-141 (1977).
Ogawa, Y. et al., "Estrogenic activities of chemicals related to food contact plastics and rubbers tested by the yeast two-hybrid assay," *Food Additives and Contaminants*, 23:4, 422-430 (2006).
Paris, F. et al., "Phenylphenols, biphenols, bisphenol-A and 4-tert-octyphenol exhibit α and β estrogen activities and antiandrogen activity in reporter cell lines," *Molecular and Cellular Endocrinology*, 193:43-49 (2002).
Quayle, S. et al., "Androgen receptor decoy molecules block the growth of prostate cancer", *PNAS*, 104(4):1331-1336 (2007).
Rao, B.R. et al., "Endocrine Factors in Common Epithelial Ovarian Cancer", *Endocrine Reviews*, 12(1):14-26 (1991).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", *Journal of the National Cancer Institute*, 90(23):1774-1786 (1998).
Roberts, J. T. et al., "Adenocarcinoma of Prostate in 40-Year-Old Body-Builder", *Lancet*, 2:742 (1986).
Rokicki, G. et al., "Reactions of 4-chloromethyl-1,3-dioxolan-2-one with phenols as a new route to polyols and cyclic carbonates", *Journal f. prakt. Chemie.*, 327:718-722 (1985).
Ross, R.K. et al., "Androgen Metabolism and Prostate Cancer: Establishing a Model of Genetic Susceptibility", *European Urology*, 35:355-361 (1999).
Sadar, M., "Androgen-independent Induction of Prostate-specific Antigen Gene Expression via Cross-talk between the Androgen Receptor and Protein Kinase A signal Transduction Pathways," *The Journal of Biological Chemistry*, 274(12):7777-7783 (1999).
Sadar, M. et al., "Prostate cancer: molecular biology of early progression to androgen independence", *Endocrine-Related Cancer*, 6:487-502 (1999).
Sadar, M.D. et al., "Characterization of a New in Vivo Hollow Fiber Model for the Study of Progression of Prostate Cancer to Androgen Independence", *Molecular Cancer Therapeutics*, 1:629-637 (2002).
Sato, N. et al., "Intermittent Androgen Suppression Delays Progression to Androgen-independent Regulation of Prostate-specific Antigen Gene in the LNCaP Prostate Tumour Model", *J. Steroid Biochem. Mol. Biol.*, 58:139-146 (1996).
Sato, N. et al., "A Metastatic and Androgen-sensitive Human Prostate Cancer Model Using Intraprostatic Inoculation of LNCaP Cells in SCID Mice", *Cancer Research*, 57:1584-1589 (1997).
Snoek, R. et al., "Induction of Cell-free, In Vitro Transcription by Recombinant Androgen Receptor Peptides", *J. Steroid Biochem. Mol. Biol.*, 59:243-250 (1996).
Still, W. C. et al., "Rapid Chromatographic Technique for Preparative Separations with Moderate Resolution", *J. Org. Chem.*, 43(14):2923-2925 (1978).
Tanji, N. et al., "Growth Factors: Rules in Andrology", *Archives of Andrology*, 47:1-7 (2001).
Taplin, M.E. et al., "Selection for Androgen Receptor Mutations in Prostate cancers Treated with Androgen Antagonist", *Cancer Research*, 59:2511-2515 (1999).
Thomson, A.A., "Role of androgens and fibroblast growth factors in prostatic development", *Reproduction*, 121:187-195 (2001).
Ueda, T. et al., "Activation of the Androgen Receptor N-terminal Domain by Interleukin-6 via MAPK and STAT3 Signal Transduction Pathways", *The Journal of Biological Chemistry*, 277(9):7076-7085 (2002).

Ueda, T. et al., "Ligand-independent Activation of the Androgen Receptor by Interleukin-6 and the Role of Steroid Receptor Coactivator-1 in Prostate cancer Cells", *The Journal of Biological Chemistry*, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese marker", *Food Additives and Contaminants*, 18(2):177-185 (2001).
Van Der Kwast, T.H. et al., "Androgen Receptors in Endocrine-Therapy-Resistant Human Prostate Cancer", *Inter. J. Cancer*, 48:189-193 (1991).
Wang, G. et al., "Identification of genes targeted by the androgen and PKA signaling pathways in prostate cancer cells", *Oncogene*, 25:7311-7323 (2006).
Wang, Q. et al., "Spatial and Temporal Recruitment of Androgen Receptor and Its Coactivators Involves Chromosomal Looping and Polymerase Tracking", *Molecular Cell*, 19:631-642 (2005).
Wilding, G., "The Importance of Steroid Hormones in Prostate Cancer", *Cancer Surveys*, 14:113-130 (1992).
Wilson, J.D. et al., "Long-Term Consequences of Castration in Men: Lessons from the Skoptzy and the Eunuchs of the Chinese and Ottoman Courts", *The Journal of Clinical Endocrinology & Metabolism*, 84:4324-4331 (1999).
Wong, C. et al., "Steroid Requirement for Androgen Receptor Dimerization and DNA Binding", *J. Biol. Chem.*, 268(25):19004-19012 (1993).
Xu, X. et al, "Synthesis and Stability Study of Dental Monomers Containing Methacrylamidoethyl Phosphonic Acids", *Journal of Polymer Science: Part A Polymer Chemistry*, 45:99-110 (2007).
Ye, Deyong, "An Introduction to Computer-Aided Drug Design", 3 pages, Jan. 31, 2004.
Brzozowski, Z. et al., "Precursors for bisphenolic resins," CAPLUS Database Accession No. 1990:36690, Document No. 112:33690, (1987), 1 page (Abstract).
Choi, K. M. et al., "New families of photocurable oligomeric fluoromonomers for use in dental composites," Chemistry of Materials, 8(12):2704-2707 (1996).
Crivello, J. V. et al., "Synthesis and photopolymerization of multifunctional propenyl ether monomers," Database CAPLUS [online], Chemical Abstracts Service, Columbus, Ohio, XP002729292, retrieved from STN CA Caesar Accession No. 1994-606067 (1994), 3 pages.
Crivello, J. V. et al., "Synthesis and photopolymerization of multifunctional propenyl ether monomers," Journal of Macromolecular Science, Pure and Applied Chemistry, A31(9):1105-1119 (1994).
Cook, W. D., "Fracture and structure of highly crosslinked polymer composites," Journal of Applied Polymer Science, 42:1259-1269 (1991).
Nedolya, N. A. et al., Zhurnal Organicheskoi Khimii, 30(8):1163-1166 (1994).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-2777 (1995).
Reader, C. E. L., "Epoxy resin derivatives for stoving systems," Surface Coatings Australia, 25(10):6-9 (1988).
Rusu, E. et al.: "Photosensitive compounds with chloromethyl groups," Revue Roumaine de Chimie, 45(5):451-456 (2000).
Silverman, R. B., The Organic Chemistry of Drug Design and Drug Action, pp. 15-20 (1992).
Decision of Refusal for Japanese Application No. 2011-515039, mailed Dec. 2, 2014, 18 pages.
Anderson, R. et al., "Regression of Castrate-Recurrent Prostate Cancer by a Small-Molecule Inhibitor of the Amino-Terminus Domain of the Androgen Receptor", *Cancer Cell*, 17:535-546 (2010).
Danquah, M. et al., "Micellar Delivery of Bicalutamide and Embelin for Treating Prostate Cancer", *Pharmaceutical Research*, 26:2081-2092 (2009).

(56) References Cited

OTHER PUBLICATIONS

Garuti, L., et al., "Irreversible Protein Kinase Inhibitors", *Current Medicinal Chemistry*, 18:2981-2994 (2011).
Guo, Zhiyong et al., "A Novel Androgen Receptor Splice Variant is Up-regulated during Prostate Cancer Progression and Promotes Androgen Depletion—Resistant Growth", *Cancer Research*, 69:2305-13 (2009).
Hu, R. et al., "Ligand-Independent Androgen Receptor Variants Derived from Splicing of Cryptic Exons Signify Hormone-Refractory Prostate Cancer", *Cancer Research*, 69:16-22 (2009).
L'Heureux, A. et al., "Aminodifluorosulfinium Salts: Selective Fluorination Reagents with Enhanced Thermal Stability and Ease of Handling", *J. Org. Chem*, 75:3401-3411 (2010).
Rao and Slotman, "Endocrine factors in common epithelial ovarian cancer", *Endocrine Reviews*, 12(1):14-26 (1991).
Sun, S. et al., "Castration resistance in human prostate cancer is conferred by a frequently occurring androgen receptor splice variant", *The Journal of Clinical Investigation*, 120(8):2715-30 (2010).
Van Scherpenzeel, M. et al., "Nanomolar affinity, iminosugar-based chemical probes for specific labeling of lysosomal glucocerebrosidase", *Bioorganic & Medicinal Chemistry*, 18:267-273 (2010).
Zuhayra, M. et al., "New approach for the synthesis of [$^{18}$F]fluoroethyltyrosine for cancer imaging: Simple, fast, and high yielding automated synthesis", *Bioorganic & Medicinal Chemistry*, 17:7441-7448 (2009).
Supplementary European Search Report in EP Application No. 09771876.1 dated Jun. 20, 2011, 5 pages.
Supplementary European Search Report in EP Application No. 11731645.5 dated mailed Jun. 2, 2013, 11 pages.
International Preliminary Report on Patentability for PCT/CA2009/000902 issued Jan. 5, 2011, 7 pages.
International Search Report for PCT/CA2009/000902 mailed Sep. 1, 2009, 4 pages.
Written Opinion for PCT/CA2009/000902 mailed Sep. 1, 2009, 6 pages.
International Preliminary Report on Patentability for PCT/US2012/032584 issued Oct. 8, 2013, 6 pages.
International Search Report for PCT/US2012/032584 mailed Jul. 31, 2012, 3 pages.
Written Opinion for PCT/US2012/032584 mailed Jul. 31, 2012, 5 pages.
International Preliminary Report on Patentability for PCT/US2012/033959 dated Oct. 22, 2013, 8 pages.
International Search Report for PCT/US2012/033959 mailed Jul. 18, 2012, 3 pages.
Written Opinion for PCT/US2012/033959 mailed Jul. 18, 2012, 7 pages.
International Preliminary Report on Patentability for PCT/US2012/033957 dated Oct. 22, 2013, 6 pages.
International Search Report for PCT/US2012/033957 mailed Jul. 18, 2012, 3 pages.
Written Opinion for PCT/US2012/033957 mailed Jul. 18, 2012, 5 pages.
International Preliminary Report on Patentability for PCT/CA2011/000019 dated Jul. 10, 2012, 8 pages.
International Search Report for PCT/CA2011/000019 mailed Mar. 21, 2011, 7 pages.
Written Opinion for PCT/CA2011/000019 mailed Mar. 21, 2011, 7 pages.
International Preliminary Report on Patentability for PCT/CA2011/000021 dated Jul. 10, 2012, 8 pages.
International Search Report for PCT/CA2011/000021 mailed Apr. 11, 2011, 8 pages.
Written Opinion for PCT/CA2011/000021 mailed Apr. 11, 2011, 7 pages.
International Preliminary Report on Patentability for PCT/US2012/051481 dated Feb. 25, 2014, 8 pages.
International Search Report for PCT/US2012/051481 mailed Nov. 26, 2012, 4 pages.
Written Opinion for PCT/US2012/051481 mailed Nov. 26, 2012, 7 pages.
International Preliminary Report on Patentability for PCT/US2012/051923 dated Feb. 25, 2014, 9 pages.
International Search Report for PCT/US2012/051923 mailed Jan. 28, 2013, 4 pages.
Written Opinion for PCT/US2012/051923 mailed Jan. 28, 2013, 8 pages.
Extended European Search Report in Application No. EP 12768410.8 dated Sep. 22, 2014, 10 pages.
International Search Report and Written Opinion for PCT/CA2014/000414 mailed Dec. 4, 2014, 6 pages.
International Search Report and Written Opinion for PCT/CA2014/000685 mailed Dec. 4, 2014, 13 pages.
Patani and LaVoie, "Bioisosterism: A Rational Approach in Drug Design", *Chem. Rev.*, 96: 3147-3176 (1996).
Strub and McKim, "Dimethyl Sulfoxide USP, PhEur in Approved Pharmaceutical Products and Medical Devices", PharmaTech.com, 6 pages (2008). http://www. pharmtech.com/print/224268?page=full&rel=canonical.
Alvarez, C. et al., "Confirmational and Experimental Studies on the Dipole Moments of Models of Comblike Polymers", *Macromolecules*, 30(20): 6369-6375 (1997).
Henke, H., "Selektive präparative gelchromatographische Trennung niedermolekularer Verbindungen an Sephadex LH-20", Journal of Chromatography, 254: 296-308 (1983).
Riu, A. et al., "Characterization of Novel Ligands of ERα, Erβ, and PPARγ: The Case of Halogenated Bisphenol A and Their Conjugated Metabolites", *Toxicology Sciences*, 122(2): 372-382 (2011).
Wilcox and Cowart, "New Approaches to Synthetic Receptors. Synthesis and Host Properties of a Water Soluble Macrocyclic Analog of Troger's Base", *Tetrahedron Letters*, 27(46): 5563-5566 (1986).
International Preliminary Report on Patentability for PCT/CA2014/000414 mailed Nov. 10, 2015, 7 pages.
International Preliminary Report on Patentability for PCT/CA2014/000685 dated Mar. 15, 2016, 7 pages.
International Search Report and Written Opinion for PCT/CA2016/000008 dated Mar. 15, 2016, 13 pages.
International Search Report and Written Opinion for PCT/CA2015/000533 dated Dec. 18, 2015, 11 pages.
International Search Report and Written Opinion for PCT/CA2015/000535 dated Dec. 23, 2015, 9 pages.
Garcia et al., "Determination of compounds from epoxy resins in food simulants by HPLC-fluorescence." *Chromatographia*, 58(5-6): 337-342 (2003).
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages. (Abstract).
Schellhammer, "An evaluation of bicalutamide in the treatment of prostate cancer." *Expert Opinion on Pharmacotherapy*, 3(9): 1313-1328 (2002).
International Search Report and Written Opinion for PCT/CA2016/000070 dated Jun. 2, 2016, 10 pages.
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." *Journal of Chromatography A* (2005); 1073.1: 331-339.
Petersen, H. et al., "Determination of bisphenol A diglycidyl ether (BADGE) and its derivatives in food: identification and quantification by internal Standard", *Eur. Food Res. Technol.*, 216:355-364 (2003).
Poouthree, K. et al., "Comparison of resolution in microemulsion EKC and MEKC employing suppressed electroosmosis: Application to bisphenol-A-diglycidyl ether and its derivatives", *Electrophoresis*, 28(20):3705-3711 (2007).
Poustková et al., "Stability of bisphenol A diglycidyl ether and bisphenol F diglycidyl ether in water-based food simulants." *European Food Research and Technology*, 219(5): 534-539 (2004).
Extended European Search Report in Application No. EP 14793978.9 dated Sep. 1, 2016, 8 pages.

(56) References Cited

OTHER PUBLICATIONS

Japanese Patent Application No. 2016-512175, Notice of Reasons for Rejection dated Jun. 21, 2016 (and English translation), 12 pages.

* cited by examiner

DIGLYCIDIC ETHER DERIVATIVE THERAPEUTICS AND METHODS FOR THEIR USE

CROSS REFERENCE TO RELATED APPLICATIONS

This application is a 371 national stage application of International Application No. PCT/CA2009/000902, filed on Jul. 2, 2009, which claims the benefit of U.S. Provisional Patent Application Ser. No. 61/129,537 entitled "SMALL MOLECULE THERAPEUTICS AND METHODS FOR THEIR USE" filed on Jul. 2, 2008, the disclosure of which are incorporated herein by reference in their entireties.

STATEMENT REGARDING FEDERALLY SPONSORED RESEARCH

This invention was made in part with government support under grant number W81XWH-05-1-0058 (PC040768), awarded by U.S. Army Medical Research and Materiel Command. The government has certain rights in the invention.

TECHNICAL FIELD

This invention relates to therapeutics, their uses and methods for the treatment of various indications, including various cancers. In particular the invention relates to therapies and methods of treatment for cancers such as prostate cancer, including all stages and androgen dependent, androgen-sensitive and androgen-independent (also referred to as hormone refractory, castration resistant, androgen deprivation resistant, androgen ablation resistant, androgen depletion-independent, castration-recurrent, anti-androgen-recurrent).

BACKGROUND

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of androgens (androgen-independent disease) (Huber et al 1987 *Scand J. Urol Nephrol.* 104, 33-39). Androgen-independent disease is biochemically characterized before the onset of symptoms by a rising titre of serum PSA (Miller et al 1992 *J. Urol.* 147, 956-961). Once the disease becomes androgen-independent most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR may be activated in the absence of testicular androgens by alternative signal transduction pathways in androgen-independent disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, and flutamide and the steroidal antiandrogen, cyproterone acetate. These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)). These antiandrogens would also have no effect on the recently discovered AR splice variants that lack the ligand-binding domain (LBD) to result in a constitutively active receptor which promotes progression of androgen-independent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009).

Conventional therapy has concentrated on androgen-dependent activation of the AR through its C-terminal domain. Recent studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinisic disorder in solution (Reid et al 2002 *J. Biol. Chem.* 277, 20079-20086) thereby hampering virtual docking drug discovery approaches.

SUMMARY

This invention is based in part on the fortuitous discovery that compounds described herein modulate androgen receptor (AR) activity. Specifically, compounds identified herein, show inhibition of AR N-Terminal Domain (NTD) transactivation, which may be useful for blocking in vivo tumor growth in the presence and absence of androgens. The discovery was particularly fortuitous because the initial screen of marine invertebrate extracts was testing for inhibition of AR NTD transactivation by at least 50% and some of the compounds identified in that initial screen were determined to have a structural resemblance to BADGE (Bisphenol A Diglycidic Ether). The resemblance to BADGE suggests that these compounds are most likely of industrial origin and were bioaccumulated by the sponge from the contaminated seawater. Accordingly, due to the known activities for Badge compounds, the present BADGE derivatives are very unlikely to have been screened in the assay under any other circumstances.

The compounds described herein may be used for in vivo or in vitro research uses (i.e. non-clinical) to investigate the mechanisms of orphan and nuclear receptors (including steroid receptors such as the androgen receptor). Furthermore, these compounds may be used individually or as part of a kit for in vivo or in vitro research to investigate signal transduction pathways and/or the activation of orphan and nuclear receptors using recombinant proteins, cells maintained in culture, and/or animal models.

This invention is also based in part on the surprising discovery that the compounds described herein, may also be used to modulate the androgen receptor activity either in vivo or in vitro for both research and therapeutic uses. The compounds may be used in an effective amount so that androgen receptor activity may be modulated. The androgen receptor may be mammalian. Alternatively, the androgen receptor may be human. In particular, the compounds may be used to inhibit transactivation of the AR N-terminal domain (NTD). The compounds modulatory activity may be used in either an in vivo or an in vitro model for the study of at least one of the following indications: prostate cancer, breast cancer, ovarian cancer, endometrial cancer, hair loss, acne, hirsutism, ovarian cysts, polycystic ovary disease, precocious puberty, and age-related macular degeneration. Furthermore, the compounds modulatory activity may be used for the treatment of at least one of the following indications: prostate cancer, breast cancer, ovarian cancer, endometrial cancer, hair loss, acne, hirsutism, ovarian cysts, polycystic ovary disease, precocious puberty (testoxicosis) and age-related macular degeneration. The indication for treatment may be prostate cancer. The prostate cancer may be androgen-independent prostate cancer. The prostate cancer may be androgen-dependent prostate cancer.

In accordance with one embodiment, there is provided a use of a compound having a structure of Formula I

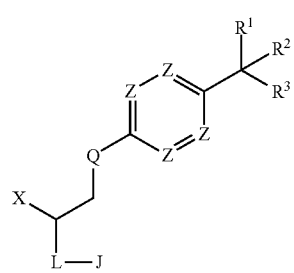

wherein, J may be H or a moiety may be selected from TABLE 1; L may be O, S, NH, NG, N$^+$H$_2$, or N$^+$HG; X may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', G, CH$_2$OG, CH$_2$OGOG', GOG', GOG'OG'', CH$_2$SG, CH$_2$NH$_2$, CH$_2$NHG, or CH$_2$NG$_2$; Q may be G, O, CH$_2$, CHG, CG$_2$, S, NH or NG; each Z may independently be N, CH, CF, CCl, CBr, CI, COH, CG, COG, CNH$_2$, CNHG, CNG$_2$, COSO$_3$H, COPO$_3$H$_2$; CSG, CSOG, or CSO$_2$G; R$^1$ and R$^2$ may each independently be H, or a branched or unbranched, substituted or unsubstituted C$_1$-C$_{10}$ alkyl or together form a substituted or unsubstituted, saturated, aromatic cyclic or non-aromatic cyclic C$_3$-C$_{10}$ alkyl; each G G' and G'' may independently be a branched, unbranched, or aromatic cyclic or non-aromatic cyclic, substituted or unsubstituted, saturated or unsaturated C$_1$-C$_{10}$ alkyl; R$^3$ may be H, a branched, unbranched, substituted or unsubstituted C$_1$-C$_{10}$ alkyl, or

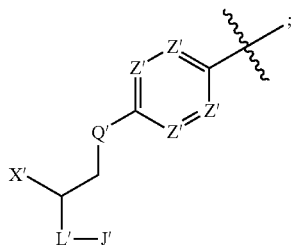

J' may be H or a moiety selected from TABLE 1; L' may be O, S, NH, NG, N$^+$H$_2$, or N$^+$HG; each Z' may independently be N, CH, CF, CCl, CBr, CI, COH, CG, COG, CNH$_2$, CNHG, CNG$_2$, COSO$_3$H, COPO$_3$H$_2$; CSG, CSOG, or CSO$_2$G; Q' may be G, O, CH$_2$, CHG, CG$_2$, S, NH or NG; X' may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', G, CH$_2$OG, CH$_2$OGOG', GOG', GOG'OG'', CH$_2$SG, CH$_2$NH$_2$, CH$_2$NHG, CH$_2$NG$_2$, or

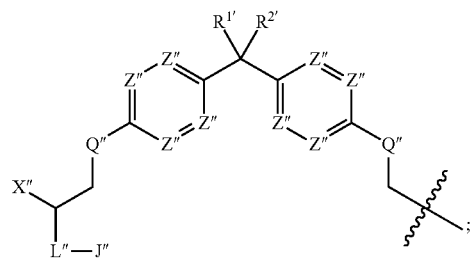

R$^{1'}$ and R$^{2'}$ may each independently be H, or a branched, unbranched, substituted or unsubstituted C$_1$-C$_{10}$ alkyl or together form a substituted or unsubstituted, saturated, aromatic cyclic or non-aromatic cyclic C$_3$-C$_{10}$ alkyl; each J'' and J''' may independently be H or a moiety selected from TABLE 1; L'' may be O, S, NH, NG, N$^+$H$_2$, or N$^+$HG; each Z'' may independently be N, CH, CF, CCl, CBr, CI, COH, CG, COG, CNH$_2$, CNHG, CNG$_2$, COSO$_3$H, COPO$_3$H$_2$; CSG, CSOG, or CSO$_2$G; Q'' may be G, O, CH$_2$, CHG, CG$_2$, S, NH or NG; and X'' may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', G, CH$_2$OG, CH$_2$OGOG', GOG', GOG'OG'', CH$_2$SG, CH$_2$NH$_2$, CH$_2$NHG, or CH$_2$NG$_2$; wherein an optional substituent if present may be selected from the group consisting of: oxo (i.e. =O), OJ''', COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$ wherein R may be an unsubstituted C$_1$-C$_{10}$ alkyl; for modulating androgen receptor (AR) activity. Alternatively, the use may be for the preparation of a medicament for modulating androgen receptor (AR).

In accordance with another embodiment, there is provided a pharmaceutical composition comprising a compound having a structure of Formula I set out above and a pharmaceutically acceptable excipient.

In accordance with another embodiment, there is provided a method for modulating AR activity, the method comprising administering to a mammalian cell a compound having a structure of Formula I set out above.

The modulating of the androgen receptor (AR) activity may be in a mammalian cell. The modulating of the androgen receptor (AR) activity may be in a mammal. The mammal may be a human.

Alternatively, the administering may be to a mammal. The administering may be to a mammal in need thereof and in an effective amount for the treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration.

Each X, X' and X'' may independently be H, CH$_3$, CH$_2$F, CH$_2$Cl, CH$_2$Br, CH$_2$I, CH$_2$OJ''', CH$_2$OG, CH$_2$OGOG', GOG', GOG'OG'', CH$_2$SG, CH$_2$NH$_2$, CH$_2$NHG, or CH$_2$NG$_2$. Each Z, Z', and Z'' may independently be N, CH, CF, CCl, CBr, CI or COH. R$^3$ may be

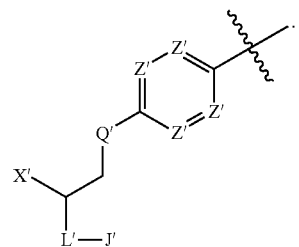

Each Z, Z' and Z'' may independently be N, CH, CF, CCl, CBr, CI, COH, CNH$_2$, COSO$_3$H, or COPO$_3$H$_2$. Each Z, Z' and Z'' may independently be N, CH, CF, CCl, CBr, CI, or COH. Each Z, Z' and Z'' may independently be CH, CF, CCl, CBr, or CI. Each Z, Z' and Z'' may independently be CH, CCl, or CBr. Each Z, Z', and Z'' may be CH.

Each of Q, Q' and Q'' may be G, O, CH$_2$, CHG, S, or NH. Each of Q, Q' and Q'' may be O, CH$_2$, S, or NH. Each of Q, Q' and Q'' may be O, CH$_2$, or NH. Each of Q, Q' and Q'' may be O, or CH$_2$. Each of Q, Q' and Q'' may be O. Each of Q, Q' and Q'' may be G, O, CHG, or NH. Each of Q, Q' and Q'' may be G, O, or CHG. Each of Q, Q' and Q'' may be G, or O.

Each of R', R$^{1'}$, R$^2$ and R$^{2'}$ may independently be H, or a branched or unbranched, substituted or unsubstituted, C$_1$-C$_{10}$ alkyl. Each of R$^1$, R$^{1'}$, R$^2$ and R$^{2'}$ may independently be H, or a branched or unbranched, substituted or unsubstituted, C$_1$-C$_9$ alkyl. Each of R$^1$, R$^{1'}$, R$^2$ and R$^{2'}$ may independently be H, or a branched or unbranched, substituted or unsubstituted, C$_1$-C$_8$ alkyl. Each of R$^1$, R$^{1'}$, R$^2$ and R$^{2'}$ may independently be H, or a branched or unbranched, substituted or unsubstituted, C$_1$-C$_7$ alkyl. Each of R$^1$, R$^{1'}$, R$^2$ and R$^{2'}$ may independently be H, or a branched or unbranched, substituted or unsubstituted, C$_1$-C$_6$ alkyl. Each of R$^1$, R$^{1'}$, R$^2$ and R$^{2'}$ may independently be H, or a branched or unbranched, substituted or unsubstituted, C$_1$-C$_5$ alkyl. Each of R$^1$, R$^{1'}$, R$^2$ and R$^{2'}$ may independently be H, or a branched or unbranched, substituted or unsubstituted, C$_1$-C$_4$ alkyl. Each of R$^1$, R$^{1'}$, R$^2$ and R$^{2'}$ may independently be H, or a branched or unbranched, substituted or unsubstituted, C$_1$-C$_3$ alkyl. Each of R$^1$, R$^{1'}$, R$^2$ and R$^{2'}$ may independently be H, or a branched or unbranched, substituted or unsubstituted, C$_1$-C$_2$ alkyl. Each R$^1$, R$^{1'}$, R$^2$ and R$^{2'}$ may be H or CH$_3$. Each R$^1$, R$^{1'}$, R$^2$ and R$^{2'}$ may be CH$_3$. Each R$^1$, R$^{1'}$, R$^2$ and R$^{2'}$ may be H.

X may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', CH$_3$OCH$_3$, CH$_3$OCH$_2$CH$_3$, G, CH$_2$OG, CH$_2$OGOG', GOG', GOG'OG'', CH$_2$SG, CH$_2$NH$_2$, CH$_2$NHG, or CH$_2$NG$_2$. X may be H, CH$_3$, CH$_3$OCH$_3$, CH$_3$OCH$_2$CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', G, CH$_2$OG, CH$_2$NH$_2$, CH$_2$NHG, or CH$_2$NG$_2$. X may be H, CH$_3$, CH$_3$OCH$_3$, CH$_3$OCH$_2$CH$_3$, CH$_2$F, CH$_2$Cl, CH$_2$Br, CH$_2$I, CH$_2$OJ'", CH$_2$OG, or CH$_2$OGOG'. X may be H, CH$_3$, CH$_3$OCH$_3$, CH$_3$OCH$_2$CH$_3$, CH$_2$F, CH$_2$Cl, CH$_2$Br, CH$_2$I, CH$_2$OJ'", or CH$_2$OG. X may be H, CH$_3$, CH$_3$OCH$_3$, CH$_3$OCH$_2$CH$_3$, CH$_2$F, CH$_2$Cl, CH$_2$Br, CH$_2$I, or CH$_2$OJ'". X may be H, CH$_3$, CH$_3$OCH$_3$, CH$_3$OCH$_2$CH$_3$, CH2F, CH$_2$Cl, CH$_2$Br, or CH$_2$I. X may be CH$_3$, CH$_3$OCH$_2$CH$_3$, CH$_2$Cl, CH$_2$F, CH$_2$I, CH$_2$Br, CH$_2$OH, CH$_2$OCH$_3$, or CH$_2$O(isopropyl). X may be CH$_3$, CH$_2$Cl, CH$_2$F, CH$_2$I, CH$_2$Br, CH$_2$OH, CH$_3$OCH$_2$CH$_3$, or CH$_2$OCH$_3$. X may be CH$_3$, CH$_2$Cl, CH$_2$F, CH$_2$I, CH$_2$Br, CH$_2$OH, or CH$_2$OCH$_3$. X may be CH$_3$, CH$_2$OH, CH$_2$OCH$_3$, or CH$_2$OCH$_2$CH$_3$. X may be CH$_2$Cl, CH$_2$F, CH$_2$I, or CH$_2$Br.

X' may be H, CH$_3$, CH$_2$F, CH$_2$Cl, CH$_2$Br, CH$_2$I, CH$_2$OJ'", CH$_2$OG, CH$_2$OGOG', GOG', GOG'OG", CH$_2$SG, CH$_2$NH$_2$, CH$_2$NHG, or CH$_2$NG$_2$. X' may be H, CH$_3$, CH$_2$F, CH$_2$Cl, CH$_2$Br, CH$_2$I, CH$_2$OJ'", CH$_2$OG, or CH$_2$OGOG'. X' may be CH$_2$Cl, CH$_2$F, CH$_2$I, CH$_2$Br, CH$_2$OH, CH$_2$OCH$_3$, CH$_2$O(isopropyl), or CH$_2$OC$_2$H$_4$OC$_4$H$_9$. X' may be H, CH$_3$, CH$_3$OCH$_3$, CH$_3$OCH$_2$CH$_3$, CH2F, CH$_2$Cl, CH$_2$Br, or CH$_2$I. X' may be CH$_3$, CH$_3$OCH$_2$CH$_3$, CH$_2$Cl, CH$_2$F, CH$_2$I, CH$_2$Br, CH$_2$OH, CH$_2$OCH$_3$, or CH$_2$O(isopropyl). X' may be CH$_3$, CH$_2$Cl, CH$_2$F, CH$_2$I, CH$_2$Br, CH$_2$OH, CH$_3$OCH$_2$CH$_3$, or CH$_2$OCH$_3$. X' may be CH$_3$, CH$_2$Cl, CH$_2$F, CH$_2$I, CH$_2$Br, CH$_2$OH, or CH$_2$OCH$_3$. X' may be CH$_3$, CH$_2$OH, CH$_2$OCH$_3$, or CH$_2$OCH$_2$CH$_3$. X' may be CH$_2$Cl, CH$_2$F, CH$_2$I, or CH$_2$Br.

X" may be H, CH$_3$, CH$_2$I, CH$_2$Cl, CH$_2$Br, CH$_2$F, CH$_2$OJ'", CH$_2$OG or CH$_2$OGOG'. X" may be CH$_2$Cl, CH$_2$F, CH$_2$I, CH$_2$Br, CH$_2$OH, CH$_2$OCH$_3$, CH$_2$O(isopropyl), or CH$_2$OC$_2$H$_4$OC$_4$H$_9$. X" may be H, CH$_3$, CH$_3$OCH$_3$, CH$_3$OCH$_2$CH$_3$, CH2F, CH$_2$Cl, CH$_2$Br, or CH$_2$I. X" may be CH$_3$, CH$_3$OCH$_2$CH$_3$, CH$_2$Cl, CH$_2$F, CH$_2$I, CH$_2$Br, CH$_2$OH, CH$_2$OCH$_3$, or CH$_2$O(isopropyl). X" may be CH$_3$, CH$_2$Cl, CH$_2$F, CH$_2$I, CH$_2$Br, CH$_2$OH, CH$_3$OCH$_2$CH$_3$, or CH$_2$OCH$_3$. X" may be CH$_3$, CH$_2$Cl, CH$_2$F, CH$_2$I, CH$_2$Br, CH$_2$OH, or CH$_2$OCH$_3$. X" may be CH$_3$, CH$_2$OH, CH$_2$OCH$_3$, or CH$_2$OCH$_2$CH$_3$. X" may be CH$_2$Cl, CH$_2$F, CH$_2$I, or CH$_2$Br. X" may be CH$_2$OCH$_3$ and X may be CH$_2$OCH$_3$.

Each J, J', J", and J'", when present, may independently be H or an amino acid based moiety or a polyethylene glycol based moiety selected from TABLE 1. Alternatively, each J, J', J", and J'", when present, may independently be H or an amino acid based moiety selected from TABLE 1. Each J, J', J", and J'", when present, may independently be an amino acid based moiety or a polyethylene glycol based moiety selected from TABLE 1. Alternatively, each J, J', J", and J'", when present, may independently be an amino acid based moiety selected from TABLE 1. Each J, J' J", J'", when present, may be H. Each J, J', J", and J'", when present may be

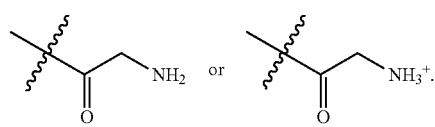

L, L' and L", when present, may independently be O, S, NH or N$^+$H$_2$. L, L' and L", when present, may independently be O, S, or NH. L, L' and L", when present, may independently be O, or S. Alternatively, L, L' and L", when present, may be O.

Each G, G' and G" may independently be a branched, unbranched, or aromatic cyclic or non-aromatic cyclic, substituted or unsubstituted, saturated or unsaturated C$_1$-C$_{10}$ alkyl. Each G, G' and G" may independently be a branched, unbranched, or non-aromatic cyclic, substituted or unsubstituted, saturated or unsaturated C$_1$-C$_{10}$ alkyl. Each G, G' and G" may independently be a branched, unbranched, or non-aromatic cyclic, substituted or saturated or unsaturated C$_1$-C$_{10}$ alkyl. Each G G' and G" may independently be a branched, unbranched, or aromatic cyclic or non-aromatic cyclic, substituted or unsubstituted, saturated or unsaturated C$_1$-C$_9$ alkyl. Each G G' and G" may independently be a branched, unbranched, or aromatic cyclic or non-aromatic cyclic, substituted or unsubstituted, saturated or unsaturated C$_1$-C$_8$ alkyl. Each G G' and G" may independently be a branched, unbranched, or aromatic cyclic or non-aromatic cyclic, substituted or unsubstituted, saturated or unsaturated C$_1$-C$_7$ alkyl. Each G G' and G" may independently be a branched, unbranched, or aromatic cyclic or non-aromatic cyclic, substituted or unsubstituted, saturated or unsaturated C$_1$-C$_6$ alkyl. Each G, G' and G" may independently be a branched, unbranched, or aromatic cyclic or non-aromatic cyclic, substituted or unsubstituted, saturated or unsaturated C$_1$-C$_5$ alkyl. Each G, G' and G" may independently be a branched, unbranched, or non-aromatic cyclic, substituted or unsubstituted, saturated or unsaturated C$_1$-C$_4$ alkyl. Each G, G' and G" may independently be a branched, unbranched, or non-aromatic cyclic, substituted or unsubstituted, saturated or unsaturated C$_1$-C$_3$ alkyl.

An optional substituent, if present, may be selected from the group consisting of: oxo (i.e. =O), OJ'", COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$. An optional substituent, if present, may be selected from the group consisting of: oxo (i.e. =O), OJ'", COOH, R, OH, OR, F, Cl, Br, I, NH$_2$, NHR, NR$_2$, SO$_3$H, SO$_3$R, SO$_2$R, and NO$_2$. An optional substituent, if present, may be selected from the group consisting of: oxo (i.e. =O), OJ'", COOH, R, OH, OR, F, Cl, Br, I, NH$_2$, and NO$_2$. An optional substituent, if present, may be selected from the group consisting of: oxo (i.e. =O), OJ'", COOH, R, OH, OR, F, Cl, Br, and I. An optional substituent, if present, may be selected from the group consisting of: oxo (i.e. =O), OJ'", COOH, OH, F, Cl, Br, and I. An optional substituent, if present, may be selected from the group consisting of: oxo (i.e. =O), OJ'", COOH, OH, F, and Cl. R may be an unsubstituted C$_1$-C$_{10}$ alkyl. R may be an unsubstituted C$_1$-C$_9$ alkyl. R may be an unsubstituted C$_1$-C$_8$ alkyl. R may be an unsubstituted C$_1$-C$_7$ alkyl. R may be an unsubstituted C$_1$-C$_6$ alkyl. R may be an unsubstituted C$_1$-C$_5$ alkyl. R may be an unsubstituted C$_1$-C$_4$ alkyl. R may be an unsubstituted C$_1$-C$_3$ alkyl. R may be an unsubstituted C$_1$-C$_2$ alkyl. R may be an unsubstituted C$_1$ alkyl.

The compound may be selected from one or more of the following:

9
10
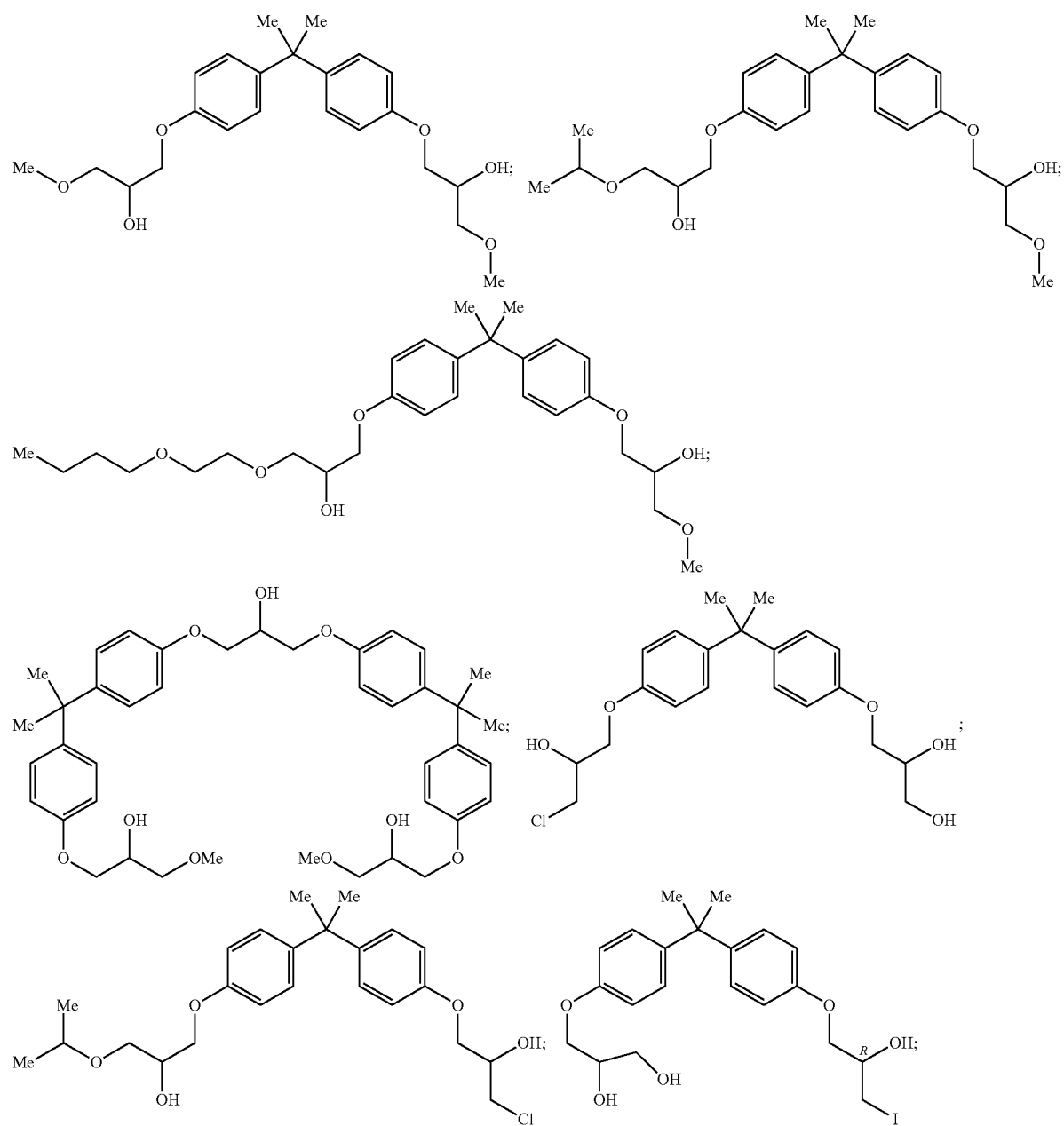
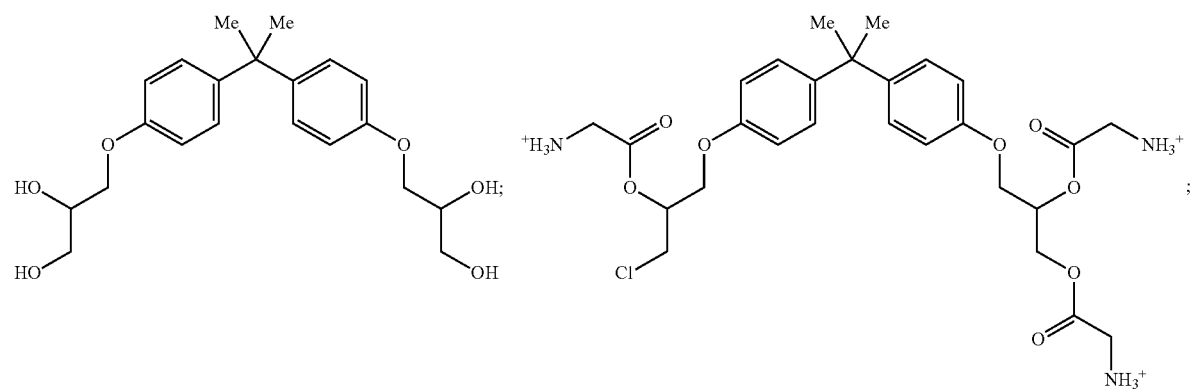

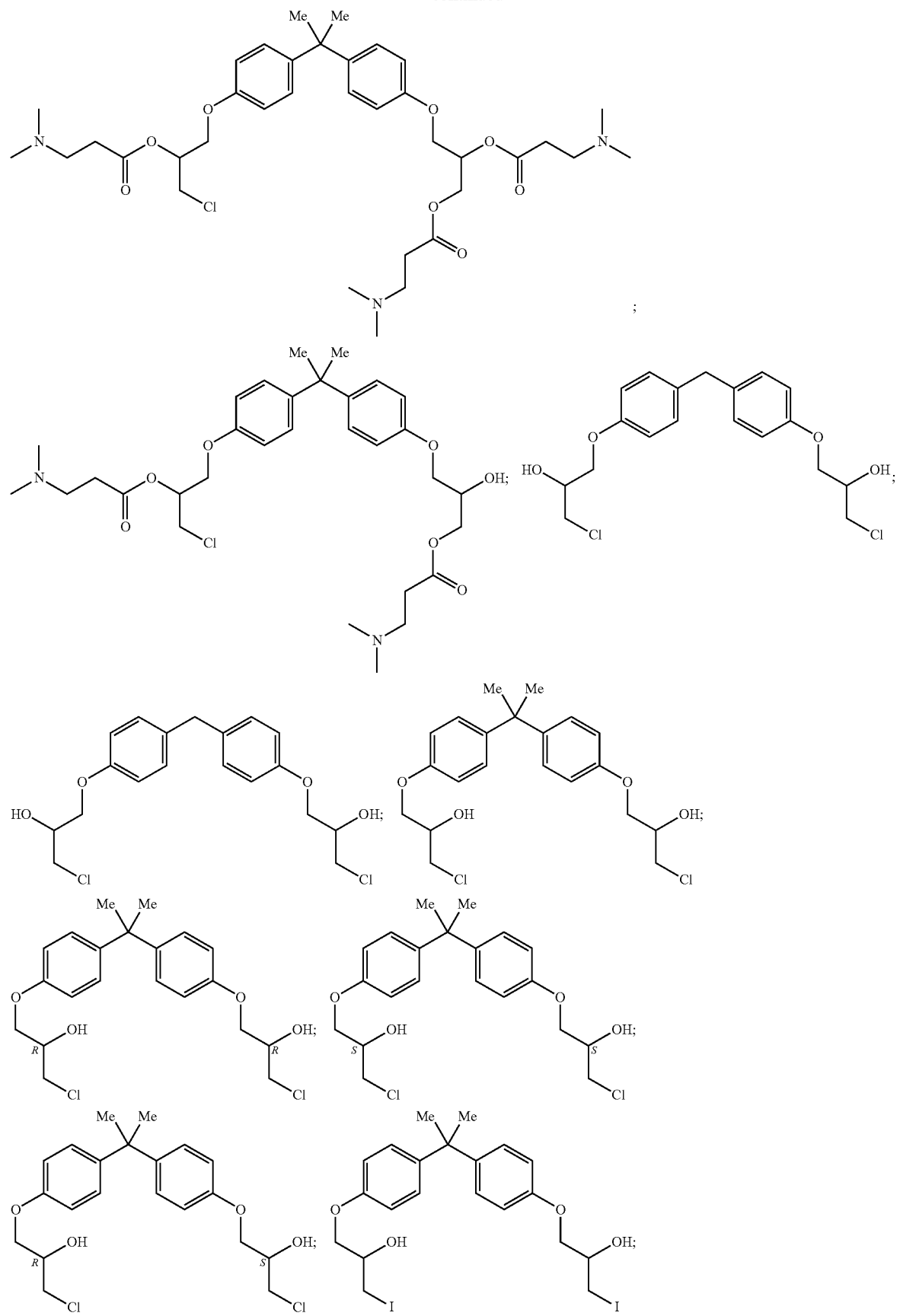

-continued
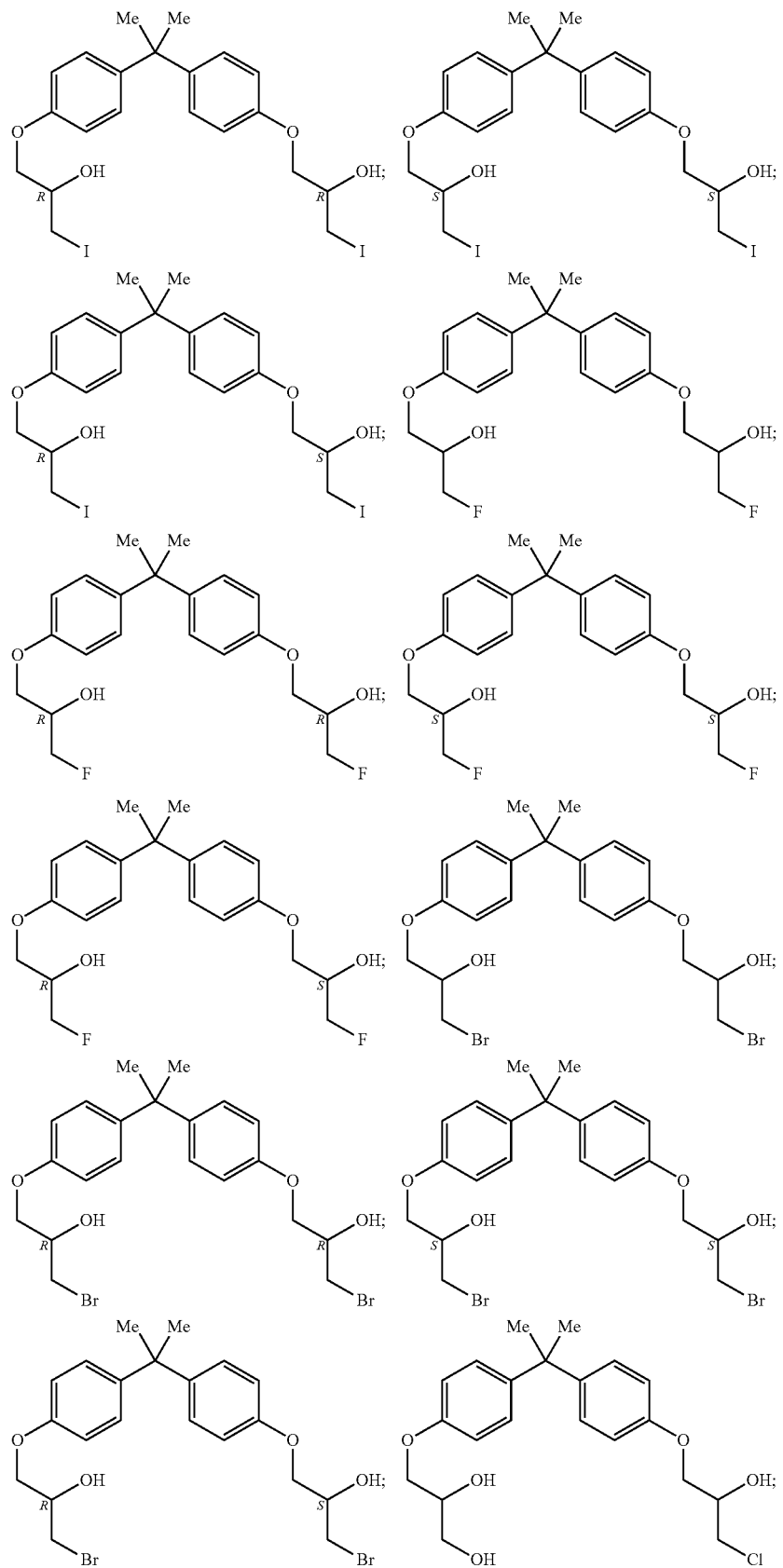

-continued
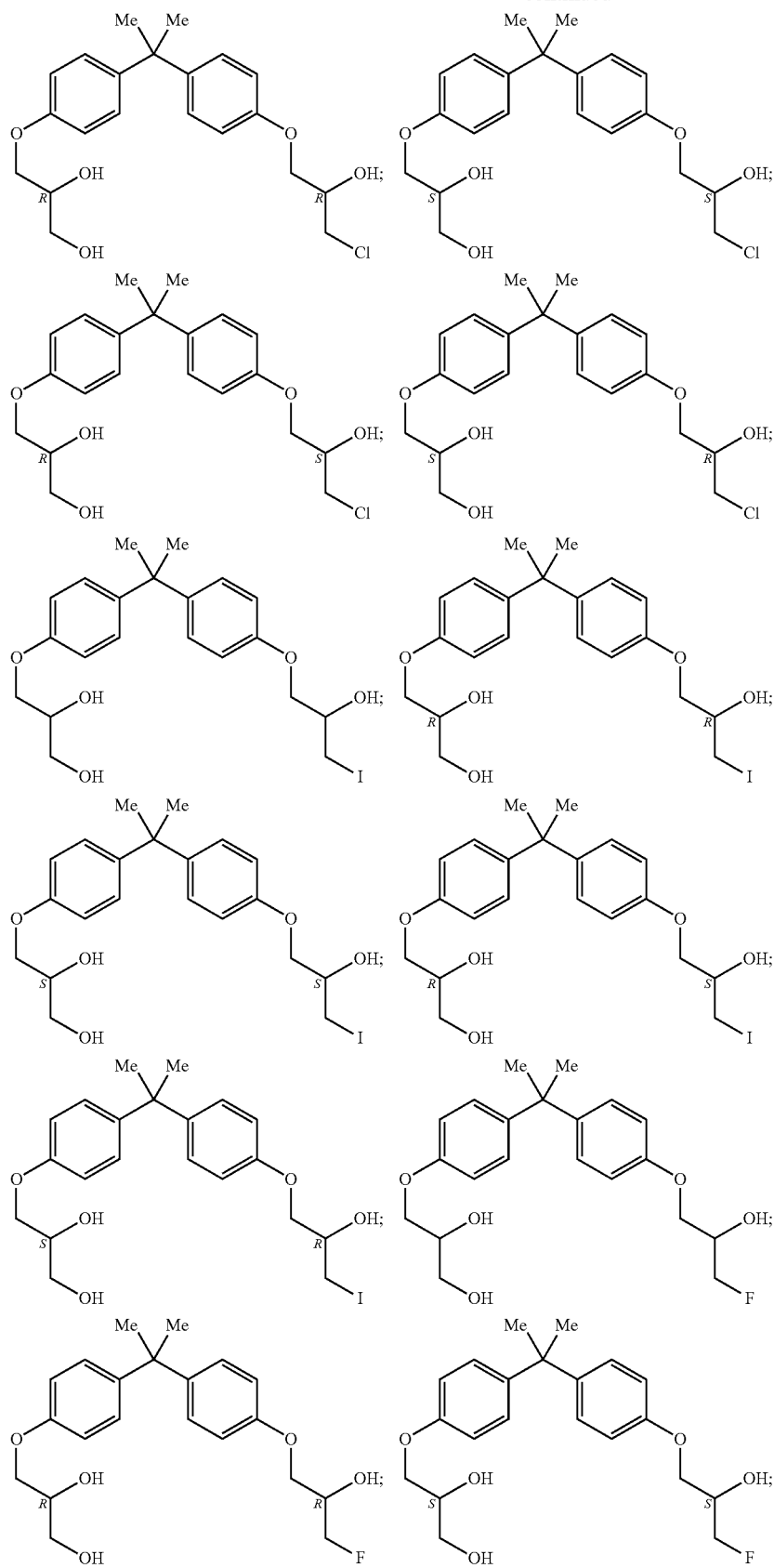

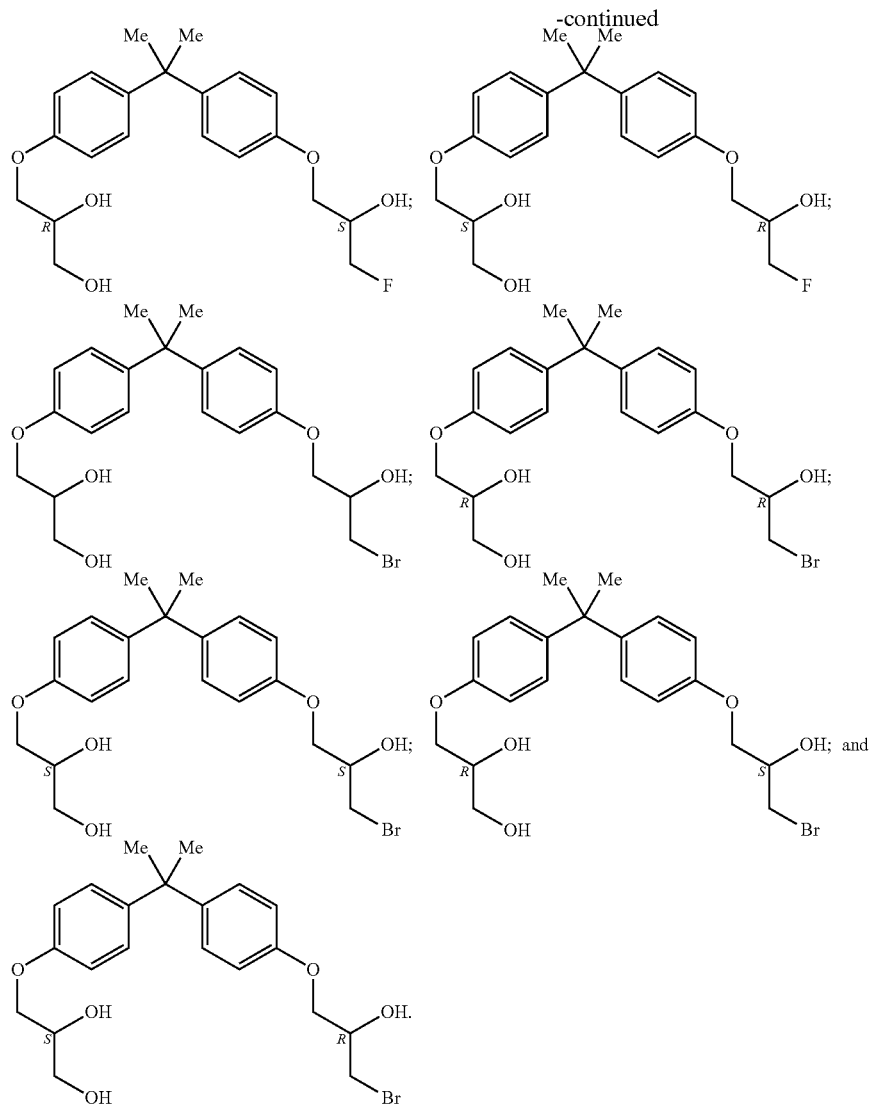

The compounds described herein are meant to include all racemic mixtures and all individual enantiomers or combinations thereof, whether or not they are represented herein. Alternatively, one or more of the OH groups on the above compounds may be substituted to replace the H with a moiety selected from TABLE 1.

The mammalian cell may be a human cell. The modulating AR activity may be for inhibiting AR N-terminal domain activity. The modulating AR activity may be for inhibiting AR N-terminal domain (NTD) activity. The modulating may be in vivo. The modulating AR activity may be for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration. The indication may be prostate cancer. The prostate cancer may be androgen-independent prostate cancer. The prostate cancer may be androgen-dependent prostate cancer.

In accordance with another embodiment, there are provided compounds having structures represented by Formula II

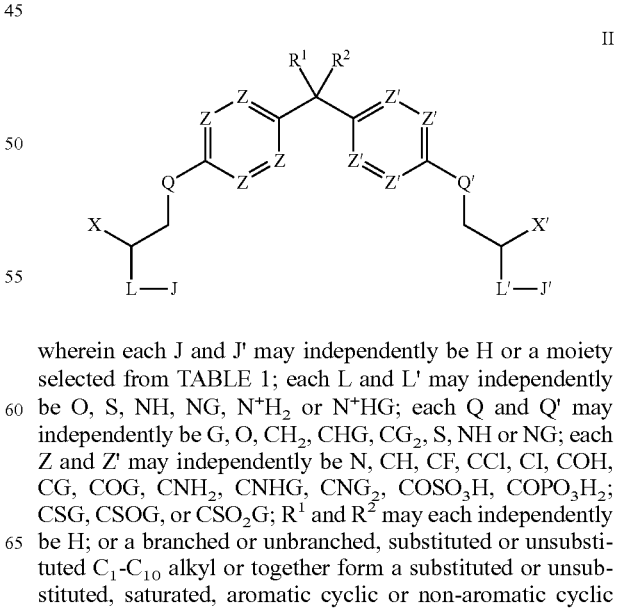

wherein each J and J' may independently be H or a moiety selected from TABLE 1; each L and L' may independently be O, S, NH, NG, $N^+H_2$ or $N^+HG$; each Q and Q' may independently be G, O, $CH_2$, CHG, $CG_2$, S, NH or NG; each Z and Z' may independently be N, CH, CF, CCl, CI, COH, CG, COG, $CNH_2$, CNHG, $CNG_2$, $COSO_3H$, $COPO_3H_2$; CSG, CSOG, or $CSO_2G$; $R^1$ and $R^2$ may each independently be H; or a branched or unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; X may be $CH_2OG$, $CH_2OGOG'$, $CH_2SG$, $CH_2NH_2$, $CH_2NHG$, $CH_2I$, $CH_2Br$, $CH_2F$, or $CH_2NG_2$; X' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2F$, $CHF_2$, $CF_3$, $CH_2OJ'''$, $CH_2OG$, $CH_2OGOG'$, $GOG'$, $GOG'OG''$, $CH_2SG$, $CH_2NH_2$, $CH_2NHG$, $CH_2NG_2$, or

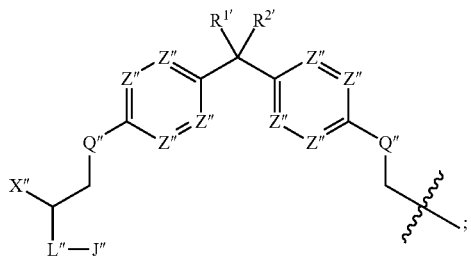

$R^{1'}$ and $R^{2'}$ may each independently be H, or a branched or unbranched, substituted or unsubstituted $C_1$-$C_{10}$ alkyl, or $R^{1'}$ and $R^{2'}$ together form a substituted or unsubstituted, saturated, aromatic cyclic or non-aromatic cyclic $C_3$-$C_{10}$ alkyl; each J'' and J''' may independently be H or a moiety selected from TABLE 1; L'' may be O, S, NH, NG, $N^+H_2$, or $N^+HG$; each Z'' may independently be N, CH, CF, CCl, CBr, CI, COH, CG, COG, $CNH_2$, CNHG, $CNG_2$, $COSO_3H$, $COPO_3H_2$; CSG, CSOG, or $CSO_2G$; Q'' may be G, O, $CH_2$, CHG, $CG_2$, S, NH or NG; X'' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2OJ'''$, G, $CH_2OG$, $CH_2OGOG'$, $GOG'$, $GOG'OG''$, $CH_2SG$, $CH_2NH_2$, $CH_2NHG$, or $CH_2NG_2$; and each G, G', and G'' may independently be a branched or unbranched, non-aromatic cyclic, substituted or unsubstituted, saturated $C_1$-$C_{10}$ alkyl; wherein an optional substituent if present may be selected from the group consisting of: oxo (i.e. =O), OJ''', COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R may be an unsubstituted $C_1$-$C_{10}$ alkyl.

Alternatively, each J and J' may independently be H or a moiety selected from TABLE 1; each L and L' may independently be O, S, NH, NG, $N^+H_2$ or $N^+HG$; each Q and Q' may independently be G, O, $CH_2$, CHG, $CG_2$, S, NH or NG; each Z and Z' may independently be N, CH, CF, CCl, CBr, CI, COH, CG, COG, $CNH_2$, CNHG, $CNG_2$, $COSO_3H$, $COPO_3H_2$; CSG, CSOG, or $CSO_2G$; $R^1$ and $R^2$ may each independently be H; or a branched or unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; X may be $CH_2OG$, $CH_2OGOG'$, $CH_2SG$, $CH_2NH_2$, $CH_2NHG$, $CH_2I$, $CH_2Br$, or $CH_2F$; X' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2F$, $CHF_2$, $CF_3$, $CH_2OJ'''$, $CH_2OG$, $CH_2OGOG'$, $GOG'$, $GOG'OG''$, $CH_2SG$, $CH_2NH_2$, $CH_2NHG$, $CH_2NG_2$, or

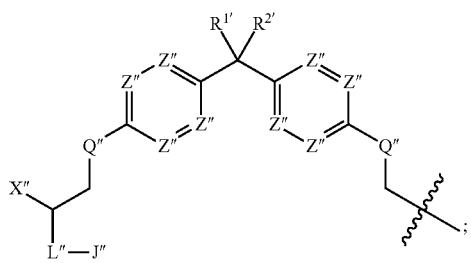

$R^{1'}$ and $R^{2'}$ may each independently be H, or a branched or unbranched, substituted or unsubstituted $C_1$-$C_{10}$ alkyl, or $R^{1'}$ and $R^{2'}$ together form a substituted or unsubstituted, saturated, aromatic cyclic or non-aromatic cyclic $C_3$-$C_{10}$ alkyl; each J'' and J''' may independently be H or a moiety selected from TABLE 1; L'' may be O, S, NH, NG, $N^+H_2$, or $N^+HG$; each Z'' may independently be N, CH, CF, CCl, CBr, CI, COH, CG, COG, $CNH_2$, CNHG, $CNG_2$, $COSO_3H$, $COPO_3H_2$; CSG, CSOG, or $CSO_2G$; Q'' may be G, O, $CH_2$, CHG, $CG_2$, S, NH or NG; X'' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2OJ'''$, G, $CH_2OG$, $CH_2OGOG'$, $GOG'$, $GOG'OG''$, $CH_2SG$, $CH_2NH_2$, $CH_2NHG$, or $CH_2NG_2$; and each G, G', and G'' may independently be a branched or unbranched, non-aromatic cyclic, substituted or unsubstituted, saturated $C_1$-$C_{10}$ alkyl; wherein an optional substituent if present may be selected from the group consisting of: oxo (i.e. =O), OJ''', COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R may be an unsubstituted $C_1$-$C_{10}$ alkyl.

Alternatively, wherein each J and J' may independently be H or a moiety selected from TABLE 1; each L and L' may independently be O, S, or NH; each Q and Q' may independently be O, $CH_2$, S, or NH; each Z and Z' may independently be N, CH, CF, CCl, CI, COH, or $CNH_2$; $R^1$ and $R^2$ may each independently be H; or a branched or unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; X may be $CH_2OG$, $CH_2OGOG'$, $CH_2SG$, $CH_2NH_2$, $CH_2NHG$, $CH_2I$, $CH_2Br$, $CH_2F$, or $CH_2NG_2$; X' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2F$, $CHF_2$, $CF_3$, $CH_2OJ'''$, $CH_2OG$, $CH_2OGOG'$, $GOG'$, $GOG'OG''$, $CH_2SG$, $CH_2NH_2$, $CH_2NHG$, $CH_2NG_2$; $R^{1'}$ and $R^{2'}$ may each independently be H, or a branched or unbranched, substituted or unsubstituted $C_1$-$C_5$ alkyl, or $R^{1'}$ and $R^{2'}$ together form a substituted or unsubstituted, saturated, aromatic cyclic or non-aromatic cyclic $C_3$-$C_{10}$ alkyl; each J'' and J''' may independently be H or a moiety selected from TABLE 1; L'' may be O, S, or NH; each Z'' may independently be N, CH, CF, CCl, CI, COH, or $CNH_2$; Q'' may be O, $CH_2$, S, or NH; X'' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2OJ'''$, G, $CH_2OG$, $CH_2OGOG'$, $CH_2SG$, $CH_2NH_2$, $CH_2NHG$, $CH_2I$, $CH_2Br$, $CH_2F$, or $CH_2NG_2$ and each G, G', and G'' may independently be a branched or unbranched, non-aromatic cyclic, substituted or unsubstituted, saturated $C_1$-$C_5$ alkyl; wherein an optional substituent if present may be selected from the group consisting of: oxo (i.e. =O), OJ''', COOH, R, OH, OR, F, Cl, Br, I, $NH_2$, CN, SH, $SO_3H$, and $NO_2$ wherein R may be an unsubstituted $C_1$-$C_5$ alkyl.

X' may be H, $CH_3$, $CH_2F$, $CH_2Cl$, $CH_2Br$, $CH_2I$, $CH_2OG$, $CH_2OGOG'$, $GOG'$, $GOG'OG''$, $CH_2SG$, $CH_2NH_2$, $CH_2NHG$, $CH_2NG_2$, or

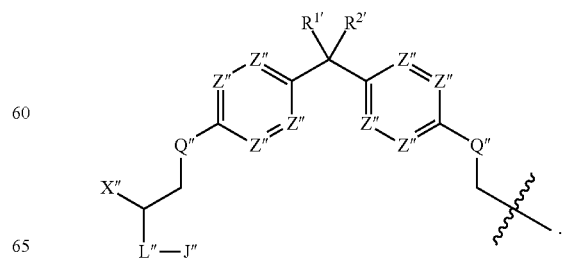

X' may be H, CH$_3$, CH$_2$F, CH$_2$Cl, CH$_2$Br, CH$_2$I, CH$_2$OG, CH$_2$OGOG', GOG', GOG'OG", CH$_2$SG, CH$_2$NH$_2$, CH$_2$NHG, or CH$_2$NG$_2$. X' may be H, CH$_3$, CH$_2$F, CH$_2$Cl, CH$_2$Br, CH$_2$I, CH$_2$OG, CH$_2$OGOG', GOG', or GOG'OG". X' may be H, CH$_3$, CH$_2$F, CH$_2$Cl, CH$_2$Br, CH$_2$I, CH$_2$OG, or CH$_2$OGOG'. X' may be H, CH$_3$, CH$_2$F, CH$_2$Cl, CH$_2$Br, CH$_2$I, or CH$_2$OG. X' may be H, CH$_3$, CH$_2$F, CH$_2$Cl, CH$_2$Br, CH$_2$I, CH$_2$O(isopropyl), CH$_2$OCH$_3$, or CH$_2$OCH$_2$CH$_3$. X' may be H, CH$_3$, CH$_2$F, CH$_2$Cl, CH$_2$Br, CH$_2$I, CH$_2$O(isopropyl), CH$_2$OCH$_3$, or CH$_2$OCH$_2$CH$_3$. X' may be H, CH$_3$, CH$_2$F, CH$_2$Cl, CH$_2$Br, CH$_2$I, or CH$_2$OCH$_3$.

X" may be H, CH$_3$, CH$_2$F, CH$_2$Cl, CH$_2$Br, CH$_2$I, CH$_2$OG, CH$_2$OGOG', GOG', GOG'OG", CH$_2$O(isopropyl), CH$_2$SG, CH$_2$NH$_2$, CH$_2$NHG, or CH$_2$NG$_2$. X" may be H, CH$_3$, CH$_2$F, CH$_2$Cl, CH$_2$Br, CH$_2$I, CH$_2$O(isopropyl), CH$_2$OG, CH$_2$OGOG', GOG', or GOG'OG". X" may be H, CH$_3$, CH$_2$F, CH$_2$Cl, CH$_2$Br, CH$_2$I, CH$_2$O(isopropyl), CH$_2$OCH$_3$, or CH$_2$OCH$_2$CH$_3$. X" may be H, CH$_3$, CH$_2$F, CH$_2$Cl, CH$_2$Br, CH$_2$I, or CH$_2$OCH$_3$. X" may be H, CH$_3$, CH$_2$F, CH$_2$Cl, CH$_2$Br, or CH$_2$I.

X may be CH$_2$OG, CH$_2$OGOG', CH$_2$SG, CH$_2$I, CH$_2$Br, or CH$_2$F. X may be CH$_2$I, CH$_2$Br, CH$_2$F, CH$_2$OG, or CH$_2$OGOG'. X may be CH$_2$I, CH$_2$Br, CH$_2$F, CH$_2$OCH$_3$, CH$_2$O(isopropyl), or CH$_2$OC$_2$H$_4$OC$_4$H$_9$. X may be CH$_2$I, CH$_2$Br, CH$_2$F, CH$_2$OCH$_3$, or CH$_2$OCH$_2$CH$_3$. X may be CH$_2$I, CH$_2$Br, CH$_2$F, or CH$_2$OCH$_3$. X may be CH$_2$I, CH$_2$Br, or CH$_2$F.

Each Z, Z' and Z" may independently be N, CH, CF, CCl, CBr, CI or COH. Each Z, Z' and Z" may independently be CH, CF, CCl, CBr, CI or COH. Alternatively, each Z, Z' and Z" may independently be CH, CF, CCl, CBr, or CI. Each Z, Z', and Z" may be CH.

Each of Q, Q' and Q" may be O.

Each of R$^1$, R$^{1'}$, R$^2$ and R$^{2'}$ may independently be H, or a branched or unbranched, substituted or unsubstituted, C$_1$-C$_{10}$ alkyl. Each of R$^1$, R$^{1'}$, R$^2$ and R$^{2'}$ may independently be H, or a branched or unbranched, substituted or unsubstituted, C$_1$-C$_9$ alkyl. Each of R$^1$, R$^{1'}$, R$^2$ and R$^{2'}$ may independently be H, or a branched or unbranched, substituted or unsubstituted, C$_1$-C$_8$ alkyl. Each of R$^1$, R$^{1'}$, R$^2$ and R$^{2'}$ may independently be H, or a branched or unbranched, substituted or unsubstituted, C$_1$-C$_7$ alkyl. Each of R$^1$, R$^{1'}$, R$^2$ and R$^{2'}$ may independently be H, or a branched or unbranched, substituted or unsubstituted, C$_1$-C$_6$ alkyl. Each of R$^1$, R$^{1'}$, R$^2$ and R$^{2'}$ may independently be H, or a branched or unbranched, substituted or unsubstituted, C$_1$-C$_5$ alkyl. Each of R$^1$, R$^{1'}$, R$^2$ and R$^{2'}$ may independently be H, or a branched or unbranched, substituted or unsubstituted, C$_1$-C$_4$ alkyl. Each of R$^1$, R$^{1'}$, R$^2$ and R$^{2'}$ may independently be H, or a branched or unbranched, substituted or unsubstituted, C$_1$-C$_3$ alkyl. Each of R$^1$, R$^{1'}$, R$^2$ and R$^{2'}$ may independently be H, or a branched or unbranched, substituted or unsubstituted, C$_1$-C$_2$ alkyl. Each R$^1$, R$^{1'}$, R$^2$ and R$^{2'}$ may be H or CH$_3$. Each R$^1$, R$^{1'}$, R$^2$ and R$^{2'}$ may be CH$_3$. Each R$^1$, R$^{1'}$, R$^2$ and R$^{2'}$ may be H.

Each J, J', J", and J"', when present, may independently be H or an amino acid based moiety or a polyethylene glycol based moiety selected from TABLE 1. Alternatively, each J, J', J", and J"', when present, may independently be H or an amino acid based moiety selected from TABLE 1. Each J, J', J", and J"', when present, may independently be an amino acid based moiety or a polyethylene glycol based moiety selected from TABLE 1. Alternatively, each J, J', J", and J"', when present, may independently be an amino acid based moiety selected from TABLE 1. Each J, J' J", J"', when present, may be H. Each J, J', J", and J"', when present may be

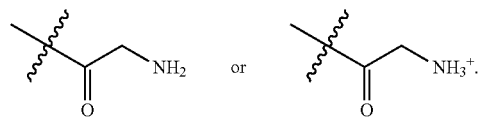

Each L, L', and L", when present, may independently be O, NH or N$^+$H$_2$. Each L L', and L", when present, may be O or S. Alternatively, each L L', and L", when present, may be O.

Each G, G' and G" may independently be a branched, unbranched, or non-aromatic cyclic, substituted or unsubstituted, saturated C$_1$-C$_{10}$ alkyl. Each G, G' and G" may independently be a branched, unbranched, or non-aromatic cyclic, substituted or unsubstituted, saturated C$_1$-C$_{10}$ alkyl. Each G, G' and G" may independently be a branched, unbranched, or non-aromatic cyclic, substituted or saturated C$_1$-C$_{10}$ alkyl. Each G G' and G" may independently be a branched, unbranched, or non-aromatic cyclic, substituted or unsubstituted, saturated C$_1$-C$_9$ alkyl. Each G G' and G" may independently be a branched, unbranched, or non-aromatic cyclic, substituted or unsubstituted, saturated C$_1$-C$_8$ alkyl. Each G G' and G" may independently be a branched, unbranched, or non-aromatic cyclic, substituted or unsubstituted, saturated C$_1$-C$_7$ alkyl. Each G G' and G" may independently be a branched, unbranched, or non-aromatic cyclic, substituted or unsubstituted, saturated C$_1$-C$_6$ alkyl. Each G, G' and G" may independently be a branched, unbranched, or non-aromatic cyclic, substituted or unsubstituted, saturated C$_1$-C$_5$ alkyl. Each G, G' and G" may independently be a branched, unbranched, or non-aromatic cyclic, substituted or unsubstituted, saturated C$_1$-C$_4$ alkyl. Each G, G' and G" may independently be a branched, unbranched, or non-aromatic cyclic, substituted or unsubstituted, saturated C$_1$-C$_3$ alkyl.

An optional substituent, if present, may be selected from the group consisting of: oxo (i.e. =O), OJ'", COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$. An optional substituent, if present, may be selected from the group consisting of: oxo (i.e. =O), OJ'", COOH, R, OH, OR, F, Cl, Br, I, NH$_2$, NHR, NR$_2$, SO$_3$H, SO$_3$R, SO$_2$R, and NO$_2$. An optional substituent, if present, may be selected from the group consisting of: oxo (i.e. =O), OJ'", COOH, R, OH, OR, F, Cl, Br, I, NH$_2$, and NO$_2$. An optional substituent, if present, may be selected from the group consisting of: oxo (i.e. =O), OJ'", COOH, R, OH, OR, F, Cl, Br, and I. An optional substituent, if present, may be selected from the group consisting of: oxo (i.e. =O), OJ'", COOH, OH, F, Cl, Br, and I. An optional substituent, if present, may be selected from the group consisting of: oxo (i.e. =O), OJ'", COOH, OH, F, and Cl. R may be an unsubstituted C$_1$-C$_{10}$ alkyl. R may be an unsubstituted C$_1$-C$_9$ alkyl. R may be an unsubstituted C$_1$-C$_8$ alkyl. R may be an unsubstituted C$_1$-C$_7$ alkyl. R may be an unsubstituted C$_1$-C$_6$ alkyl. R may be an unsubstituted C$_1$-C$_5$ alkyl. R may be an unsubstituted C$_1$-C$_4$ alkyl. R may be an unsubstituted C$_1$-C$_3$ alkyl. R may be an unsubstituted C$_1$-C$_2$ alkyl. R may be an unsubstituted C$_1$ alkyl.

The compound may be selected from one or more of the following:

23    24
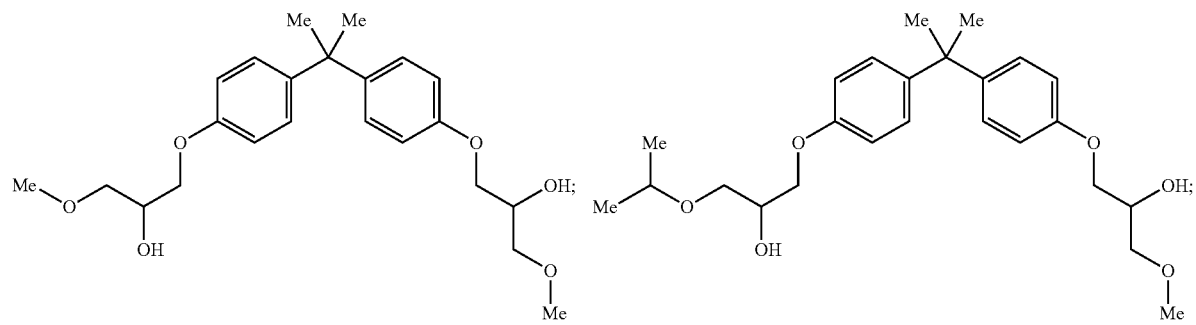
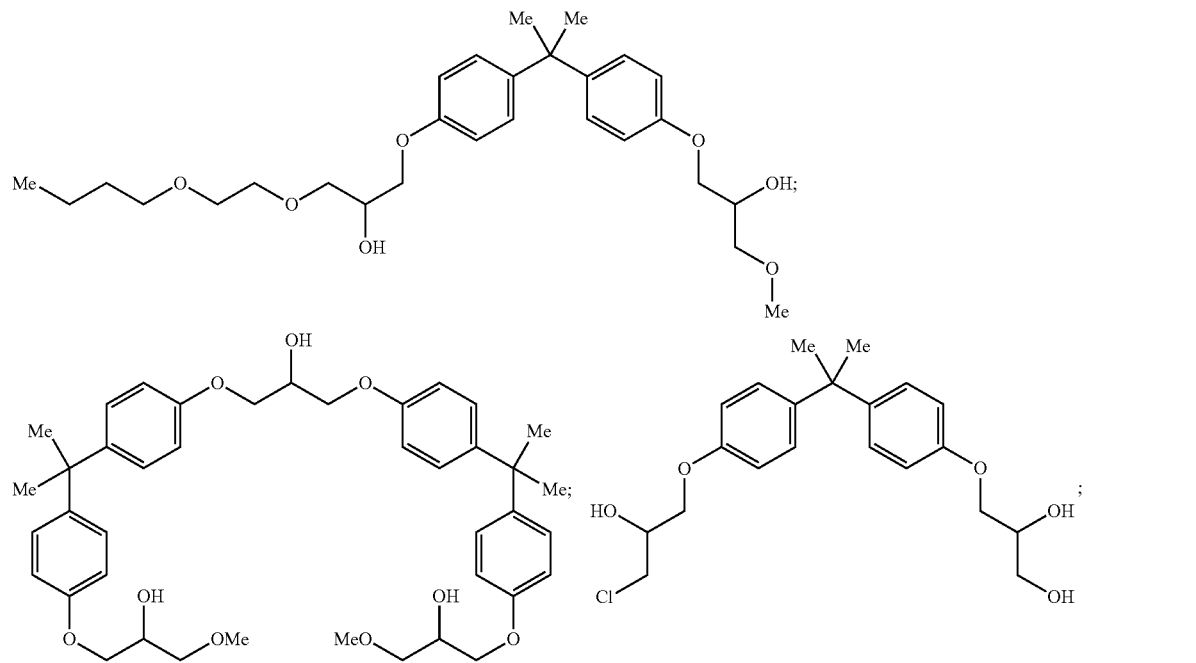
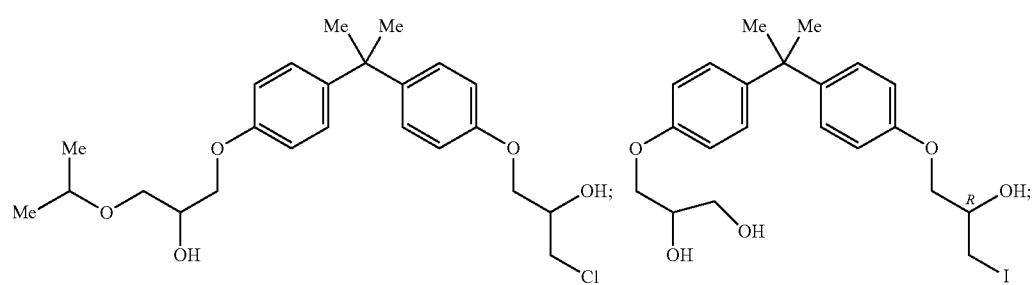
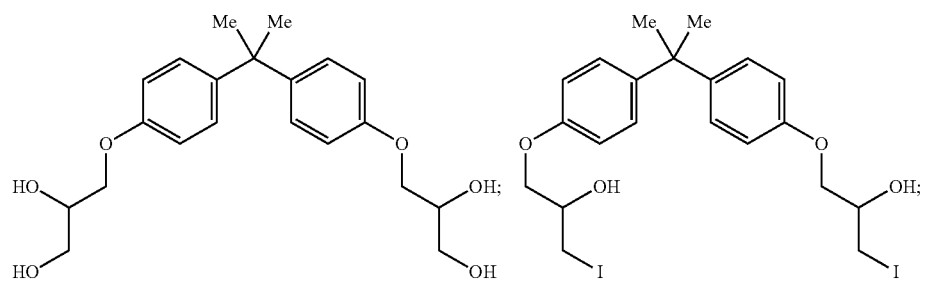

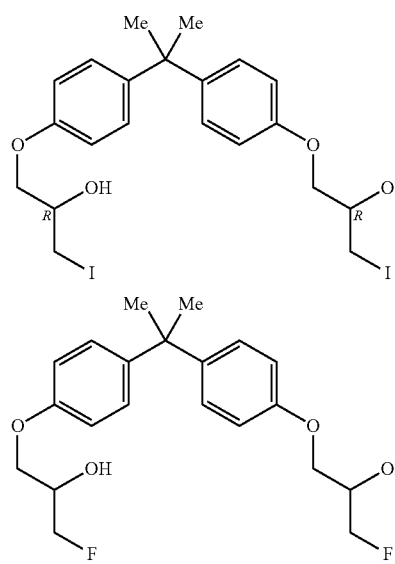
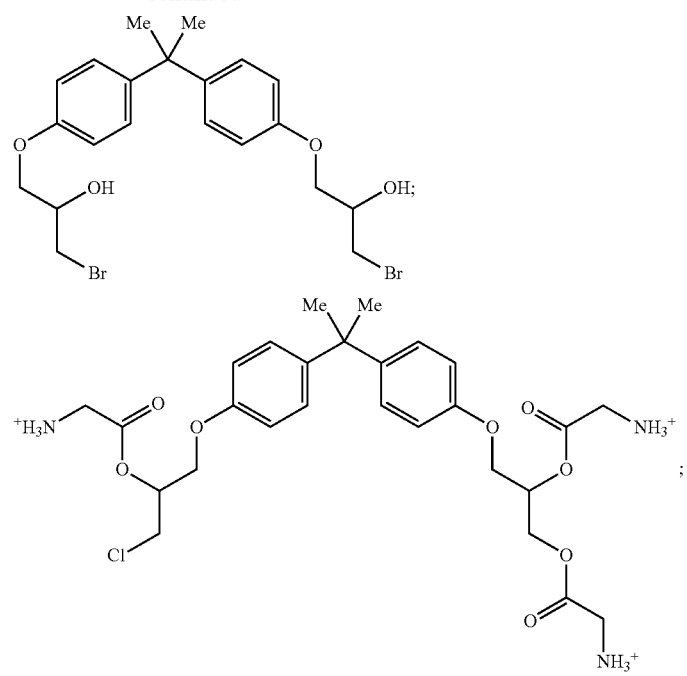
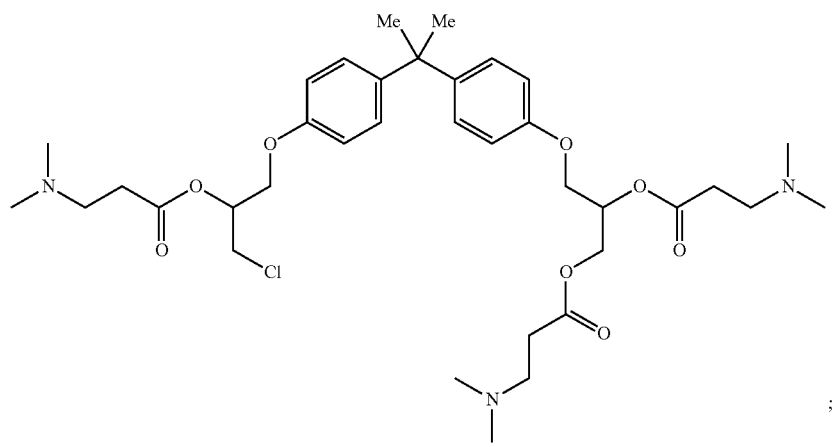
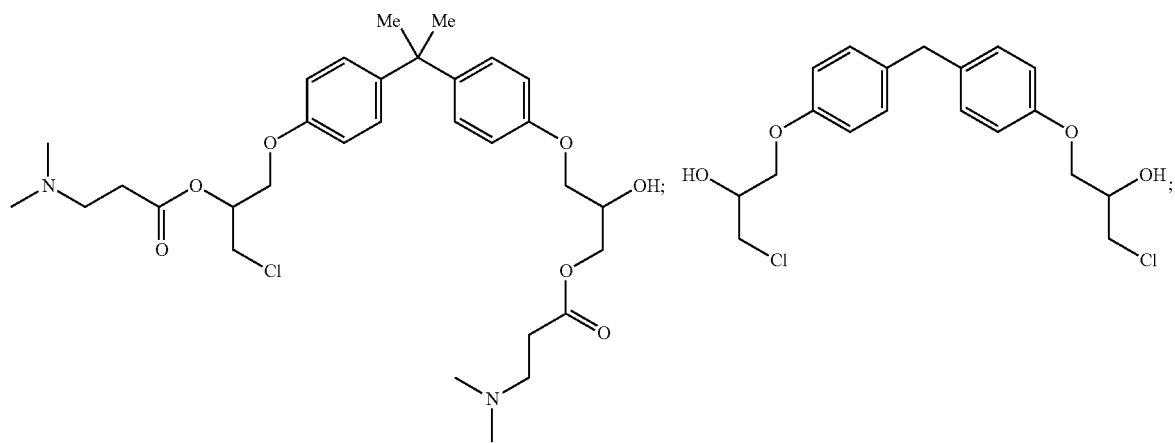

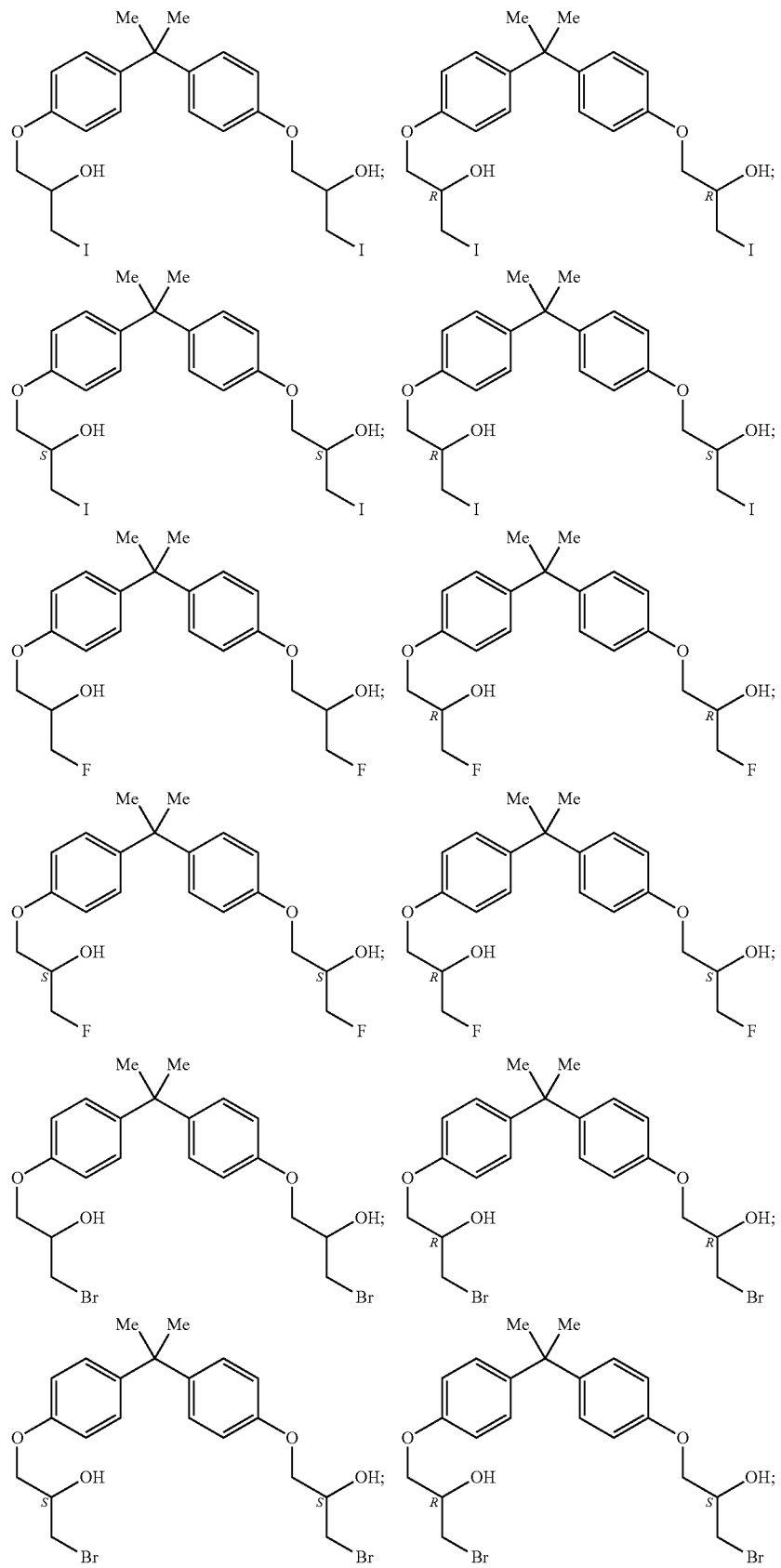

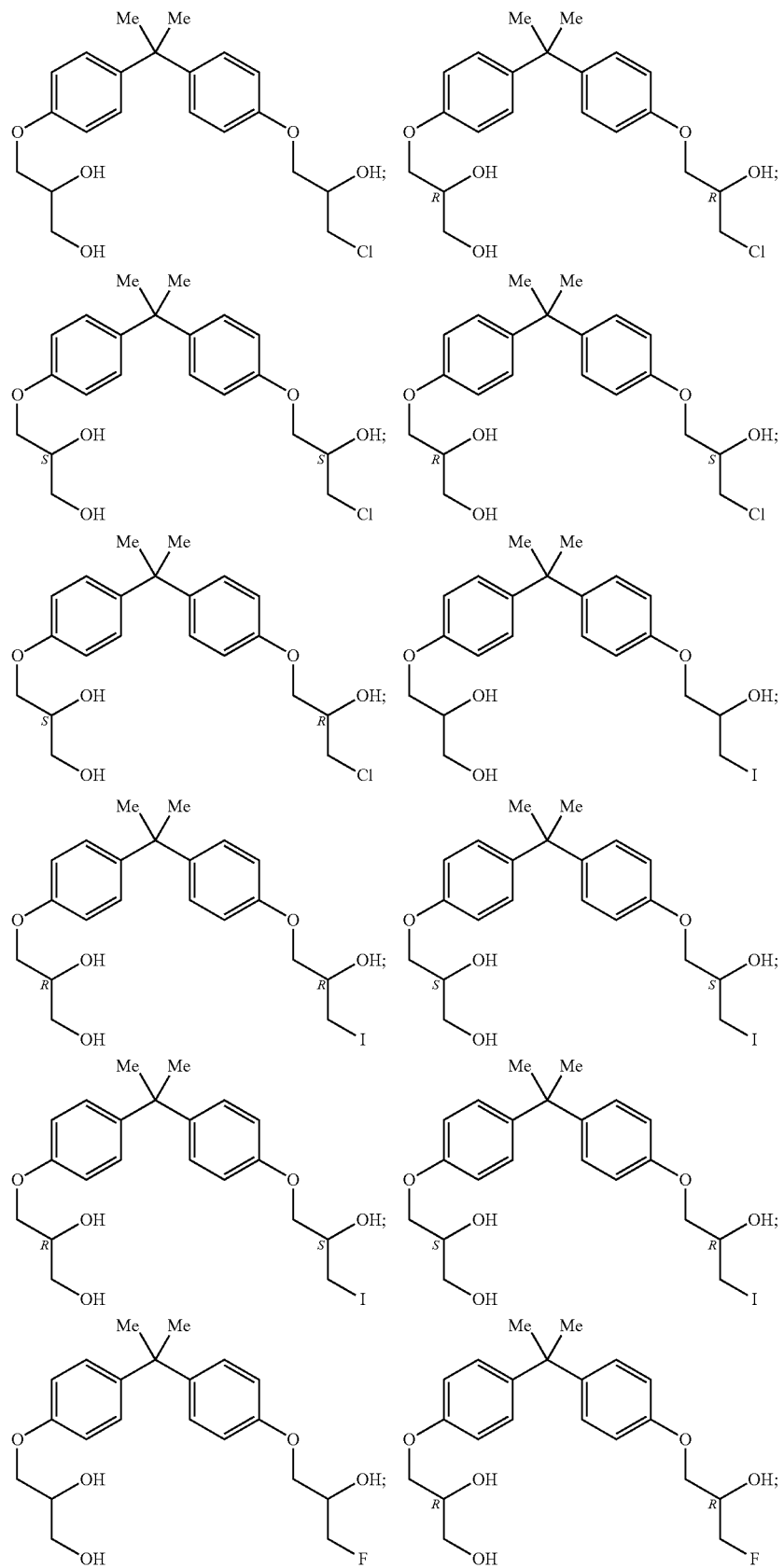

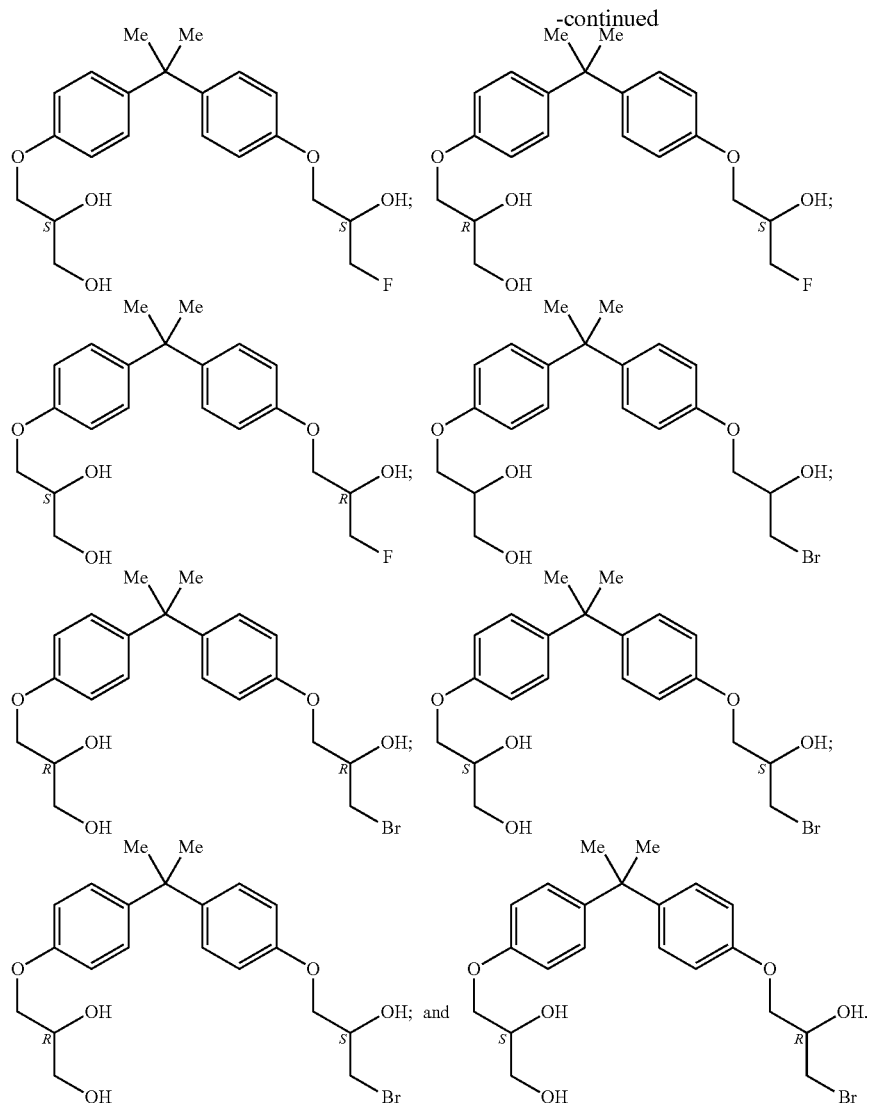

The compounds described herein are meant to include all racemic mixtures and all individual enantiomers or combinations thereof, whether or not they are represented herein. Alternatively, one or more of the OH groups may be substituted to replace the H with a moiety selected from TABLE 1.

In accordance with another embodiment, there is provided a compound having the formula:

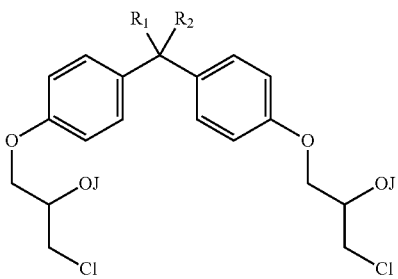

wherein, J may be a moiety selected from TABLE 1; $R^1$ and $R^2$ may each independently be H, or a branched, unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; and wherein an optional substituent if present may be selected from the group consisting of: oxo (i.e. =O), OJ''', COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R may be an unsubstituted $C_1$-$C_{10}$ alkyl.

Alternatively, J may be

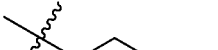

and $R^1$ and $R^2$ may each be selected from H and $CH_3$.

In accordance with another embodiment, there is provided a compound having one or more of the structures:

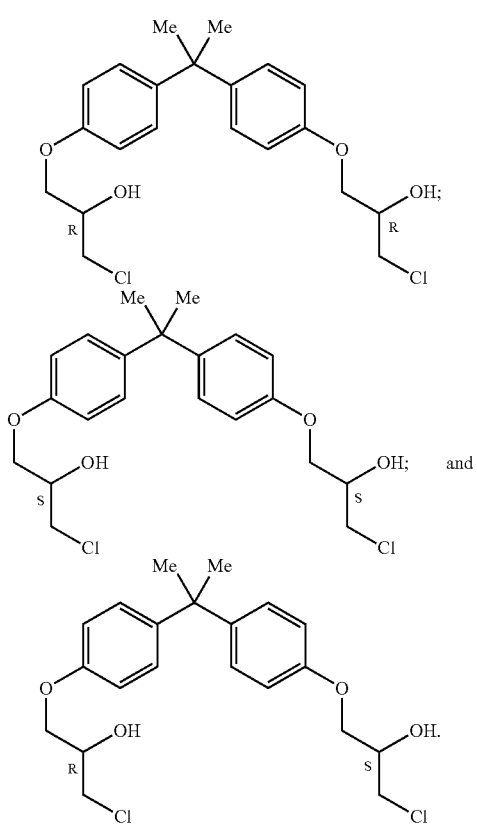

Alternatively, one or more of the OH groups of the above compounds may be substituted to replace the H with a moiety selected from TABLE 1.

In accordance with another embodiment, there are provided compounds having structures represented by Formula II

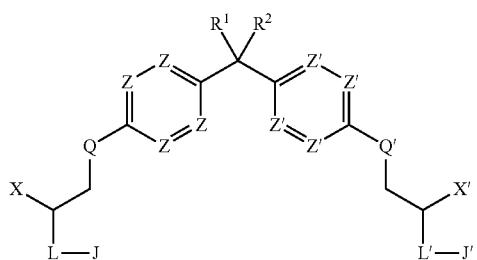

wherein each J and J' may independently be H or a moiety selected from TABLE 1; each L and L' may independently be O, S, NH, NG, N$^+$H$_2$ or N$^+$HG; each Q and Q' may independently be G, O, CH$_2$, CHG, CG$_2$, S, NH or NG; each Z and Z' may independently be N, CH, CF, CCl, CI, COH, CG, COG, CNH$_2$, CNHG, CNG$_2$, COSO$_3$H, COPO$_3$H$_2$; CSG, CSOG, or CSO$_2$G; R$^1$ and R$^2$ may each independently be H; or a branched or unbranched, substituted or unsubstituted C$_2$-C$_{10}$ alkyl or a substituted C$_1$ alkyl or together form a substituted or unsubstituted, saturated, aromatic cyclic or non-aromatic cyclic C$_3$-C$_{10}$ alkyl; X may be CH$_2$OG, CH$_2$OGOG', CH$_2$SG, CH$_2$NH$_2$, CH$_2$NHG, CH$_2$Cl, CH$_2$I, CH$_2$Br, CH$_2$F, or CH$_2$NG$_2$; X' may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$F, CHF$_2$, CF$_3$, CH$_2$OJ''', CH$_2$OG, CH$_2$OGOG', GOG', GOG'OG'', CH$_2$SG, CH$_2$NH$_2$, CH$_2$NHG, CH$_2$NG$_2$, or

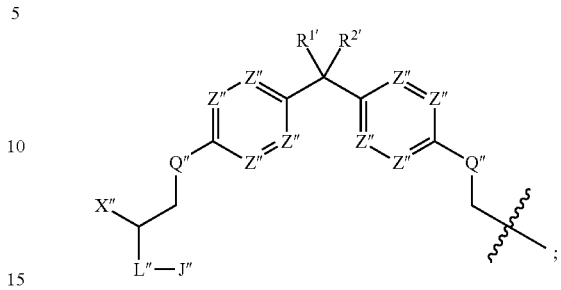

R$^{1'}$ and R$^{2'}$ may each independently be H, or a branched or unbranched, substituted or unsubstituted C$_1$-C$_{10}$ alkyl, or R$^{1'}$ and R$^{2'}$ together form a substituted or unsubstituted, saturated, aromatic cyclic or non-aromatic cyclic C$_3$-C$_{10}$ alkyl; each J'' and J''' may independently be H or a moiety selected from TABLE 1; L'' may be O, S, NH, NG, N$^+$H$_2$, or N$^+$HG; each Z'' may independently be N, CH, CF, CCl, CBr, CI, COH, CG, COG, CNH$_2$, CNHG, CNG$_2$, COSO$_3$H, COPO$_3$H$_2$; CSG, CSOG, or CSO$_2$G; Q'' may be G, O, CH$_2$, CHG, CG$_2$, S, NH or NG; X'' may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$OJ''', G, CH$_2$OG, CH$_2$OGOG', GOG', GOG'OG'', CH$_2$SG, CH$_2$NH$_2$, CH$_2$NHG, or CH$_2$NG$_2$; and each G, G', and G'' may independently be a branched or unbranched, non-aromatic cyclic, substituted or unsubstituted, saturated C$_1$-C$_{10}$ alkyl; wherein an optional substituent if present may be selected from the group consisting of: oxo (i.e. =O), OJ''', COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$ wherein R may be an unsubstituted C$_1$-C$_{10}$ alkyl.

Alternatively, each J and J' may independently be H or a moiety selected from TABLE 1; each L and L' may independently be O, S, NH, NG, N$^+$H$_2$ or N$^+$HG; each Q and Q' may independently be G, O, CH$_2$, CHG, CG$_2$, S, NH or NG; each Z and Z' may independently be N, CH, CF, CCl, CBr, CI, COH, CG, COG, CNH$_2$, CNHG, CNG$_2$, COSO$_3$H, COPO$_3$H$_2$; CSG, CSOG, or CSO$_2$G; R$^1$ and R$^2$ may each independently be H; or a branched or unbranched, substituted or unsubstituted C$_1$-C$_{10}$ alkyl or together form a substituted or unsubstituted, saturated, aromatic cyclic or non-aromatic cyclic C$_3$-C$_{10}$ alkyl; X may be CH$_2$OG, CH$_2$OGOG', CH$_2$SG, CH$_2$NH$_2$, CH$_2$NHG, CH$_2$I, CH$_2$Br, or CH$_2$F; X' may be H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$F, CHF$_2$, CF$_3$, CH$_2$OJ''', CH$_2$OG, CH$_2$OGOG', GOG', GOG'OG'', CH$_2$SG, CH$_2$NH$_2$, CH$_2$NHG, CH$_2$NG$_2$, or

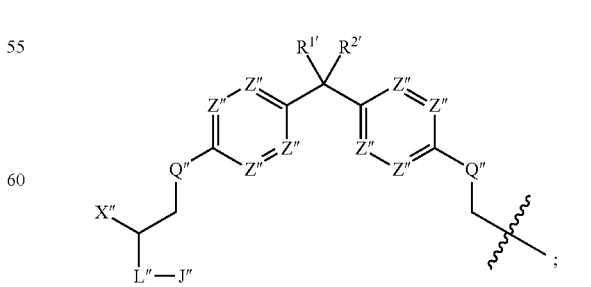

R$^{1'}$ and R$^{2'}$ may each independently be H, or a branched or unbranched, substituted or unsubstituted C$_1$-C$_{10}$ alkyl, or R$^{1'}$ and $R^{2'}$ together form a substituted or unsubstituted, saturated, aromatic cyclic or non-aromatic cyclic $C_3$-$C_{10}$ alkyl; each J" and J'" may independently be H or a moiety selected from TABLE 1; L" may be O, S, NH, NG, $N^+H_2$, or $N^+HG$; each Z" may independently be N, CH, CF, CCl, CBr, Cl, COH, CG, COG, $CNH_2$, CNHG, $CNG_2$, $COSO_3H$, $COPO_3H_2$; CSG, CSOG, or $CSO_2G$; Q" may be G, O, $CH_2$, CHG, $CG_2$, S, NH or NG; X" may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2OJ'''$, G, $CH_2OG$, $CH_2OGOG'$, GOG', GOG'OG", $CH_2SG$, $CH_2NH_2$, $CH_2NHG$, or $CH_2NG_2$; and each G, G', and G" may independently be a branched or unbranched, non-aromatic cyclic, substituted or unsubstituted, saturated $C_1$-$C_{10}$ alkyl; wherein an optional substituent if present may be selected from the group consisting of: oxo (i.e. =O), OJ'", COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R may be an unsubstituted $C_1$-$C_{10}$ alkyl.

In accordance with another embodiment, there is provided a pharmaceutical composition comprising a compound according to any one of the above compounds and a pharmaceutically acceptable excipient.

In accordance with a further embodiment, there is provided a method of screening for androgen receptor modulating compounds, wherein the compounds screened are selected from compounds having the Formula III:

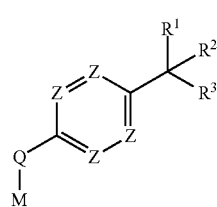

III wherein, Q may be G, O, $CH_2$, CHG, $CG_2$, S, NH or NG; each Z may independently be N, CH, CF, CCl, CBr, Cl, COH, CG, COG, $CNH_2$, CNHG, $CNG_2$, $COSO_3H$, $COPO_3H_2$; CSG, CSOG, or $CSO_2G$; $R^1$ and $R^2$ may each independently be H, or a branched or unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; each G G' and G" may independently be a branched, unbranched, or aromatic cyclic or non-aromatic cyclic, substituted or unsubstituted, saturated or unsaturated $C_1$-$C_{10}$ alkyl; M may be selected from the following:

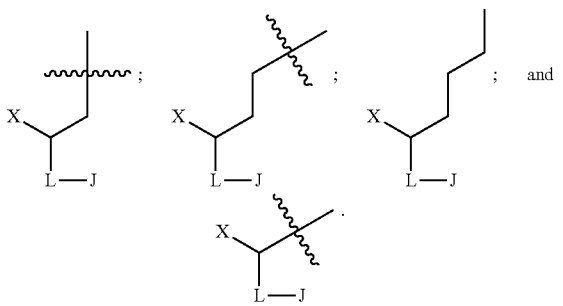

wherein J may be H or a moiety may be selected from TABLE 1; L may be O, S, NH, NG, $N^+H_2$, or $N^+HG$; X may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2OJ'''$, G, $CH_2OG$, $CH_2OGOG'$, GOG', GOG'OG", $CH_2SG$, $CH_2NH_2$, $CH_2NHG$, or $CH_2NG_2$;

$R^3$ may be H, a branched, unbranched, substituted or unsubstituted $C_1$-$C_{10}$ alkyl,

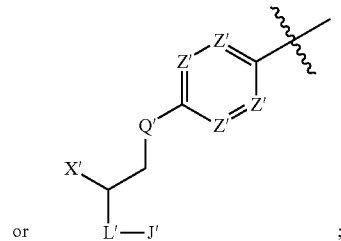

or

J' may be H or a moiety selected from TABLE 1; L' may be O, S, NH, NG, $N^+H_2$, or $N^+HG$; each Z' may independently be N, CH, CF, CCl, CBr, Cl, COH, CG, COG, $CNH_2$, CNHG, $CNG_2$, $COSO_3H$, $COPO_3H_2$; CSG, CSOG, or $CSO_2G$; Q' may be G, O, $CH_2$, CHG, $CG_2$, S, NH or NG; X' may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2OJ'''$, G, $CH_2OG$, $CH_2OGOG'$, GOG', GOG'OG", $CH_2SG$, $CH_2NH_2$, $CH_2NHG$, or

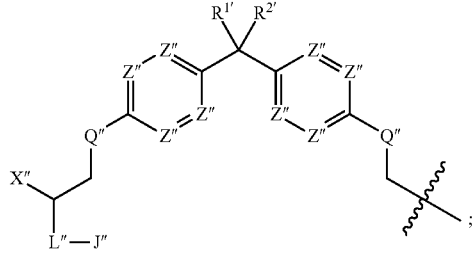

$R^{1'}$ and $R^{2'}$ may each independently be H, or a branched, unbranched, substituted or unsubstituted $C_1$-$C_{10}$ alkyl or together form a substituted or unsubstituted, saturated, aromatic cyclic or non-aromatic cyclic $C_3$-$C_{10}$ alkyl; each J" and J'" may independently be H or a moiety selected from TABLE 1; L" may be O, S, NH, NG, $N^+H_2$, or $N^+HG$; each Z" may independently be N, CH, CF, CCl, CBr, Cl, COH, CG, COG, $CNH_2$, CNHG, $CNG_2$, $COSO_3H$, $COPO_3H_2$; CSG, CSOG, or $CSO_2G$; Q" may be G, O, $CH_2$, CHG, $CG_2$, S, NH or NG; and X" may be H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, $CH_2OJ'''$, G, $CH_2OG$, $CH_2OGOG'$, GOG', GOG'OG", $CH_2SG$, $CH_2NH_2$, $CH_2NHG$, or $CH_2NG_2$; wherein an optional substituent if present may be selected from the group consisting of: oxo (i.e. =O), OJ'", COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R may be an unsubstituted $C_1$-$C_{10}$ alkyl.

BRIEF DESCRIPTION OF THE DRAWINGS

FIG. 6 185-9-2 (5 μg/ml) inhibited AR transcriptional activity in response to ligand as measured using the PSA(6.1 kb)-luciferase reporter gene construct that contains numerous well-characterized and functional androgen response elements (AREs). Bicalutamide (BIC, 10 μM) was included as a positive control. 185-9-2 does NOT inhibit the activity of progesterone response element (PRE)-luciferase reporter or glucocorticoid response element (GRE)-luciferase reporter in LNCaP cells that were transfected with expression vectors for progesterone receptor (PR) and glucocorticoid receptor (GR) and their relevant reporter gene constructs (PRE-luc or GRE-luc) and exposed to their respective steroid (10 nM, black bars). White bars represent no steroid (ethanol control).

FIG. 9 AR in whole cell lysates from LNCaP cells maintained in vitro for 48 hrs with 185-9-2 (B2) in the presence or absence of DHT. Results are from 3 separate experiments.

DETAILED DESCRIPTION

Figure 1:
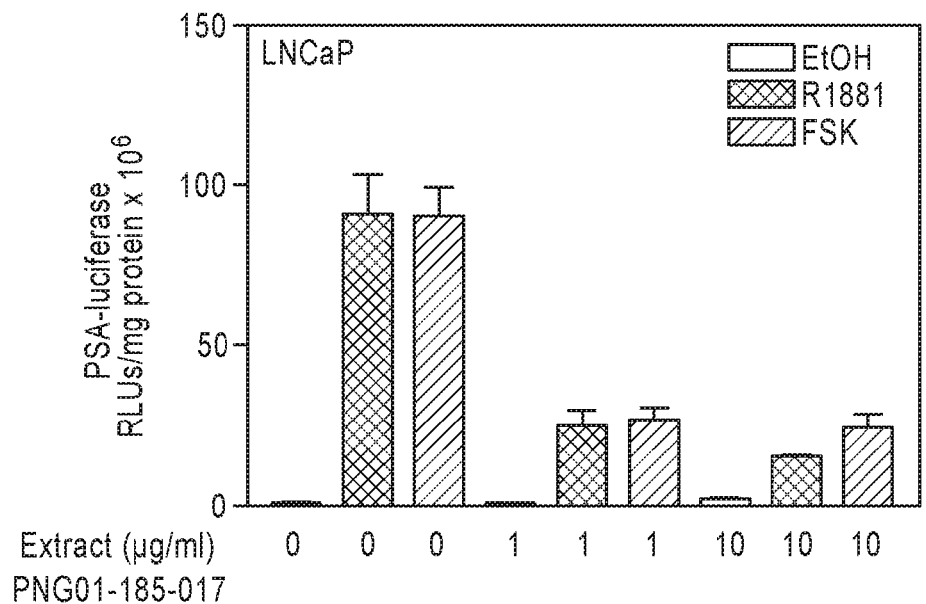
FIG. 1 shows that extract PNG 01-185 blocked induction of PSA-luciferase (PSA-luc) activity by forskolin (FSK, 50 µM) and R1881 (1 nM).

As used herein, the phrase "$C_x$-$C_y$ alkyl" is used as it is normally understood to a person of skill in the art and often refers to a chemical entity that has a carbon skeleton or main carbon chain comprising a number from x to y (with all individual integers within the range included, including integers x and y) of carbon atoms. For example a "$C_1$-$C_{10}$ alkyl" is a chemical entity that has 1, 2, 3, 4, 5, 6, 7, 8, 9 or 10 carbon atom(s) in its carbon skeleton or main chain.

As used herein, the term "cyclic $C_x$-$C_y$ alkyl" is used as it is normally understood to a person of skill in the art and often refers to a compound or a chemical entity in which at least a portion of the carbon skeleton or main chain of the chemical entity is bonded in such a way so as to form a 'loop', circle or ring of atoms that are bonded together. The atoms do not have to all be directly bonded to each other, but rather may be directly bonded to as few as two other atoms in the 'loop'. Non-limiting examples of cyclic alkyls include benzene, toluene, cyclopentane, bisphenol and 1-chloro-3-ethylcyclohexane.

As used herein, the term "branched" is used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl are tert-butyl and isopropyl.

As used herein, the term "unbranched" is used as it is normally understood to a person of skill in the art and often refers to a chemical entity that comprises a skeleton or main chain that does not split off into more that one contiguous chain. Non-limiting examples of unbranched alkyls are methyl, ethyl, n-propyl, and n-butyl.

As used herein, the term "substituted" is used as it is normally understood to a person of skill in the art and often refers to a chemical entity that has one chemical group replaced with a different chemical group that contains one or more heteroatoms. Unless otherwise specified, a substituted alkyl is an alkyl in which one or more hydrogen atom(s) is/are replaced with one or more atom(s) that is/are not hydrogen(s). For example, chloromethyl is a non-limiting example of a substituted alkyl, more particularly an example of a substituted methyl Aminoethyl is another non-limiting example of a substituted alkyl, more particularly it is a substituted ethyl.

As used herein, the term "unsubstituted" is used as it is normally understood to a person of skill in the art and often refers to a chemical entity that is a hydrocarbon and/or does not contain a heteroatom. Non-limiting examples of unsubstituted alkyls include methyl, ethyl, tert-butyl, and pentyl.

As used herein, the term "saturated" when referring to a chemical entity is used as it is normally understood to a person of skill in the art and often refers to a chemical entity that comprises only single bonds. Non-limiting examples of saturated chemical entities include ethane, tert-butyl, and $N^+H_3$.

As used herein, $C_1$-$C_{10}$ alkyl may include, for example, and without limitation, saturated $C_1$-$C_{10}$ alkyl, $C_2$-$C_{10}$ alkenyl and $C_2$-$C_{10}$ alkynyl. Non-limiting examples of saturated $C_1$-$C_{10}$ alkyl may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{10}$ alkenyl may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{10}$ alkynyl may include ethynyl, propynyl, butynyl, pentynyl, hexynyl, heptynyl, octynyl, nonynyl and decynyl. Saturated $C_1$-$C_{10}$ alkyl, $C_2$-$C_{10}$ alkenyl or $C_2$-$C_{10}$ alkynyl may be, for example, and without limitation, interrupted by one or more heteroatoms which are independently nitrogen, sulfur or oxygen.

As used herein, cyclic $C_3$-$C_{10}$ alkyl may include, for example, and without limitation, saturated $C_3$-$C_{10}$ cycloalkyl, $C_3$-$C_{10}$ cycloalkenyl, $C_3$-$C_{10}$ cycloalkynyl, $C_{6-10}$ aryl, $C_{6-9}$ aryl-$C_{1-4}$ alkyl, $C_{6-8}$ aryl-$C_{2-4}$ alkenyl, $C_{6-8}$ aryl-$C_{2-4}$ alkynyl, a 4- to 10-membered non-aromatic heterocyclic group containing one or more heteroatoms which are independently nitrogen, sulfur or oxygen, and a 5- to 10-membered aromatic heterocyclic group containing one or more heteroatoms which are independently nitrogen, sulfur or oxygen. Non-limiting examples of the saturated $C_3$-$C_{10}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{10}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of the $C_6$-$C_{10}$ aryl group may include phenyl (Ph), pentalenyl, indenyl, naphthyl, and azulenyl. The $C_{6-9}$ aryl-$C_{1-4}$ alkyl group may be, for example, and without limitation, a $C_{1-4}$ alkyl group as defined anywhere above having a $C_{6-9}$ aryl group as defined anywhere above as a substituent. The $C_{6-8}$ aryl-$C_{2-4}$ alkenyl group may be, for example, and without limitation, a $C_{2-4}$ alkenyl as defined anywhere above having a $C_{6-8}$ aryl group as defined anywhere above as a substituent. The $C_{6-8}$ aryl-$C_{2-4}$ alkynyl group may be, for example, and without limitation, a $C_{2-4}$ alkynyl group as defined anywhere above having a $C_{6-8}$ aryl group as defined anywhere above as a substituent. Non-limiting examples of the 4- to 10-membered non-aromatic heterocyclic group containing one or more heteroatoms which are independently nitrogen, sulfur or oxygen may include pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide and succinimide. Non-limiting examples of the 5- to 10-membered aromatic heterocyclic group containing one or more heteroatoms which are independently nitrogen, sulfur or oxygen may include pyrrolyl, pyridinyl, pyridazinyl, pyrimidinyl, pirazinyl, imidazolyl, thiazolyl and oxazolyl.

Each of $C_1$-$C_{10}$ alkyl and cyclic $C_3$-$C_{10}$ alkyl may be unsubstituted or substituted with one or more substituents independently selected from the group consisting of: oxo (=O), OJ''', COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R is an unsubstituted $C_1$-$C_{10}$ alkyl. Furthermore, the one or more substituents may be independently selected from the group consisting of: oxo (=O), OJ''', COOH, OH, F, Cl, Br, I, $NH_2$, SH, $SO_3H$, and $NO_2$. Furthermore, the one or more substituents may be independently selected from the group consisting of: oxo (=O), OJ''', COOH, OH, F, Cl, Br, and I. Furthermore, the one or more substituents may be independently selected from the group consisting of: oxo (=O), OH, F, Cl, Br, and I. Furthermore, the one or more substituents may be independently selected from the group consisting of: oxo (=O), and OH. Furthermore, R may be an unsubstituted $C_1$-$C_5$ alkyl. Each of $C_1$-$C_{10}$ alkyl and cyclic $C_3$-$C_{10}$ alkyl may be substituted with, for example, and without limitation, 1, 2, 3, 4, 5, or 6 substituents.

As used herein, the symbol

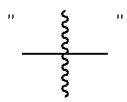

(hereinafter may be referred to as "a point of attachment bond") denotes a bond that is a point of attachment between two chemical entities, one of which is depicted as being attached to the point of attachment bond and the other of which is not depicted as being attached to the point of attachment bond. For example,

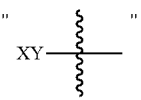

indicates that the chemical entity "XY" is bonded to another chemical entity via the point of attachment bond. Furthermore, the specific point of attachment to the non-depicted chemical entity may be specified by inference. For example The compound $CH_3$—$R^3$, wherein $R^3$ is H or

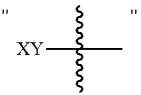

infers that when $R^3$ is "XY", the point of attachment bond is the same bond as the bond by which $R^3$ is depicted as being bonded to $CH_3$.

As used herein, the term "moiety" refers to a moiety set out in the following Table 1.

TABLE 1

MOIETIES

Amino Acid Based Moieties

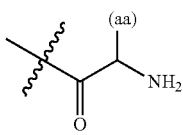 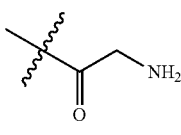 [SMILES: *C(=O)CN] 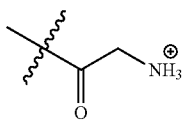 [SMILES: *C(=O)C[NH3+]] 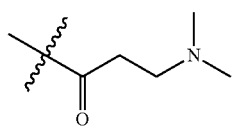 [SMILES: *C(=O)CCN(C)C]

(aa) = any naturally occurring amino acid side chain

Polyethylene Glycol Based Moieties

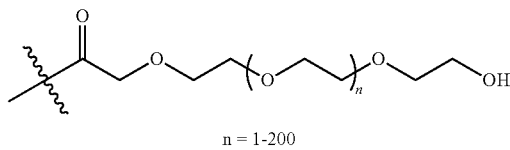

n = 1-200

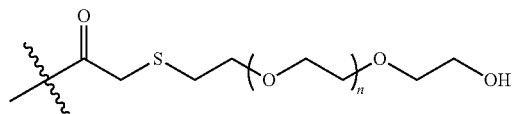

n = 1-200

Phosphate Based Moieties

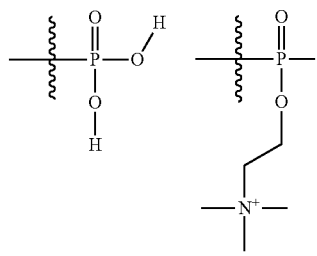 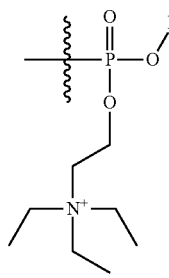 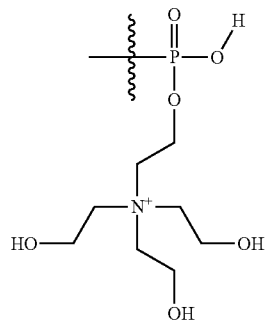 [SMILES: *P(=O)(O)OCC[N+](CCO)(CCO)CCO] 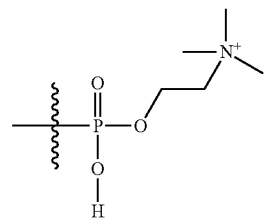 [SMILES: *P(=O)(O)OCC[N+](C)(C)C]

TABLE 1-continued
MOIETIES
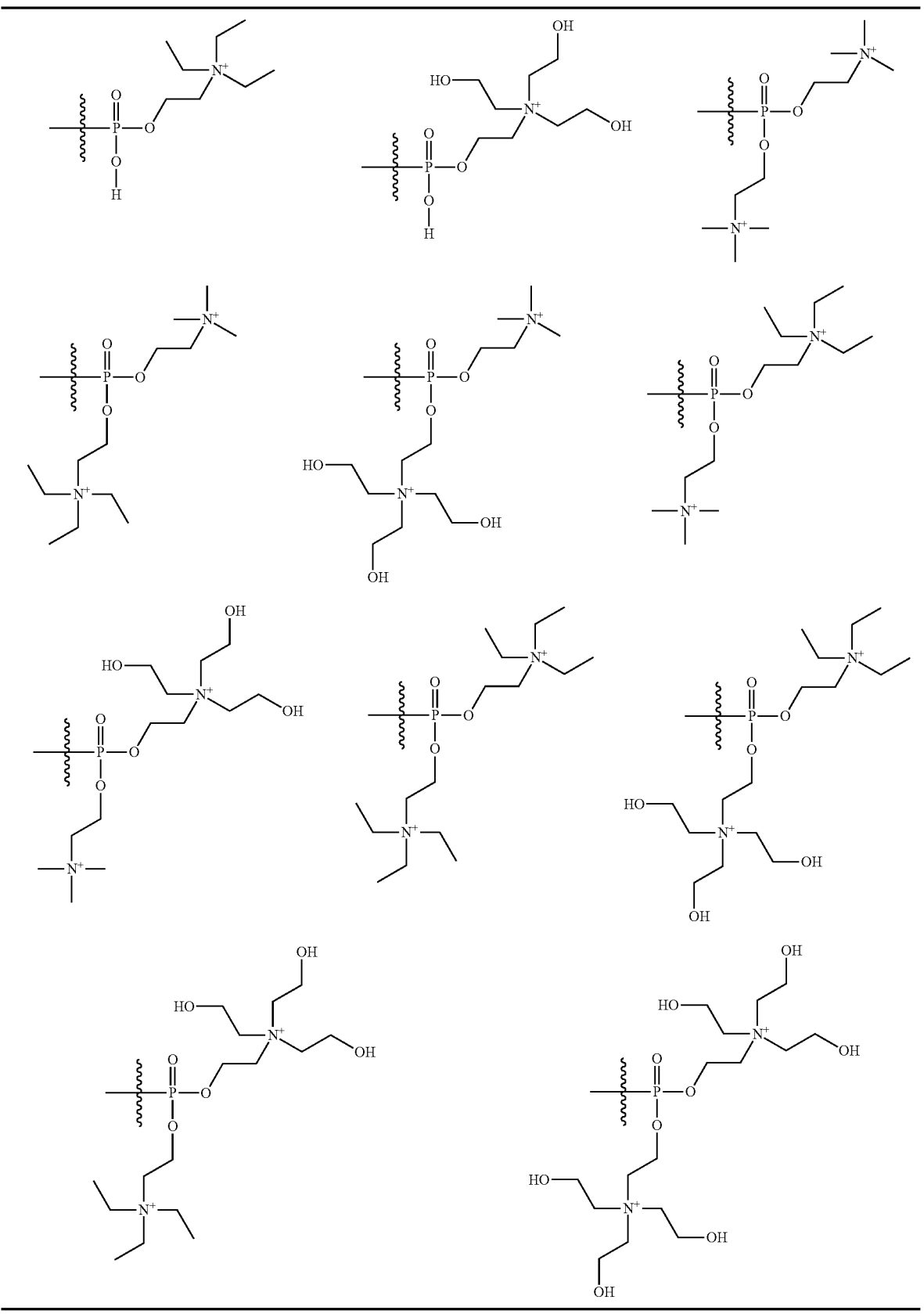

Moieties may be, for example, and without limitation, subdivided into three groups: 1) amino acid based moieties; 2) polyethylene glycol based moieties; and 3) phosphate based moieties. In the Moieties Table 1 above, the first four moieties are amino acid based moieties, the fifth and sixth are polyethylene glycol based moieties and the remaining moieties are phosphate based moieties.

The amino acid side chains of naturally occurring amino acids (as often denoted herein using "(aa)") are well known to a person of skill in the art and may be found in a variety of text books such as "Molecular Cell Biology" by James Darnell et al. Third Edition, published by Scientific American Books in 1995. Often the naturally occurring amino acids are represented by the formula $(NH_2)C(COOH)(H)(R)$, where the chemical groups in brackets are each bonded to the carbon not in brackets. R represents the side chains in this particular formula.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In other particular embodiments of Formula I and Formula II above, the following compounds in Table 2 are provided:

TABLE 2

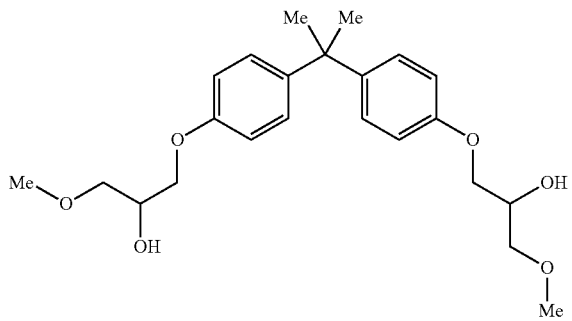

Sponge Extract:
PNG01-185-017-2

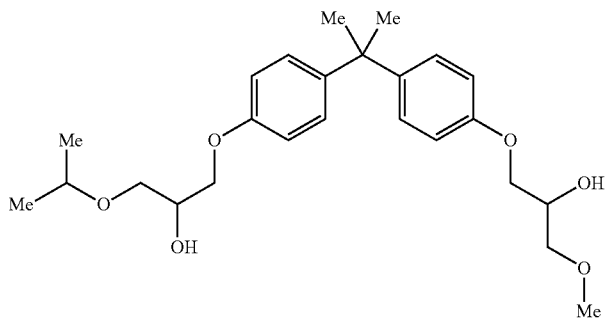

Sponge Extract:
PNG01-185-017-5

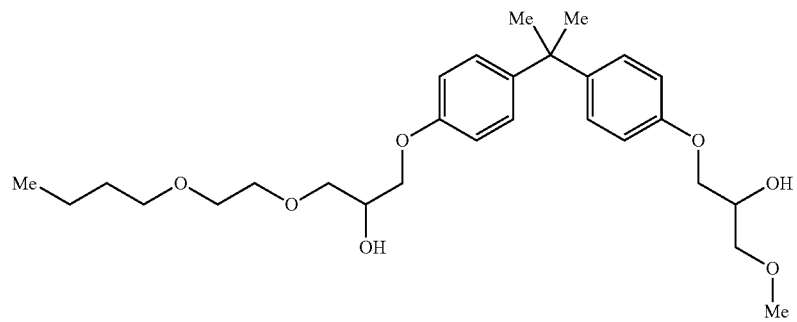

Sponge Extract:
PNG01-185-017-6

TABLE 2-continued
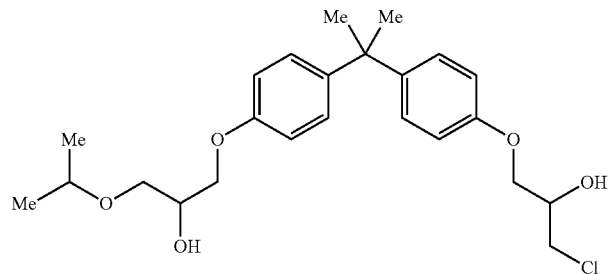
Sponge Extract:
PNG01-185-017-7
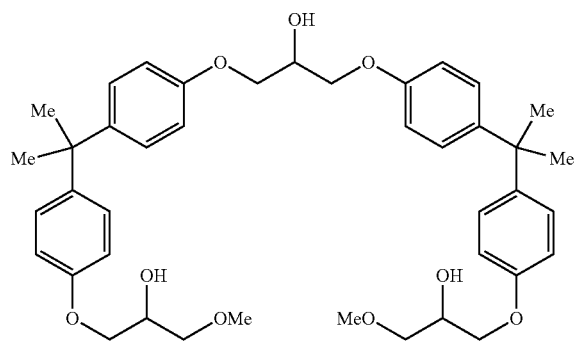
Sponge Extract:
PNG01-185-017-8
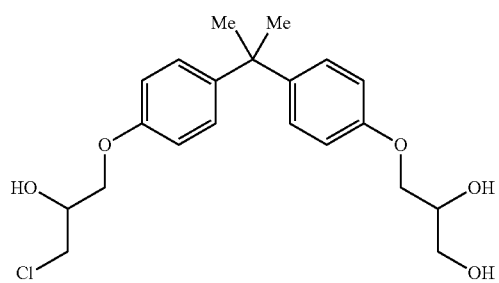
Sponge Extract:
PNG01-185-017-9-2
PNG01-185-17-9-2
185-9-2
B2
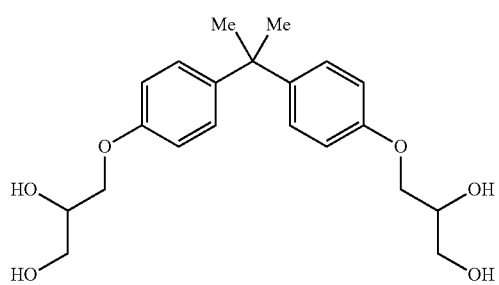
PNG01-185-017-9-1
PNG01-185-17-9-1
185-9-1

TABLE 2-continued
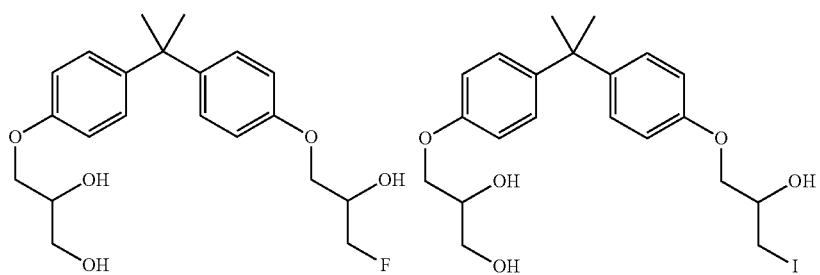
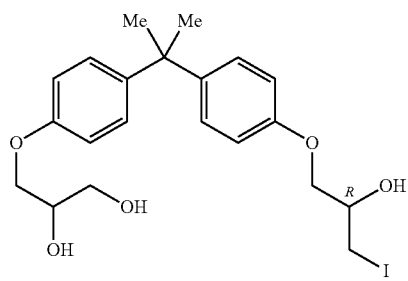
(R)-BADGE x HI x H₂O
(2-R) Isomers BADGE x HI x H₂O
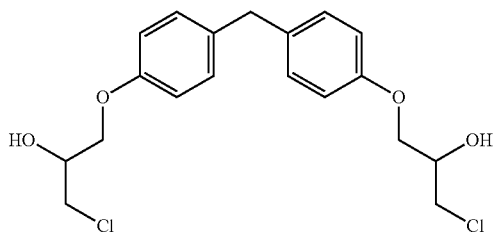 [SMILES: OC(CCl)COc1ccc(Cc2ccc(OCC(O)CCl)cc2)cc1]
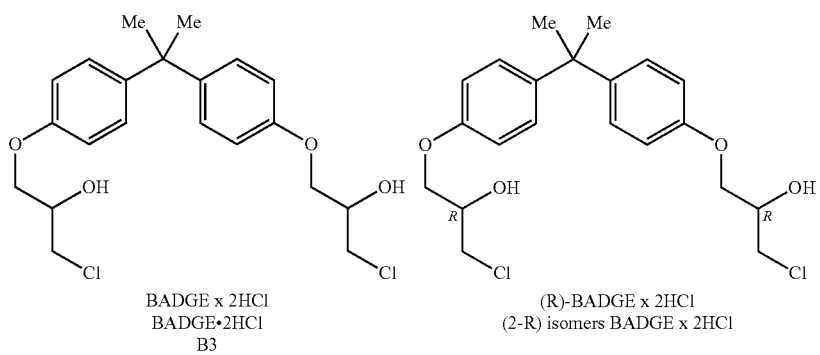
BADGE x 2HCl
BADGE·2HCl
B3
(R)-BADGE x 2HCl
(2-R) isomers BADGE x 2HCl
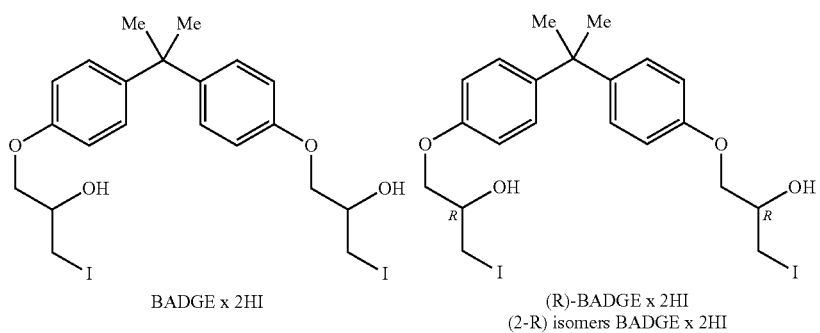
BADGE x 2HI
(R)-BADGE x 2HI
(2-R) isomers BADGE x 2HI TABLE 2-continued
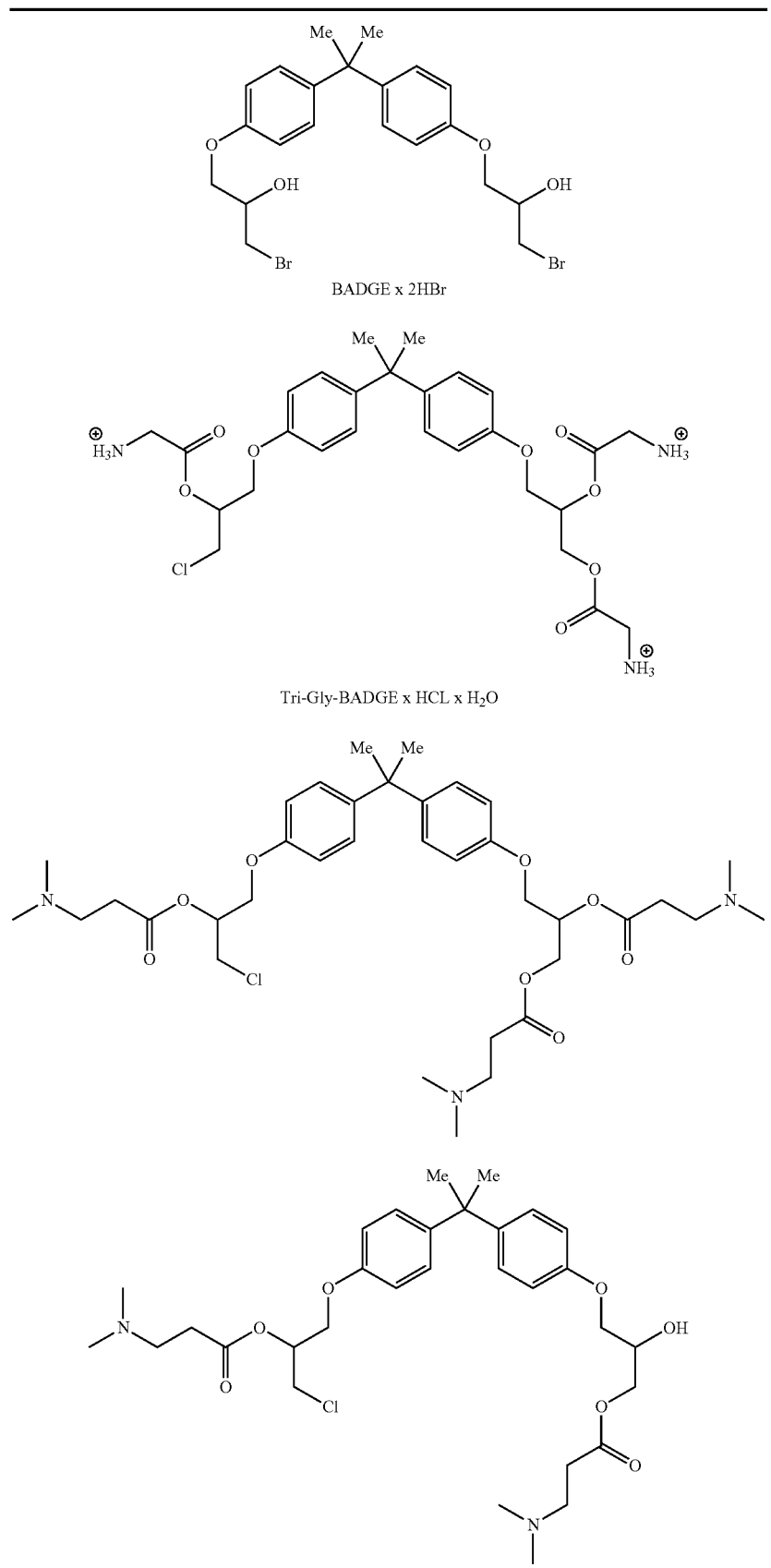

TABLE 2-continued
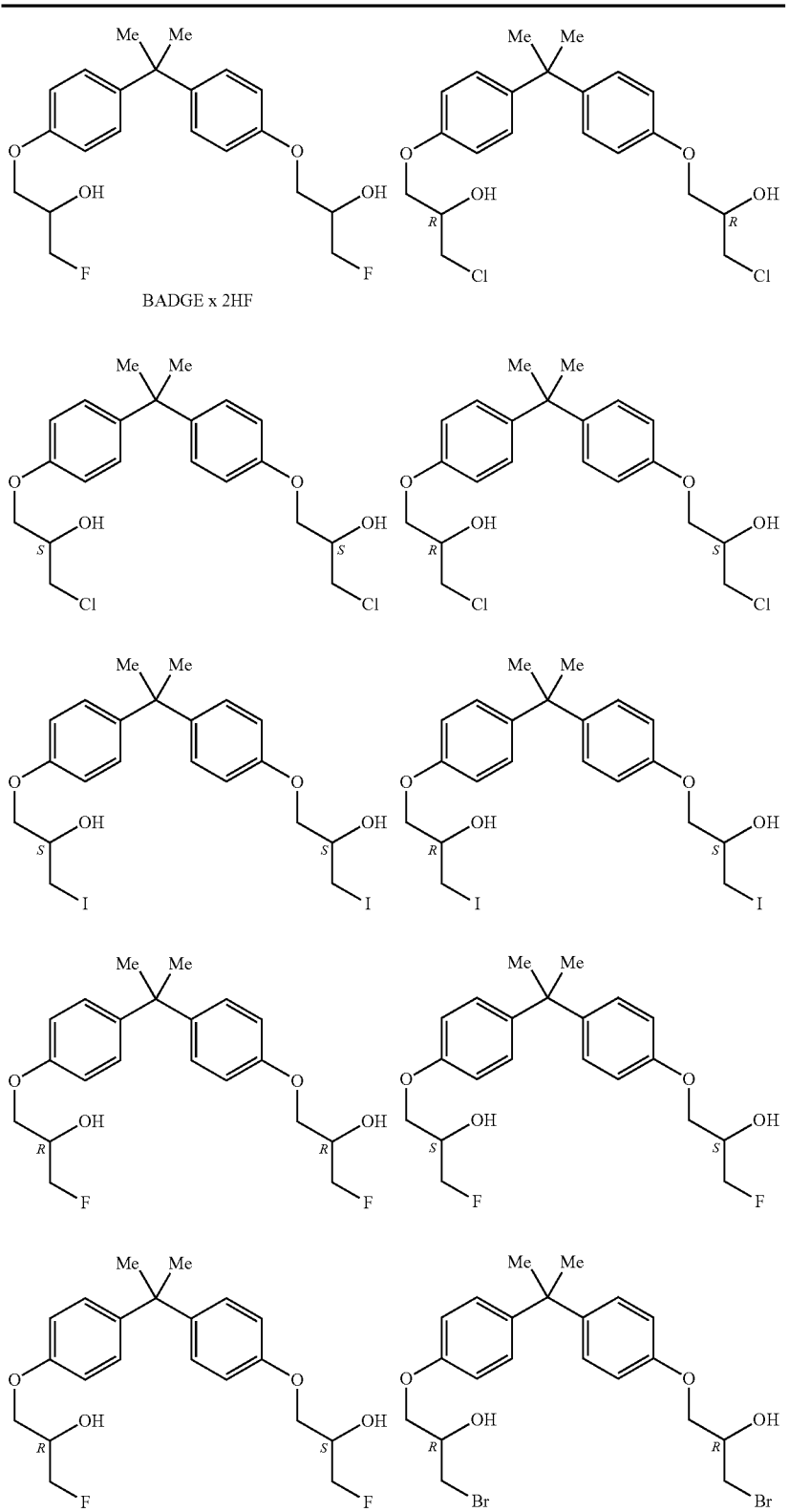
BADGE x 2HF

TABLE 2-continued
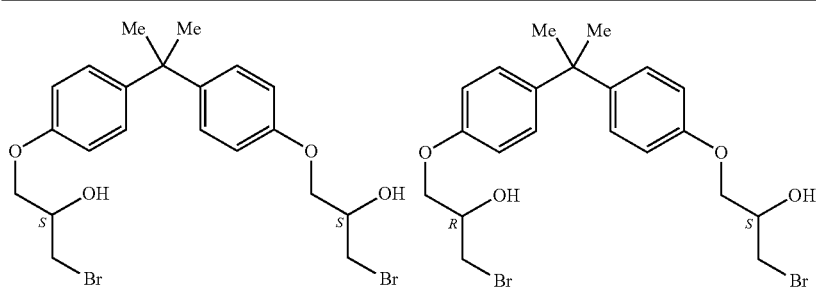
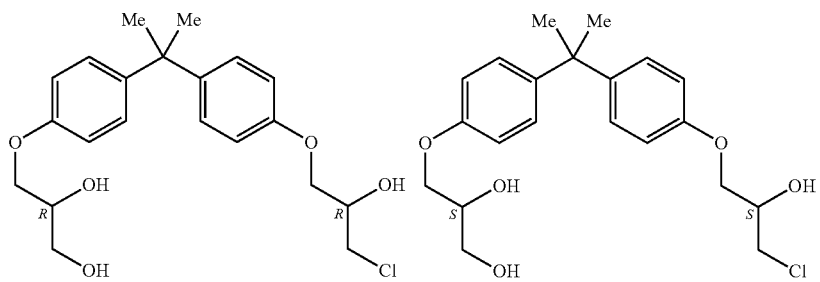
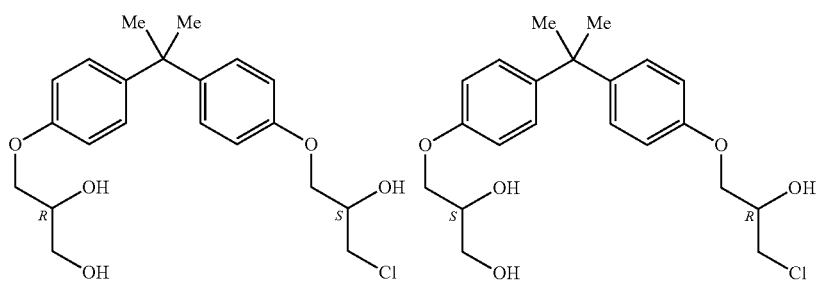
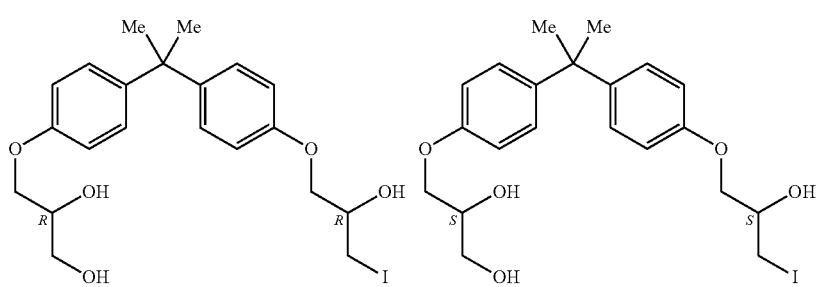
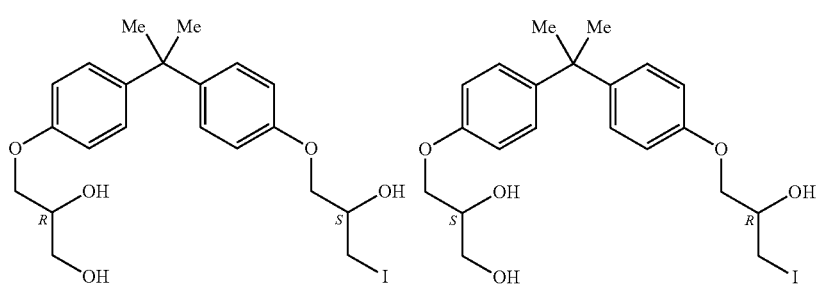

TABLE 2-continued
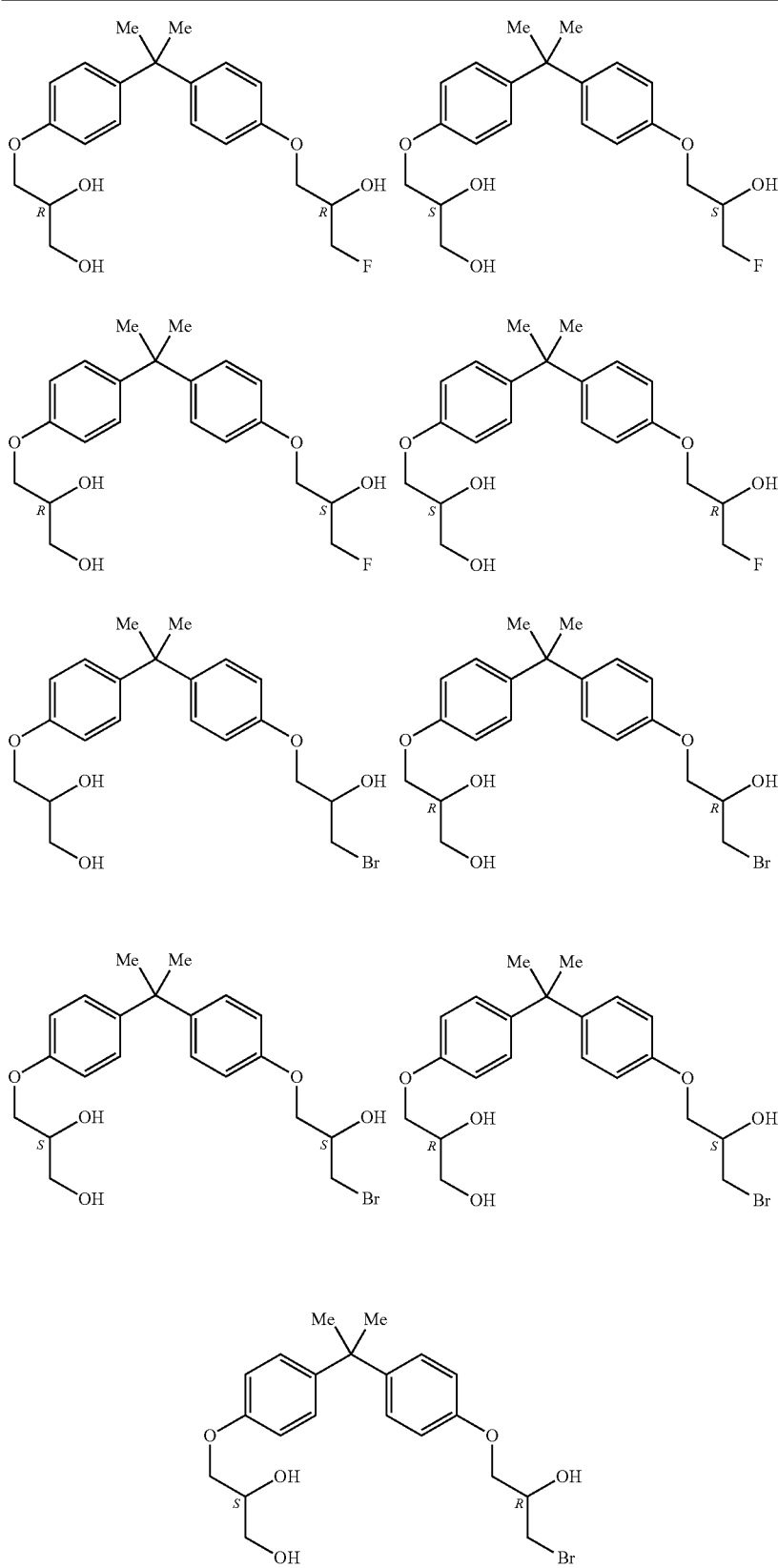

Methods of preparing or synthesizing compounds of the present invention may also be understood by a person of skill in the art having reference to known chemical synthesis principles. For example, Auzou et al 1974 *European Journal of Medicinal Chemistry* 9(5), 548-554 describes suitable synthetic procedures that may be considered and suitably adapted for preparing compounds of Formula I or Formula II. Other references that may be helpful in the preparation of compounds of Formula I or Formula II include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

The chemical preparation of compounds of Formula I and Formula II is described below in the Examples and by the following non-limiting exemplary synthetic scheme.

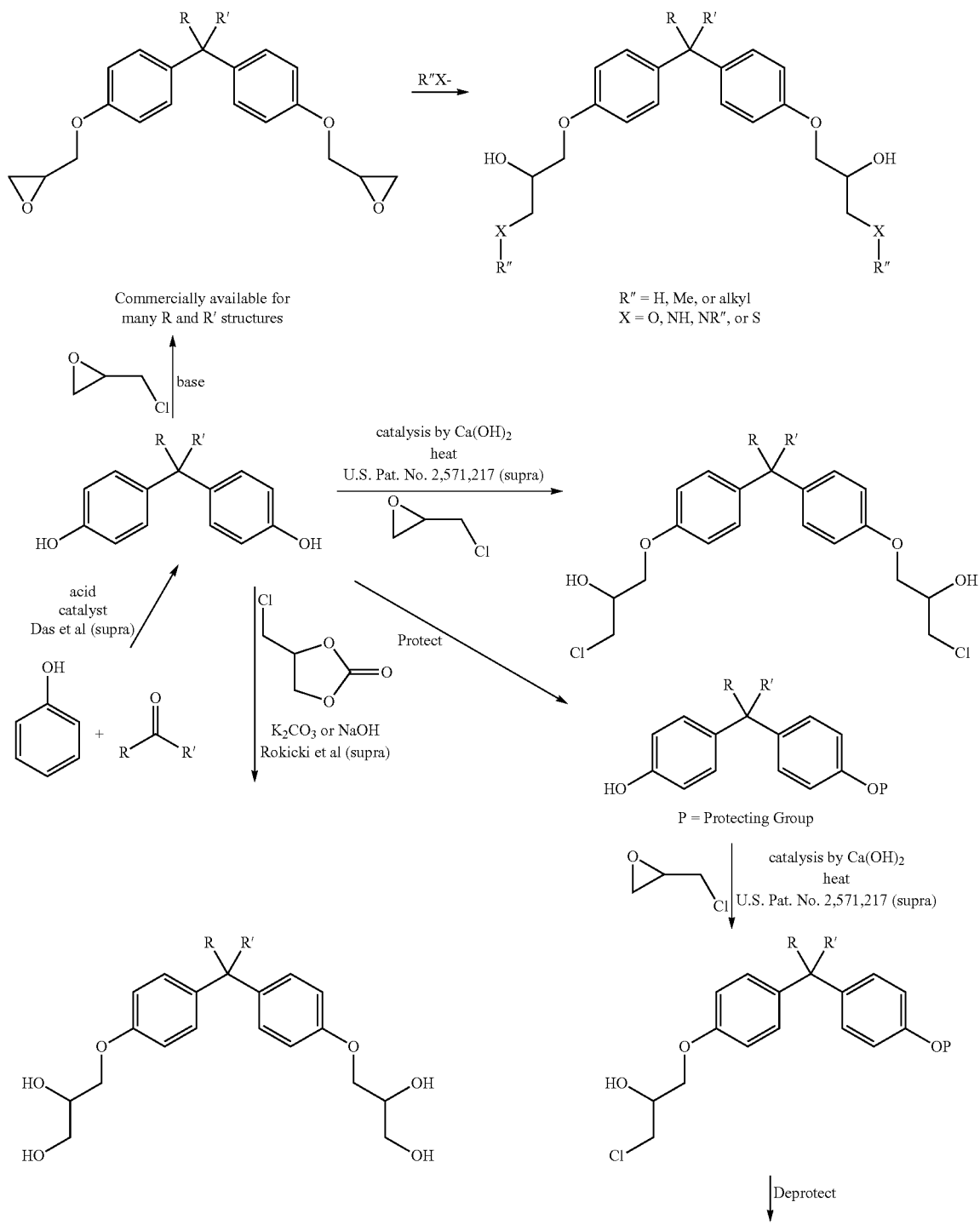

61
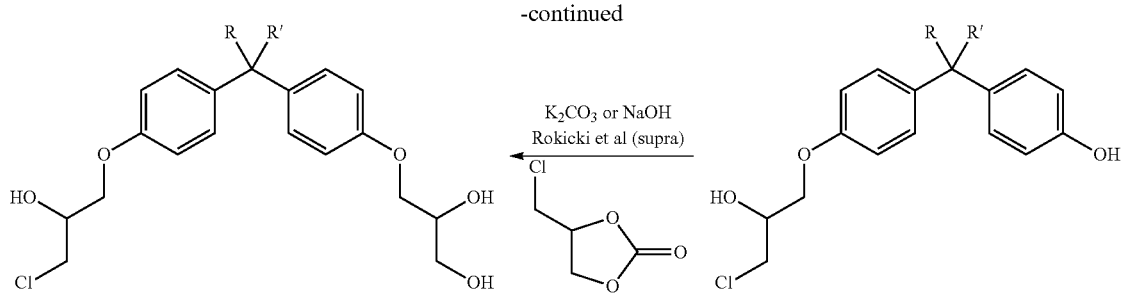
-continued
62
In the above scheme R and R' may be, for example, and without limitation, independently selected from the group consisting of H, Me or alkyl.
Compounds falling within the scope of the claims may be prepared by the following exemplary reaction.
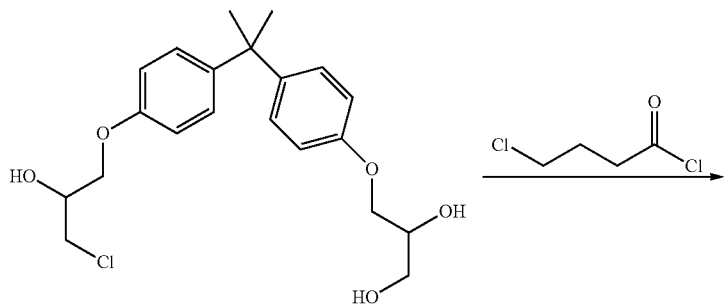
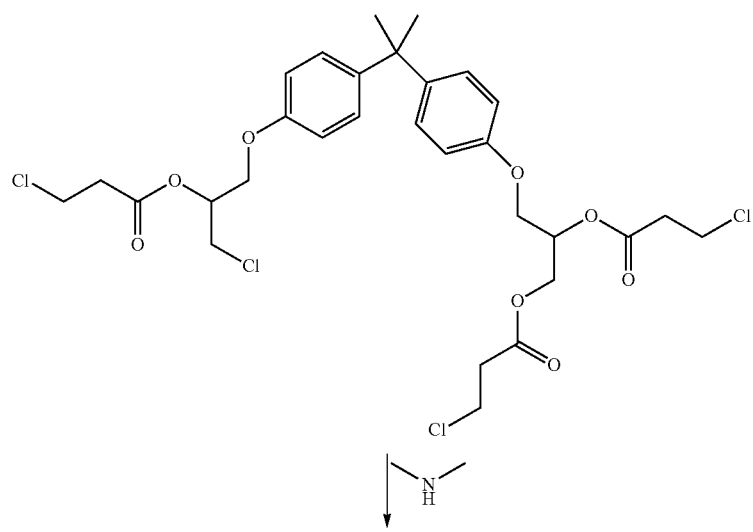

-continued

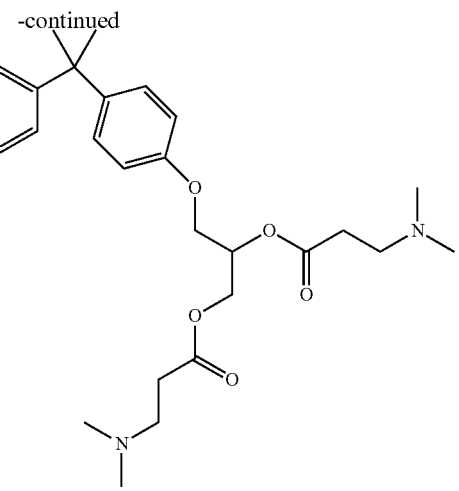

A person of skill in the art will be able to modify the synthetic approaches described herein, in combination with or not in combination with the isolation techniques described herein to prepare the Compounds of Formula I and Formula II.

In some embodiments, compounds of Formula I or Formula II above may be used for systemic treatment of at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. In some embodiments compounds of Formula I or Formula II may be used in the preparation of a medicament or a composition for systemic treatment of an indication described herein. In some embodiments, methods of systemically treating any of the indications described herein are also provided.

Compounds as described herein may be in the free form or in the form of a salt thereof. In some embodiment, compounds as described herein may be in the form of a pharmaceutically acceptable salt, which are known in the art (Berge et al., J. Pharm. Sci. 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition according to the invention includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: prostate cancer, breast cancer, ovarian cancer, endometrial cancer, hair loss, acne, hirsutism, ovarian cysts, polycystic ovary disease, precocious puberty and age-related macular degeneration. For example, compounds and all their different forms as described herein may be used as neoadjuvant (prior), adjunctive (during), and/or adjuvant (after) therapy with surgery, radiation (brachytherapy or external beam), or other therapies (eg. HIFU).

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions. Some compounds of this invention may be toxic at some concentrations. Titration studies may be used to determine toxic and non-toxic concentrations. Toxicity may be evaluated by examining a particular compound's or composition's specificity across cell lines using PC3 cells as a negative control that do not express AR Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, rat, mouse, cow, horse, pig, sheep, goat, dog, cat, etc. The subject may be suspected of having or at risk for having a cancer, such as prostate cancer, breast cancer, ovarian cancer or endometrial cancer, or suspected of having or at risk for having acne, hirsutism, alopecia, benign prostatic hyperplasia, ovarian cysts, polycystic ovary disease, precocious puberty, or age-related macular degeneration. Diagnostic methods for various cancers, such as prostate cancer, breast cancer, ovarian cancer or endometrial cancer, and diagnostic methods for acne, hirsutism, alopecia, benign prostatic hyperplasia, ovarian cysts, polycystic ovary disease, precocious puberty, or age-related macular degeneration and the clinical delineation of cancer, such as prostate cancer, breast cancer, ovarian cancer or endometrial cancer, diagnoses and the clinical delineation of acne, hirsutism, alopecia, benign prostatic hyperplasia, ovarian cysts, polycystic ovary disease, precocious puberty, or age-related macular degeneration are known to those of ordinary skill in the art Definitions used include ligand-dependent activation of the androgen receptor (AR) by androgens such as dihydrotestosterone (DHT) or the synthetic androgen (R1881) used for research purposes. Ligand-independent activation of the AR refers to transactivation of the AR in the absence of androgen (ligand) by, for example, stimulation of the cAMP-dependent protein kinase (PKA) pathway with forskolin (FSK). Some compounds and compositions of this invention may inhibit both FSK and R1881 induction of ARE-luciferase (ARE-luc) (See Example 1). Such compounds may block a mechanism that is common to both ligand-dependent and ligand-independent activation of the AR. This could involve any step in activation of the AR including dissociation of heatshock proteins, essential post-translational modifications (e.g., acetylation, phosphorylation), nuclear translocation, protein-protein interactions, formation of the transcriptional complex, release of co-repressors, and/or increased degradation.

Some compounds and compositions of this invention may inhibit R1881 only and may interfere with a mechanism specific to ligand-dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism may be used to treat such conditions.

Some compounds and compositions of this invention may only inhibit FSK induction and may be specific inhibitors to ligand-independent activation of the AR. These compounds and compositions may interfere with the cascade of events that normally occur with FSK and/or PKA activity or any downstream effects that may play a role on the AR (e.g. FSK increases MAPK activity which has a potent effect on AR activity). Examples may include an inhibitor of cAMP and or PKA or other kinases.

Some compounds and compositions of this invention may induce basal levels of activity of the AR (no androgen or stimulation of the PKA pathway).

Some compounds and compositions of this invention may increase induction by R1881 or FSK. Such compounds and compositions may stimulate transcription or transactivation of the AR.

Some compounds and compositions of this invention may inhibit activity of the androgen receptor N-terminal domain (AR-NTD). Interleukin-6 (IL-6) also causes ligand-independent activation of the AR in LNCaP cells and can be used in addition to FSK.

Compounds and compositions of this invention may interact with the AR-NTD or with another protein required for transactivation of the AR-NTD.

Various alternative embodiments and examples of the invention are described herein. These embodiments and examples are illustrative and should not be construed as limiting the scope of the invention.

EXAMPLES

General Methodologies
Cell Lines, Androgen and Reporters

LNCaP cells were employed initially for all experiments because they are well-differentiated human prostate cancer cells in which ligand-independent activation of the AR by FSK has been characterized (Nazareth et al 1996 *J. Biol. Chem.* 271, 19900-19907; and Sadar 1999 *J. Biol. Chem.* 274, 7777-7783). LNCaP cells express endogenous AR and secrete prostate-specific antigen (PSA) (Horoszewicz et al 1983 *Cancer Res.* 43, 1809-1818). LNCaP cells can be grown either as monolayers in cell culture or as tumors in the well-characterized xenograft model that progresses to androgen independence in castrated hosts (Sato et al 1996 *J. Steroid Biochem. Mol. Biol.* 58, 139-146; Gleave et al 1991 *Cancer Res.* 51, 3753-3761; Sato et al 1997 *Cancer Res.* 57, 1584-1589; and Sadar et al 2002 *Mol. Cancer Ther.* 1(8), 629-637). PC3 human prostate cancer cells do not express functional AR (Kaighn et al 1978 Natl. *Cancer Inst. Monogr.* 49, 17-21) and were used to test specificity of compound for the AR. Small molecules that specifically target the AR-NTD should have no effect on PC3 cells. This means that they should not alter the proliferation of PC3 cells if they specifically block the AR to mediate their inhibitory effects. R1881 was employed since it is stable and avoids problems associated with the labile physiological ligand dihydrotestosterone (DHT). Reporter specificity may be determined using several alternative reporter gene constructs. Some well characterized ARE-driven reporter gene constructs that have been used extensively are the PSA (6.1 kb) enhance/promoter which contains several AREs and is highly inducible by androgens as well as by FSK (Ueda et al 2002 A *J. Biol. Chem.* 277, 7076-7085) and the ARR3-thymidine kinase (tk)-luciferase, which is an artificial reporter construct that contains three tandem repeats of the rat probasin ARE1 and ARE2 regions upstream of a luciferase reporter (Snoek et al 1996 *J. Steroid Biochem. Mol. Biol.* 59, 243-250). CMV-luc (no AREs and is constitutively active) was employed to determine that a compound does not have a general inhibitory effect on transcription.

Animal Models

Some experiments involved the use of SCID mice. SCID mice were chosen because the human cell lines and transplantable tumors survive in immunocompromised animals and SCID mice show the best take rates. All procedures have been approved by the University of British Columbia Committee for Animal Ethics and are annually reviewed. In the event of an emergency where proper animal care can not be provided, animals are euthanized at the discretion of the veterinarians or Animal Care Team. Veterinarians are responsible for inspections and consultation. The signed Animal Care Certificate specifically states, "The Animal Care Committee has examined and approved the use of animals for the above experimental project or teaching course, and have been given an assurance that the animals involved will be cared for in accordance with the principles contained in Care of Experimental Animals—A Guide for Canada, published by the Canadian Council on Animal Care."

Subcutaneous Xenografts

Six to eight-week old male athymic SCID mice were inoculated subcutaneously in the flank region via a 27-gauge needle with a 150 µl suspension of LNCaP or PC3 human prostate cancer cells ($1 \times 10^6$ cells). The inoculations took place while the animal was under isofluorane anaesthesia. The tumor take rate is approximately 75%. Mice bearing tumors of 100 mm$^3$ were randomly assigned to treatment groups. Castration was performed as described below. Tumor volume (formula: L×W×H×0.5236) was measured in mice bearing LNCaP subcutaneous tumors that became palpable or visible and at least 40 mm$^3$. The animals were monitored daily and tumors were measured every 5 days.

Duration of Experiments

Assessment of tumor volume (not to exceed 1000 mm$^3$) was the criteria to determine termination of subcutaneous xenograft experiments.

Histology and Immunohistochemistry

For routine histology, major organs and xenografts were harvested upon completion of the experiment and were fixed in 10% neutral buffered formalin and then embedded in paraffin. Fixed sections were cut and stained with H&E. To determine possible effects of compounds on the proliferation rates and apoptosis in xenografts, Ki-67 immunostaining and the TUNEL assay was performed. Ki-67 immunostaining used the MIB-1 monoclonal antibody at an IgG concentration of 0.5 µg/ml (1:50) on processed tissue sections. Levels of AR were determined by immunohistochemistry or Western blot analysis.

Androgen Withdrawal to Induce Progression

Androgen withdrawal was completed by castration. Under isoflurane anaesthesia, a 5 mm vertical incision was used to gently withdraw the epididymal fat pad, to which the testis were attached, and to remove the testis from body. The cord connecting the testis to the blood supply was ligated with a suture, then cut. The cord was then returned to the abdominal cavity. Surgical suture was used to close the incision. To relieve pain, buprenorphine (0.05 mg/kg) was injected prior to surgery.

Xenograft and Organ Retrieval

All xenografts and major organs were retrieved for analyses. Retrieval was performed after sacrifice by cardiac arrest by $CO_2$ gas and the xenografts or organs were removed for immunohistochemistry analysis.

Euthanasia

Animals were sacrificed by cardiac arrest by $CO_2$ gas. This method is the policy set by the Animal Care Committee and is environmentally sensitive, effective, economic, and ethically approved.

Chemical Synthesis

All reactions were performed in flame-dried round bottomed flasks. The flasks were fitted with rubber septa and reactions were conducted under a positive pressure of argon unless otherwise specified. Stainless steel syringes were used to transfer air—and moisture-sensitive liquids. Flash column chromatography was performed as described by Still et al. (Still, W. C., Kahn, M., Mitra, A., *J. Org. Chem.* 1978, 43, 2923) using 230-400 mesh silica gel. Thin-layer chromatography was performed using aluminium plates pre-coated with 0.25 mm 230-400 mesh silica gel impregnated with a fluorescent indicator (254 nm). Thin-layer chromatography plates were visualized by exposure to ultraviolet light and a solution of p-anisaldehyde (1% p-anisaldehyde, 2% $H_2SO_4$, 20% acetic acid and 77% ethanol) followed by heating (~1 min) with a heating gun (~250° C.). Organic solutions were concentrated on Büchi B-114 rotatory evaporators at ~25 torr at 25-30° C.

Commercial reagents and solvents were used as received. All solvents used for extraction and chromatography were HPLC grade. Normal-phase Si gel Sep paks™ were purchased from Waters, Inc. Thin-layer chromatography plates were Kieselgel 60F$_{254}$. All synthetic reagents were purchased from Sigma Aldrich Canada.

Proton nuclear magnetic resonance ($^1$H NMR) spectra were recorded at 25° C. using a Bruker 400 with inverse probe and Bruker 400 spectrometers, are reported in parts per million on the δ scale, and are referenced from the residual protium in the NMR solvent (CDCl$_3$: δ 7.24 (CHCl$_3$), DMSO-d$_6$: δ 2.50 (DMSO-d$_5$)). Data is reported as follows: chemical shift [multiplicity (s=singlet, d=doublet, dd=doublet of doublets, ddd=double doublet of doublets, dm=double multiplet, t=triplet, m=multiplet), coupling constant(s) in Hertz, integration]. Carbon-13 nuclear magnetic resonance ($^{13}$C NMR) spectra were recorded with a Bruker 400 spectrometer, are reported in parts per million on the δ scale, and are referenced from the carbon resonances of the solvent (CDCl$_3$: δ 77.23, DMSO-d$_6$: δ 39.51). Data is reported as follows: chemical shift. Fluorine nuclear magnetic resonance ($^{19}$F NMR) spectra were recorded at 25° C. using a Bruker 300 spectrometer, are reported in parts per million on the δ scale. Data is reported as follows: chemical shift [multiplicity (td=triplet of doublets), coupling constant (s) in Hertz].

Example 1

Application of a number of screens was used to identify active compounds that inhibited the activity of the AR NTD. The initial screen was a cell-based assay comprising of LNCaP cells maintained in culture. The assay consists of activating the AR using both androgen (ligand-dependent) and forskolin (ligand-independent) and measuring the levels of secreted PSA by LNCaP cells in the presence and absence of crude extracts. PSA is an androgen-regulated gene that contains several well-characterized AREs.

Androgen-independent increases in PSA gene expression occur in prostate cancer cells by a mechanism dependent upon the AR. PNG 01-185 extract was observed to block PSA secretion induced by both androgen and forskolin.

To ensure that the inhibitory effects of PNG 01-185 extract on endogenous PSA protein was at the transcriptional level, reporter gene constructs were also examined Activation of the endogenous AR was measured in LNCaP human prostate cancer cells by measuring androgen-responsive reporters that contain androgen response elements (AREs) such as the PSA-luciferase reporter gene construct or the ARR3-luciferase reporter. LNCaP cells maintained as monolayers were transfected with PSA-luciferase and were used to screen the crude extracts prepared from marine sponges as well as some selected commercial compounds. Measurement of both PSA-luc and ARR3-luc was carried out because PSA-luc is highly induced by androgen and in the absence of androgens induced by FSK. R1881 (1 nM) was used to mediate ligand-dependent activation of the AR and concentrations of FSK (50 µM) were used to mediate ligand-independent activation of the AR. PNG 01-185 was observed to block PSA-luciferase activity induced by both R1881 and FSK (FIG. 1). Controls included parallel experiments with cell lines that do not express AR and other reporters that do not contain AREs.

Figure 2:
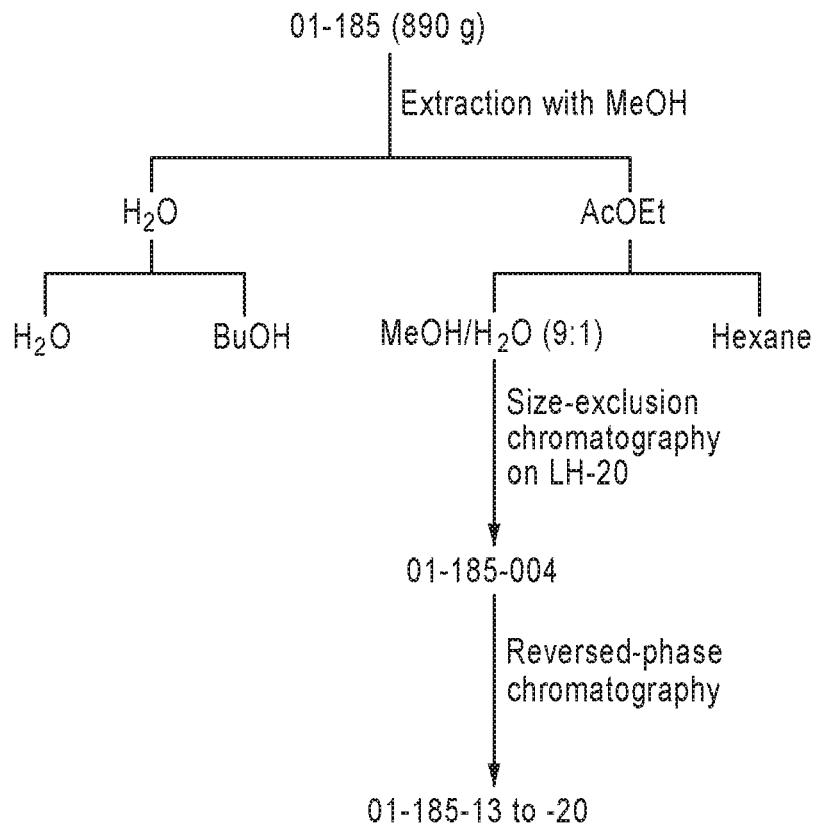
FIG. 2 is a flowchart showing the fractionation of PNG 01-185 compounds to identify PNG 01-185-17-9.
Figure 3:
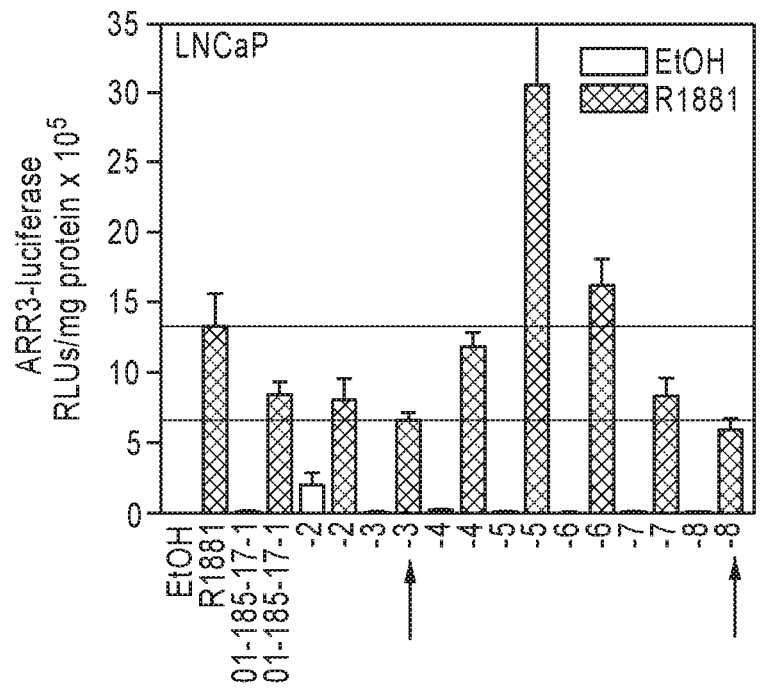
FIG. 3 shows the effects of fractions of PNG 01-185-17 on ARR3-luciferase (ARR3-luc) activity. Fractions 17-3 and 17-8 caused a 50% inhibition of ARR3-luc activity.
Figure 4:
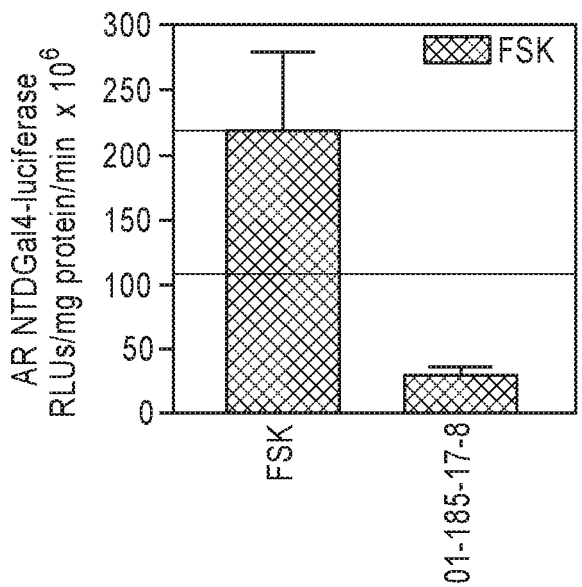
FIG. 4 shows that the PNG01-185-17-8 fraction inhibited AR-NTDGal4-luc activity.

PNG 01-185 extract was fractionated according to the scheme shown in FIG. 2 to produce PNG 01-185-17. Each fraction of PNG 01-185-17 was re-tested on ARR3-luc activity and fractions 3 and 8 showed at least 50% inhibition (FIG. 3). These fractions were next tested for their ability to inhibit the AR NTD. LNCaP cells were co-transfected with the expression vector for Gal4DBD-AR$_{1-558}$ and the complimentary 5XGal4UAS-luciferase reporter as shown in FIG. 4. Induction of this reporter by FSK is a measure of transactivation of the Gal4DBD-AR$_{1-558}$ fusion protein (Sadar 1999 *J. Biol. Chem.* 274, 7777-7783). Extracts identified above were screened by such assays as well as some compounds purchased from commercial suppliers. R1881 does not induce such assays (binds to the ligand-binding domain (LBD) of the AR which is not present in the Gal4DBD-AR$_{1-558}$ chimera) and therefore was not used except as a negative control. These studies showed that PNG 01-185-17-8 inhibited activation of the AR NTD.

The following in Table 3 are chemical structures for compounds from sponge extracts or commercially available compounds that showed activity using the above-described assays:

TABLE 3

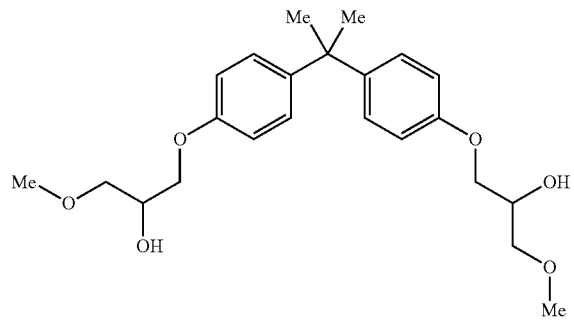

Sponge Extract:
PNG01-185-017-2

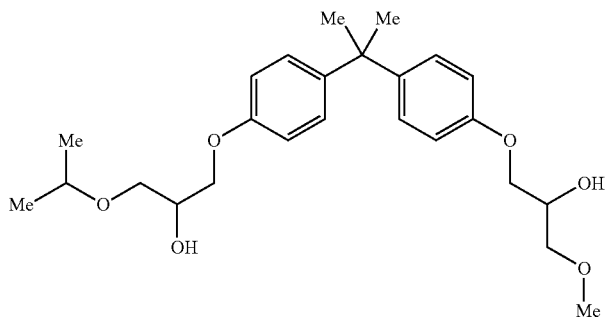

Sponge Extract:
PNG01-185-017-5

TABLE 3-continued
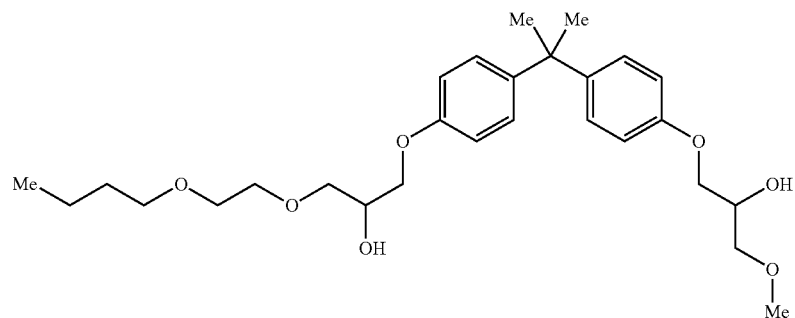
Sponge Extract:
PNG01-185-017-6
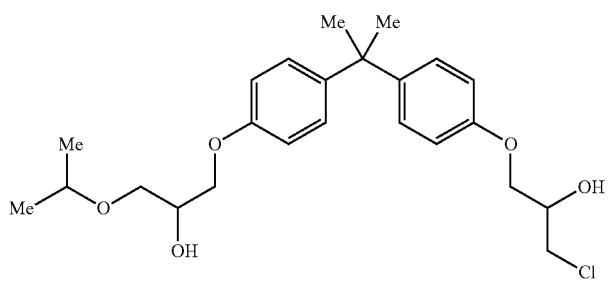
Sponge Extract:
PNG01-185-017-7
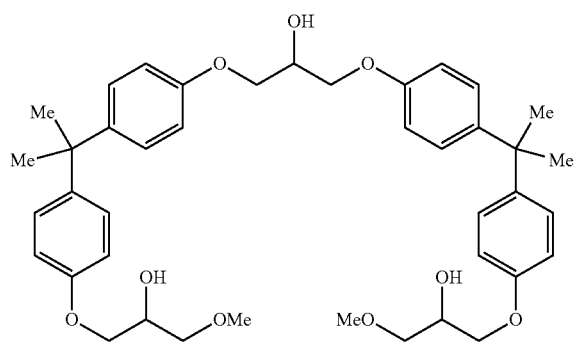
Sponge Extract:
PNG01-185-017-8
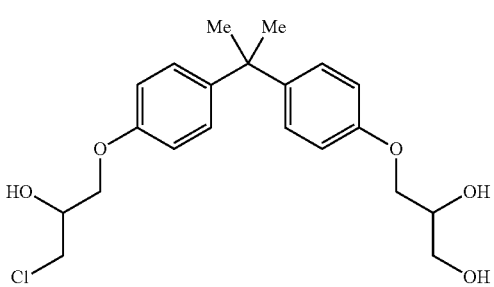
Sponge Extract:
PNG01-185-017-9-2
PNG01-185-17-9-2
185-9-2
B2

TABLE 3-continued

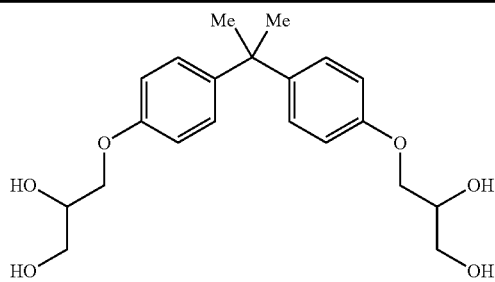

Commercially Purchased Compound
(Aldrich)
PNG01-185-017-9-1
PNG01-185-17-9-1
185-9-1

IC50s were determined for each hit that showed a dose response. Identified extracts were used to isolate a purified form of the compound from natural compounds library that mediated the inhibitory effect on transactivation of the AR as described in Example 2, followed by secondary screens described in Example 3.

The following compounds in Table 4 showed no activity in the above-described assays.

TABLE 4

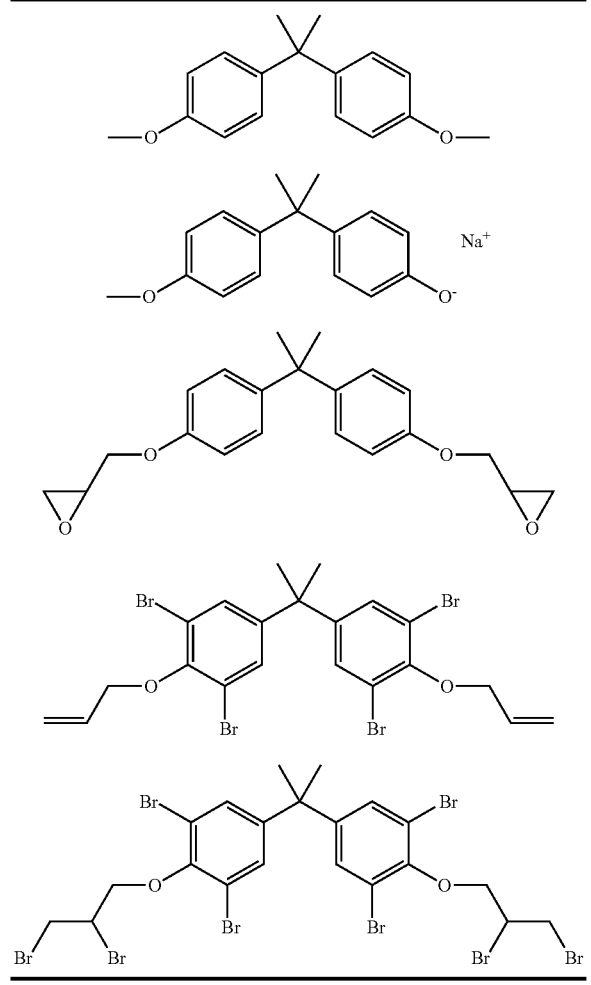

The structural resemblance of some of the active compounds to BADGE (Bisphenol A Diglycidic Ether) indicates that they are most likely of industrial origin. The collected sponge presumably bioaccumulated the compounds from the contaminated seawater. This was a fortuitous event because it is unlikely that these compounds would have been screened in the bioassays under any other circumstances.

Example 2

Purified active compound from the extracts described in Example 1 were isolated. Specimens of *Geodia lindgreni* (Lendenfeld, 1903) were collected by hand using SCUBA at a depth of 5 M from under rocks on a protected reef near Loloata Island, Papua New Guinea. The frozen sponge (890 g) was subsequently extracted exhaustively with MeOH and the crude extracts were observed to be active in the assays described above in Example 1. Bioassay guided fractionation of the extract by sequential application of Sephadex LH20, reversed-phase flash column chromatography and reversed-phase gradient HPLC gave purified samples of PNG01-185-017-2, -5, -6, -7 and -8 (FIG. 2). The structures have been elucidated by analysis of NMR and MS data and they are shown above in Example 1.

Bioassay guided fractionation of active extracts followed a standard protocol. Initially, the crude extract was suspended in water and sequentially extracted with hexanes, $CH_2Cl_2$, and EtOAc to generate four sub-fractions of differing polarity. The first chromatography carried out on the active fraction from this initial partition was a Sephadex LH20 chromatography using either pure methanol or a mixed solvent system as the eluent. Subsequent fractionations were carried out by open column flash silica-gel or flash reversed-phase chromatography, HPLC (normal-phase and/or reversed-phase), or centrifugal counter current chromatography (on an Ito Coil apparatus), etc. as the situation warranted. Structure elucidation of novel metabolites was achieved by spectroscopic analysis, using 1D and 2D NMR techniques and mass spectrometry, including a Bruker AV600 NMR spectrometer equipped with a cryoprobe and the NANUC Varian 800 MHz NMR spectrometer in Edmonton, Alberta, Canada. Purified compounds were tested for activity using the screens described above in Example 1 (ARE-luciferase activities and NTD transactivation) and then used for secondary screens described in Example 3.

Example 3

The compounds were validated by application of secondary screens. Purified compounds were tested for their ability to inhibit: transactivation of the androgen receptor N-terminal domain (AR NTD); other steroid receptors (specificity); endogenous expression of PSA mRNA; AR interaction on AREs; N/C interaction; and proliferation of prostate cancer cells in response to androgen.

Transactivation of the AR NTD

Figure 5:
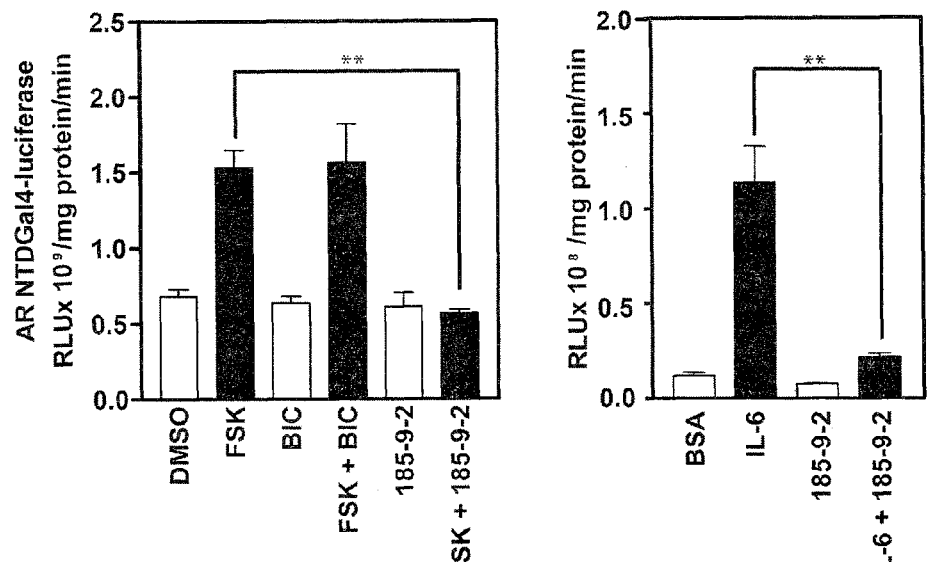
FIG. 5 Structural derivative, PNG01-185-17-9-2 (185-9-2) of PNG01-185-17-8 blocked FSK (50 μM) (left) and interleukin-6 (IL-6, 50 ng/ml) (right) induced transactivation of the AR NTD while the antiandrogen bicalutamide (BIC 10 μM) had no effect.

In the absence of serum and androgen, both forskolin (FSK), which stimulates PKA activity, and IL-6 increase PSA gene expression in prostate cancer cells by a mechanism involving transactivation of the AR NTD (Sadar, M. D., *J. Biol. Chem.* 274, 7777-7783 (1999); Ueda, T., Bruchovsky, N., Sadar, M. D., *J. Biol. Chem.* 277, 7076-7085 (2002); Ueda, T., Mawji, N. R., Bruchovsky, N., Sadar, M. D., *J. Biol. Chem.* 277, 38087-38094 (2002 B); Quayle S N, Mawji N R, Wang J, Sadar M. D., Proc Natl Acad Sci USA. 2007 January 23; 104(4):1331-6.) The ability of 185-9-2 to inhibit transactivation of the AR NTD was tested by cloning amino acids 1-558 of the human AR NTD into the C-terminus of Gal4DBD. Expression vectors for these chimeric proteins were cotransfected into LNCaP cells with a reporter gene containing the Gal4-binding site as cis-acting elements (p5xGal4UAS-TATA-luciferase). Cells were pretreated with bicalutamide (BIC, 10 µM) or 185-9-2 (5 ug/ml=12 µM)) before the addition of FSK or IL-6. Controls included bicalutamide which does not affect such assays because it binds to the LBD of the AR which is not present in the Gal4DBD-AR$_{1-558}$ chimera. 185-9-2 was observed to reduce both FSK-induced and IL-6-induced transactivation of the AR NTD to baseline levels (FIG. 5). 185-9-2 was observed to have an IC$_{50}$ of ~6.6 µM for inhibition of transactivation of the AR NTD.

Steroid Receptor Specificity

Figure 6:
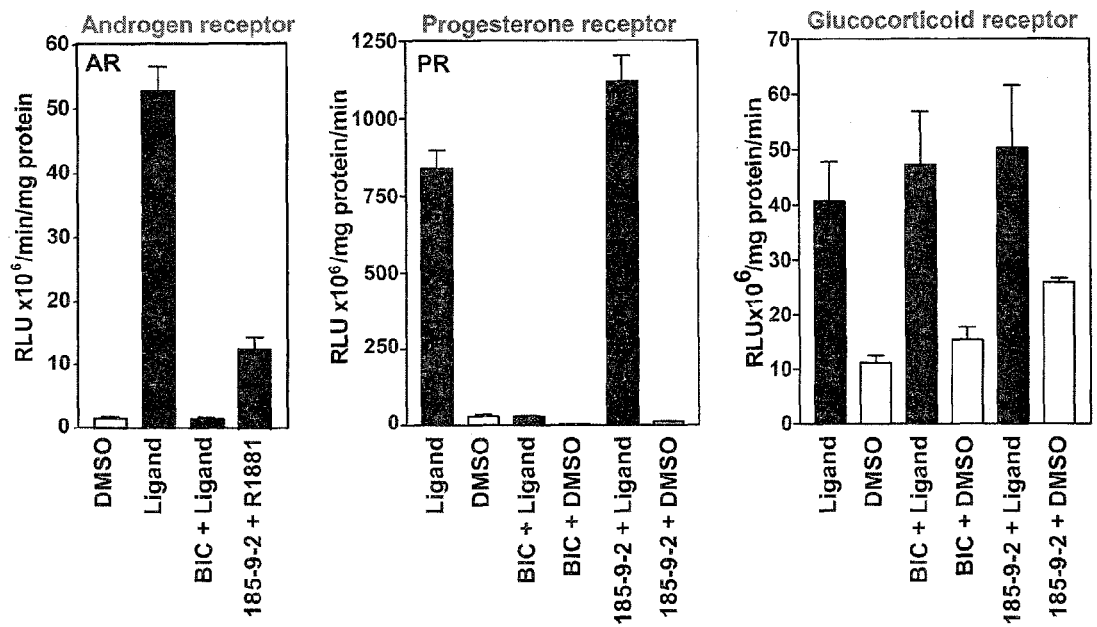

Sequence similarities of amino acids in the AR with related human steroid receptors PR and glucocorticoid receptor (GR) are significant in some domains such as the DBD. The AR NTD shares less than 15% homology with the PR and GR, but these receptors interact with some of the same proteins (eg., SRC-1 and CBP). Therefore, reporter gene assays were used to determine if candidate compounds that block AR activity have any effect on GR and PR transcriptional activity. Cells were co-transfected with expression plasmids for full-length hGR, PRβ and the relative reporter (i.e., pGR-Luc or PRE-E1b-Luc reporters). Cells were then treated with ethanol vehicle, dexamethasone (GR), 4-pregnene-3,20 dione (progesterone) (PR) followed by measurement of luciferase activity. 185-9-2 inhibited AR transcriptional activity, but did NOT inhibit PRE-luciferase or GRE-luciferase activities in response to ligand (FIG. 6). In contrast, bicalutamide (10 µM) inhibited the transcriptional activity of PR. Some antiandrogens currently used in the clinic have progestational and glucocorticoidal activities. In adult males, the role of the PR activity is unclear. 185-9-2 does not inhibit the transactivation of other steroid receptors. These studies also provide evidence that 185-9-2 does not have non-specific and general effects on transcription or translation since it did not inhibit induction of these luciferase reporters in response to their cognant ligands. Since 185-9-2 blocks PSA-luciferase reporter gene activity that contains several AREs and is inducible by androgens and FSK supports that its inhibitory effects are at the level of transcription. These studies suggest that 185-9-2 is specific to the AR implying there should be fewer side effects from systemic delivery as opposed to if other steroid receptors are affected.

Endogenous Gene Expression

Figure 7:
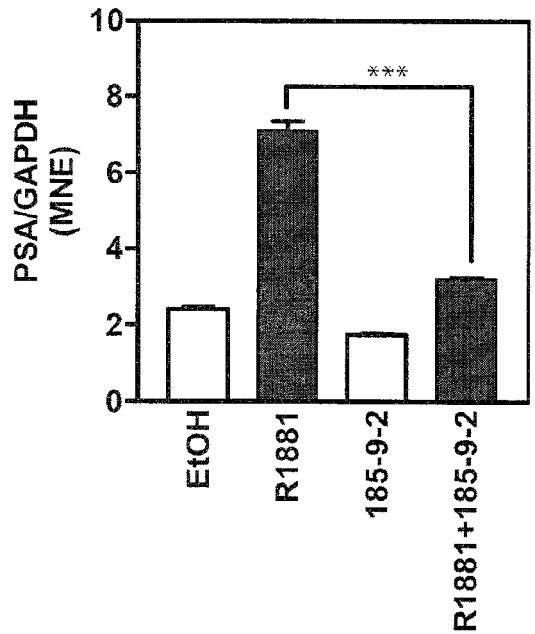
FIG. 7 PNG01-185-17-9-2 (185-9-2, 5 μg/ml) inhibited endogenous PSA gene expression (PSA mRNA) induced by R1881 (1 nM) as measured by QRT-PCR. Levels of PSA mRNA were normalized to levels of GADPH mRNA. MNE is the mean normalized expression.

Induction of PSA mRNA by both R1881 (ligand-dependent) and FSK (ligand-independent) in LNCaP cells is dependent upon AR (Sadar, M. D., *J. Biol. Chem.* 274, 7777-7783 (1999); Wang G, Jones S J, Marra M A, Sadar M D, *Oncogene* 2006; 25:7311-23.). To test whether the compounds have an effect on endogenous gene expression, the levels of PSA mRNA in LNCaP cells exposed to R1881 were measured. LNCaP cells (in serum-free and phenol-red free media) were incubated with compounds for 1 hour before the addition of R1881 (1 nM) for an additional 16 hours before harvesting and isolating total RNA. Levels of mRNA were measured using QPCR. Levels of PSA mRNA were normalized to levels of GAPDH mRNA. 185-9-2 was observed to block endogenous PSA mRNA induction by R1881 to almost baseline levels (FIG. 7).

AR Interaction with AREs on the DNA

Figure 8:
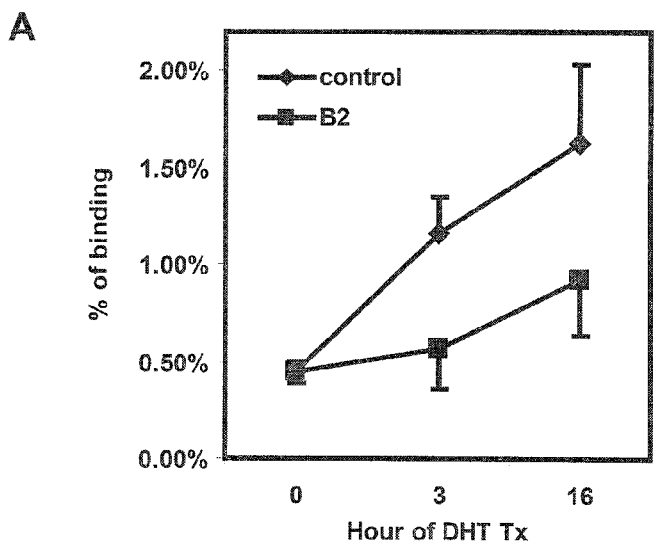
FIG. 8 A. ChIP analysis measuring recruitment of AR to the PSA-ARE in the enhancer region in LNCaP cells treated for 0, 3 hr, 16 hr with DHT with or without 185-9-2 (B2, 10 μg/ml). B. Levels of AR protein were not decreased in whole cell extracts from cells treated for 3 or 16 hours with 185-9-2 (B2). Western blot analysis of levels of AR using an antibody to the androgen receptor. Levels of b-actin protein are included as a loading control.
Figure 8:
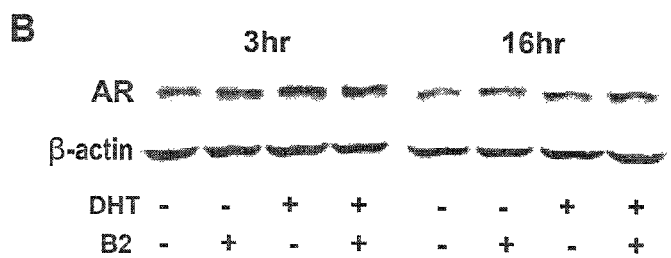
Figure 9:
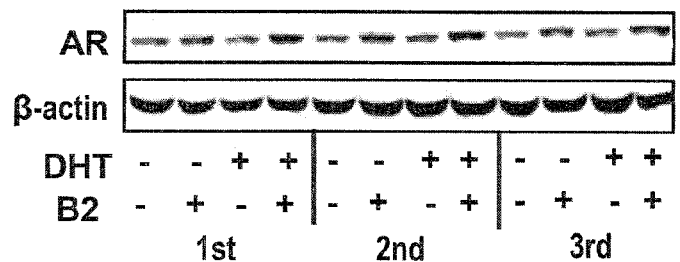

Chromatin immunoprecipitation (ChIP) was used to assess if 185-9-2 prevented AR binding to the endogenous AREs in the enhancer region of the PSA gene in the physiological context of chromatin structure. The AR shows constitutive occupancy on the PSA promoter ARE, while the enhancer ARE has inducible occupancy in response to androgen (Jia L, Coetzee G A., Cancer Res. 2005 Sep. 1; 65(17):8003-8). The occupancy of AR on these regulatory regions peaks at 16 hr of androgen treatment (Jia L, Choong C S, Ricciardelli C, Kim J, Tilley W D, Coetzee G A., *Cancer Res.* 2004 Apr. 1; 64(7):2619-26; Louie M C, Yang H Q, Ma A H, Xu W, Zou J X, Kung H J, Chen H W., Proc Natl Acad Sci USA. 2003 Mar. 4; 100(5):2226-30; Wang Q, Carroll J S, Brown M., *Mol Cell.* 2005 Sep. 2; 19(5):631-42.). LNCaP cells were treated for a short (3 h) or optimal (16 h) period of time with DHT plus or minus 185-9-2, prior to cross-linking with 1% formaldehyde and harvesting cells. The cells were lysed, sonicated, and the extracts used for immunoprecipitation with anti-AR antibody. 185-9-2 inhibited AR interaction with the ARE on the PSA enhancer in LNCaP cells in response to androgen (FIG. 8A). The decrease in AR interaction with ARE was not due to decreased levels of AR protein. Western blot analysis of AR protein from whole lysates prepared from LNCaP cells harvested at these same time points, revealed that 185-9-2 does NOT decrease levels of AR protein (FIG. 8B). Long term incubation of LNCaP cells with 185-9-2 also did not reduce levels of AR protein (FIG. 9). Thus, it is believed that 185-9-2 does not inhibit AR transcriptional activity by reducing levels of AR protein. This suggests that the mechanism of action of 185-9-2 is unique from other compounds such as AR mRNA hammerhead ribozyme, AR siRNA, pyranocoumarin, calpain, phenethyl isothiocyanate, fulvestrant, decursin, LAQ824, and baicalein that decrease levels of AR protein and are being explored in other laboratories.

185-9-2 does not Prevent Nuclear Translocation of the AR

Figure 10:
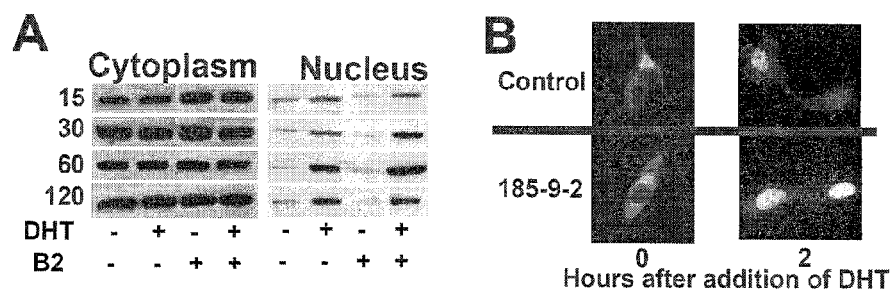
FIG. 10 A. Western blot analyses of levels of AR protein in cytosol or nucleus in LNCaP cells pretreated for 1 hr with 185-9-2 (B2) or DMSO (control) prior to 15, 30, 60, or 120 minutes of treatment with 10 nM DHT. B. Fluorescence microscopy of LNCaP cells transfected with AR-GFP pretreated for 1 hr with 185-9-2 (B2) or DMSO (control) prior to addition of 10 nM DHT and incubated an additional 2 hrs.

Another possible mechanism by which any of these inhibitors may decrease transactivation of the AR could involve prevention of nuclear translocation of AR protein. In the absence of both androgen or stimulation by alternative pathways, AR is primarily cytoplasmic. Cellular fractionation and fluorescent microscopy (FIG. 10A,B) revealed that 185-9-2 did not cause nuclear translocation of the AR on its own in the absence of androgen, nor did it prevent nuclear translocation of AR protein in response to androgen (dihydrotestsosterone, DHT).

N/C Interaction

Figure 11:
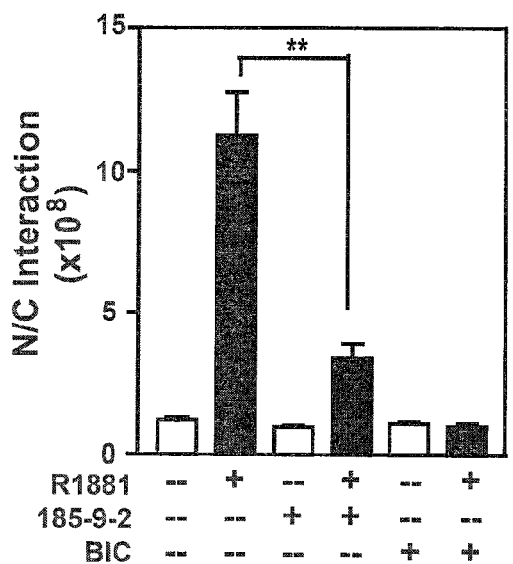
FIG. 11 N/C interaction. CV1 cells were transfected with VP16-ARTAD, Gal4-ARLBD, and the Gal4-luciferase reporter and treated with R1881 plus or minus 185-9-2 (10 μg/ml) or bicalutamide (BIC, 10 μM) for 24 hr.

Ligand-dependent activity of the AR requires interaction between the amino (N) and carboxy (C) termini for antiparallel dimer formation (He B, Kemppainen J A, Voegel J J, Gronemeyer H, Wilson E M., *J Biol Chem.* 1999, 274(52): 37219-25.). Antiandrogens such as bicalutamide, flutamide and cyproterone acetate do not stimulate this interaction on their own, and each inhibits N/C interaction induced by androgen (Wong, C. I., Zhou, Z. X., Sar, M., and Wilson, E. M. (1993) *J. Biol. Chem.* 268, 19004-19012; Langley, E., Zhou, Z. X., and Wilson, E. M. (1995) *J. Biol. Chem.* 270, 29983-29990; Kemppainen, J. A., Langley, E., Wong, C. I., Bobseine, K., Kelce, W. R., and Wilson, E. M. (1999) *Mol. Endocrinol.* 13, 440-454; Masiello D, Cheng S, Bubley G J, Lu M L, Balk S P. (2002) *J. Biol. Chem.*, 277, 29, 26321-26326). The mammalian two-hybrid system was used to measure this interaction. CV1 cells were cotransfected with the expression vector for a fusion protein of amino acids 1-565 of the AR NTD fused to VP16 at the N-terminus (VP16-ARTAD, the N terminus), the expression vector for the DBD of Gal4 fused to the LBD of the AR (amino acids 628-919; Gal4-ARLBD; the C terminus), and the Gal4-luciferase reporter (Masiello D, Cheng S, Bubley G J, Lu M L, Balk S P. (2002) *J. Biol. Chem.*, 277, 29, 26321-26326). There was no detectable interaction between the VP16-ARTAD and Gal4-ARLBD in the absence of androgen (FIG. 11). Androgen stimulated this interaction as measured by increased luciferase activity which was blocked by bicalutamide (see also, for example, Masiello D, Cheng S, Bubley G J, Lu M L, Balk S P. (2002) *J. Biol. Chem.*, 277, 29, 26321-26326). Importantly, 185-9-2 was observed to inhibit androgen-stimulated N/C interaction (compare columns 6 and 2). Thus, it is believed that 185-9-2 inhibits the transcriptional activity of the AR by preventing N/C interaction.

Proliferation Assay

Figure 12:
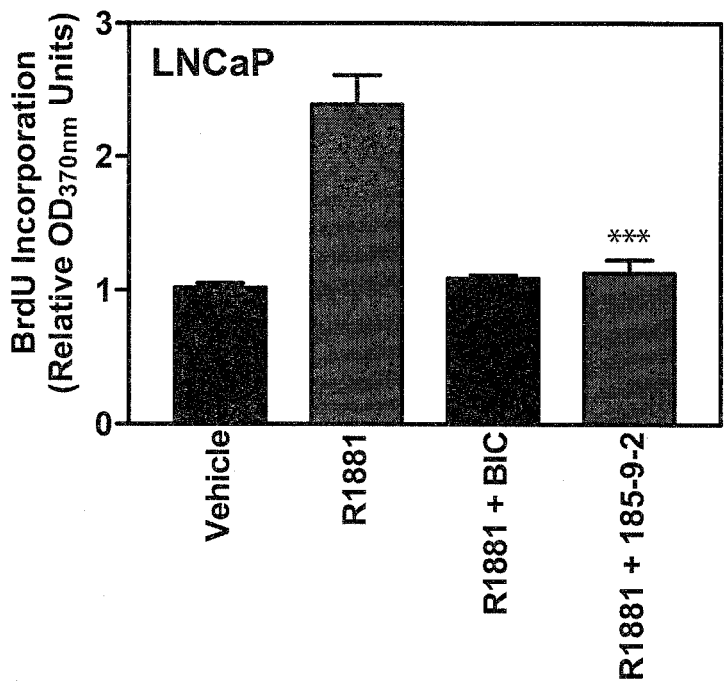
FIG. 12 PNG01-185-17-9-2 (185-9-2) blocked androgen-dependent proliferation of LNCaP cells. LNCaP cells treated with bicalutamide (BIC, 10 μM) or 185-9-2 (5 μg/ml) for 1 hr before the addition of R1881 (0.1 nM). Cells were harvested and measured for BrdU incorporation after 4 days of treatment with androgen. p=0.0001 between 185-9-2 plus R1881 and only R1881-treated.
Figure 13:
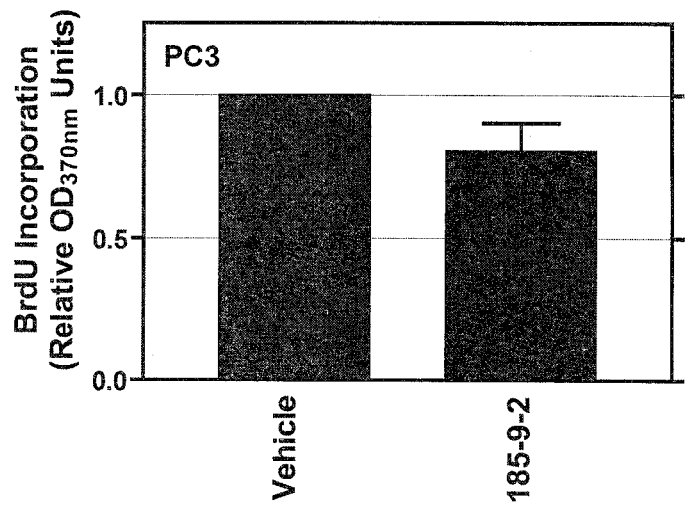
FIG. 13 PNG01-185-17-9-2 (185-9-2) does NOT block proliferation of PC3 cells (p<0.05, t-test). Cells were treated with vehicle (DMSO) or 185-9-2 (5 μg/ml) for 3 days before harvesting and measurement of BrdU incorporation. Bars represent the mean±SEM (n=3 separate experiments with 5 replicates per experiment).

The prostate gland is an androgen-dependent organ where androgens are the predominant mitogenic stimulus (Isaacs J T, Scott W W, Coffey D S., *Prog Clin Biol Res.* 1979; 33:133-44). This dependency on androgens provides the underlying rationale for treating prostate cancer with chemical or surgical castration. Androgen (0.1 nM) stimulates the proliferation of LNCaP cells. To test whether 185-9-2 interference with AR AF-1 function reduces androgen-dependent proliferation of LNCaP cells, similar to what is observed for antiandrogens used clinically, LNCaP cells were pretreated for 1 h with bicalutamide (10 μM, positive control) or 185-9-2 (5 μg/ml) prior to addition of 0.1 nM R1881. BrdU incorporation was measured 4 days later to indicate changes in proliferation in response to androgen (FIG. 12). R1881 (0.1 nM) increased proliferation over control (vehicle for R1881 and small molecules). 185-9-2 was observed to be as effective as bicalutamide in blocking androgen-induced proliferation. 185-9-2 was observed not to block proliferation of PC3 human prostate cancer cells (FIG. 13, p>0.05) that do not express functional AR and thus do not rely on the AR for growth and survival (Kaighn et al 1978 *Natl. Cancer Inst. Monogr.* 49, 17-21).

Example 4

The subcutaneous xenograft models were used to test whether the small molecules that inhibit activation of the androgen receptor in vitro have any effect on these tumors. PNG01-185-017-9-2 was tested in vivo using the LNCaP and PC3 subcutaneous xenograft models. In vivo experiments were done to provide information relevant to toxicity, the requirement for endogenous expression of AR, and whether PNG01-185-017-9-2 had an effect on tumor growth and progression to androgen independence. Tumor volume was monitored in both xenograft models.

PNG01-185-017-9-2 Reduced the Tumor Volume of LNCaP Xenografts

Figure 14:
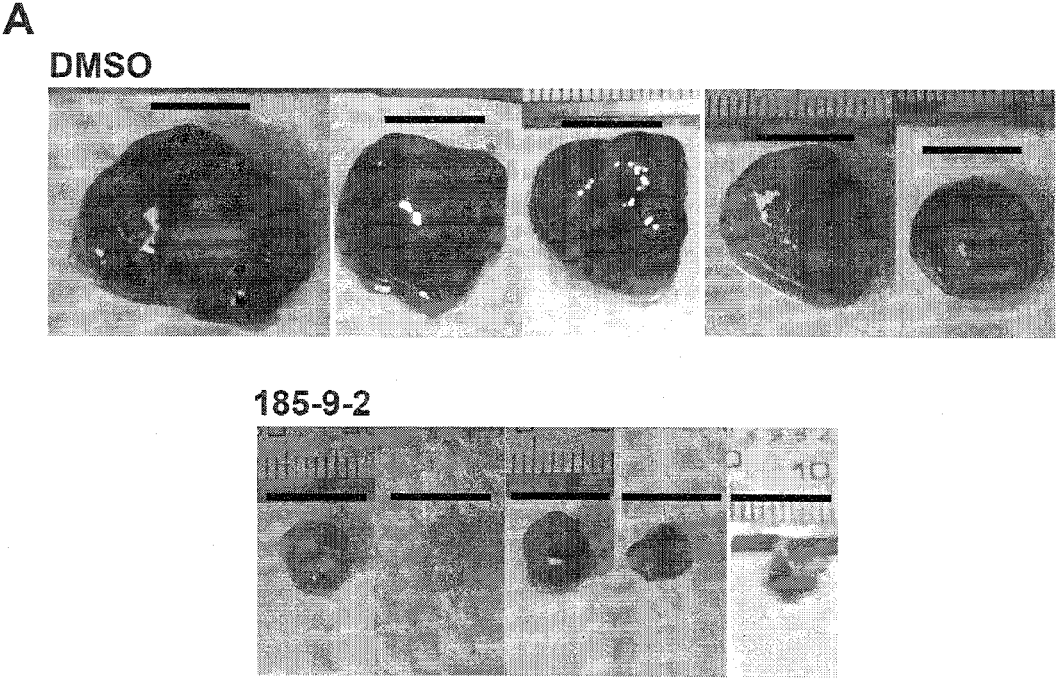
FIG. 14 A. Photographs of a representative harvested LNCaP xenografts from day 25 after the 1$^{st}$ intratumoral (I.T.) injection of either DMSO (vehicle) or 185-9-2 in castrated animals. The black bar represents 10 mm. B. Time course showing LNCaP xenograft volume over for the duration of the experiment. 185-9-2 reduced the size of the tumors (n=10) while DMSO-treated tumors continued to grow (n=9). Tumor volume at the first injection was set to 100%. Solid line represents DMSO-treated and dashed line represents 185-9-2-treated animals. C. 185-9-2 did not reduce body weight. Body weight measured at day 0 and at the end of the experiment at day 25 in mice bearing LNCaP xenografts receiving vehicle or small molecule.
Figure 14:
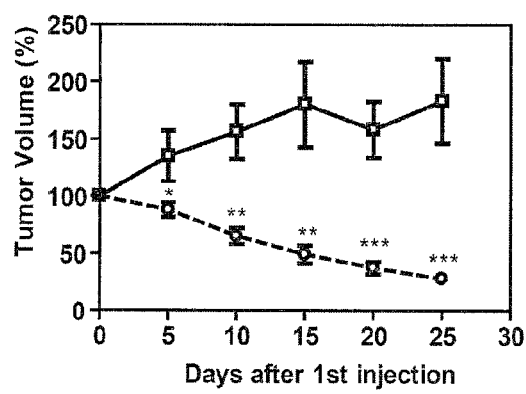
Figure 14:
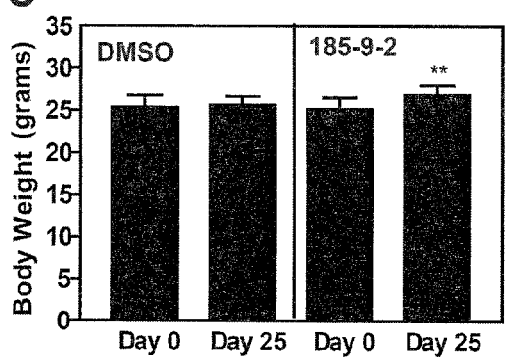
Figure 15:
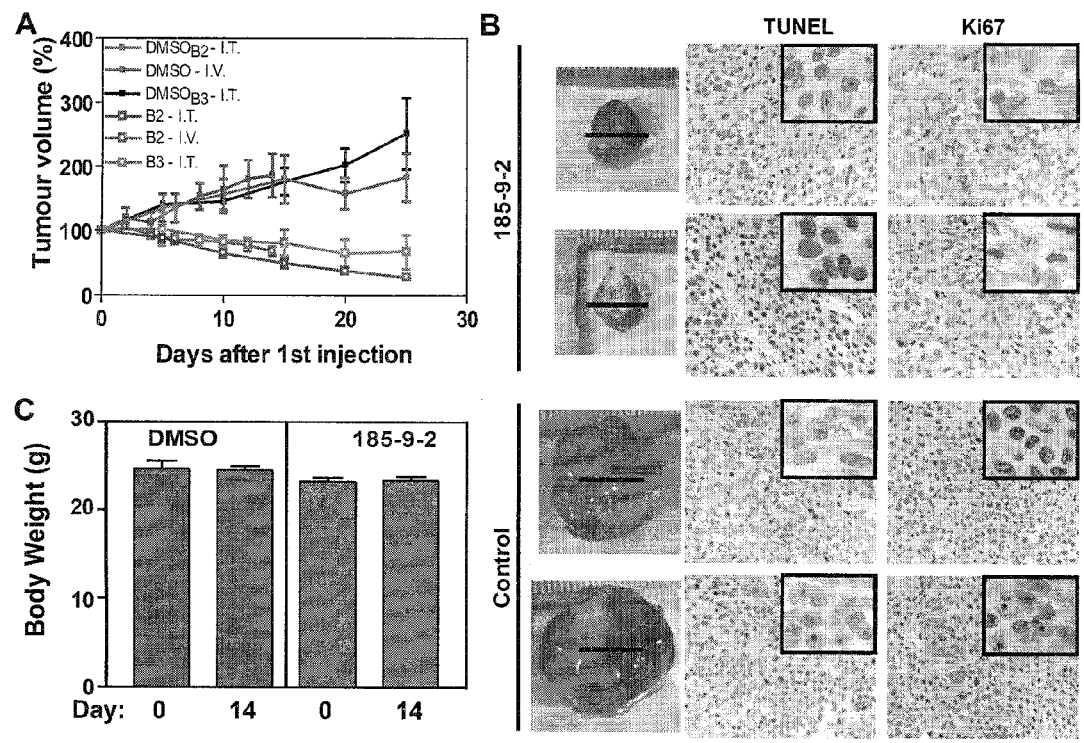
FIG. 15 A. Time course comparing intravenous (I.V.) injection of 185-9-2 (B2) versus intratumorial (I.T.) injection of 185-9-2 and BADGE.2HCl (B3, I.T. injection of 20 mg/kg body weight every 5 days, n=3 for each group) on LNCaP xenograft volume over for the duration of the experiments. 185-9-2 (B2) and BADGE.2HCl (B3) reduced the size of the tumors while DMSO-treated tumors continued to grow. Tumor volume at the first injection was set to 100%. B. Photographs of a representative harvested LNCaP xenografts from animals injected intravenously with control (DMSO vehicle) or 185-9-2 (50 mg/kg body weight every other day) in castrated animals 2 days after the last injection. The black bar represents 10 mm. Staining of sections of the shown tumor with TUNEL as an indication of apoptosis, or Ki67 as a marker of proliferation. C. Intravenous injection (I.V.) of 185-9-2 did not reduce body weight.

LNCaP human prostate cancer cells express endogenous androgen receptor (AR) and prostate-specific antigen (PSA), and progress to androgen independence in castrated hosts. LNCaP cells ($10^6$/ml) were implanted subcutaneously into NOD-SCID male mice that were at least 8 weeks in age. The cells were suspended in 75 μl of RPMI medium 1640 (5% FBS) with 75 μl of Matrigel and injected into the flank region of the host under anesthesia. The animals were castrated when the tumors were approximately 100 mm$^3$ (mean=131.1±24.9 mm$^3$; n=19) and randomized into two groups. One week after castration the animals were treated every 5 days with an intratumoral (i.t.) dose of 20 mg/kg body weight of 185-9-2 or matching volume of vehicle (control, DMSO). Animals were injected with 185-9-2 over a period of 25 days and harvested 5 days after the last injection. A total of five doses were given to the animal. Tumor volume and body weight were measured every 5 days. 185-9-2 was observed to significantly reduce the tumors, even after the first injection (FIG. 14). At the duration of the experiment the 185-9-2-treated tumors were 35.4±15.7 mm$^3$, while vehicle-treated tumors continued to grow and were 435.6±334 9 mm$^3$. Thus 185-9-2 was observed to reduce the tumor volume and did not just slow the growth. This suggests 185-9-2 may be curative for androgen-independent prostate cancer. I.T delivery of the related compound, racemic BADGE.2HCl (B3), was also observed to reduce tumor volume from 109.6±17.4 mm$^3$ to 79.0±63.6 mm$^3$ compared to I.T. delivery of DMSO which continued to grow (starting at 105.2±15.1 mm$^3$ to 256.6±73.4 mm$^3$) following the same treatment regime as for 185-9-2 (FIG. 15A). Serum PSA measurements correlated with tumor volume data (serum PSA data not shown).

Figure 16:
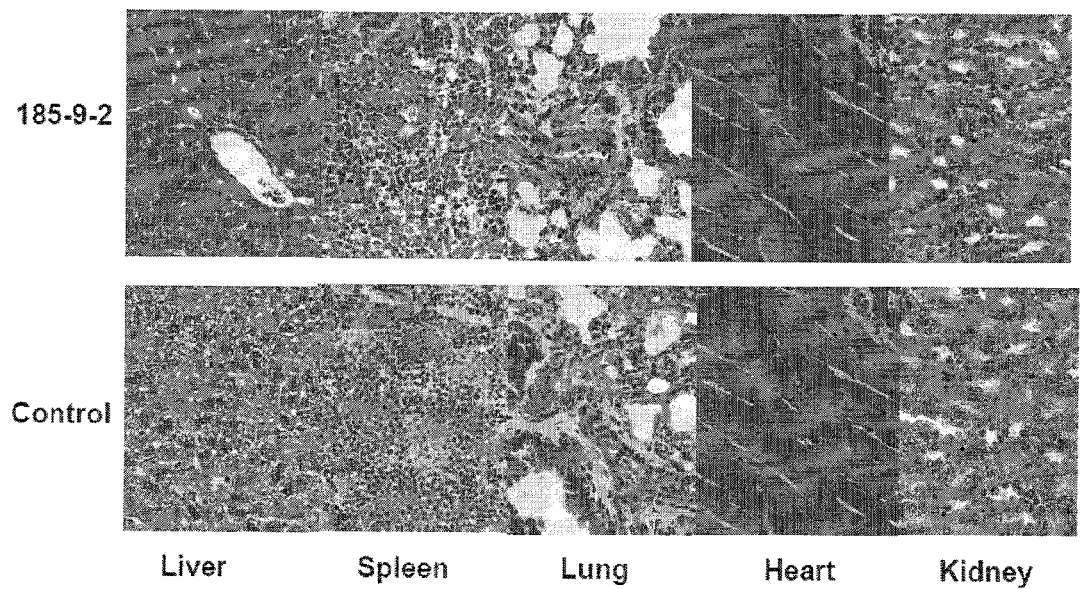
FIG. 16 Histology of major organs harvested from animals injected I.V. (see FIG. 15) with 185-9-2 (50 mg/kg body weight) every other day for a total of 5 injections. Xenografts were harvested 2 days after the last I.V. injection and stained with H&E. DMSO is the vehicle control that was also administered by I.V.

Importantly, i.v. delivery by tail vein injections every other day (50 mg/kg body weight) showed a similar rate of cytoreduction of tumors (FIG. 15A). Within just 2 weeks, i.v. injection of 185-9-2 was observed to reduce tumors from 105.6±12.0 mm$^3$ to 64.3±29.6 mm$^3$, while tumors were 187.9±42.8 mm$^3$ in animals receiving i.v. injection of DMSO. These promising data emphasize that systemic delivery is effective in reducing androgen-independent prostate cancer Immunohistochemistry (IHC) using a marker for apoptosis (TUNEL) and proliferation (Ki67) shows that intravenous delivery of 185-9-2 increased apoptosis and reduced proliferation (FIG. 15B) consistent with cytoreduction of the tumors. IHC data was prepared by a commercial lab that was blinded to treatments. 185-9-2 was observed not to cause general toxicity to animals indicated by no change in animal behavior or body weight (FIGS. 14C and 15C). Pathology review of sections of lung, heart, liver, spleen, and kidney harvested from mice receiving 185-9-2 or DMSO by i.v. delivery showed no signs of toxicity (FIG. 16).

Levels of AR Protein in Harvested Xenografts

Figure 17:
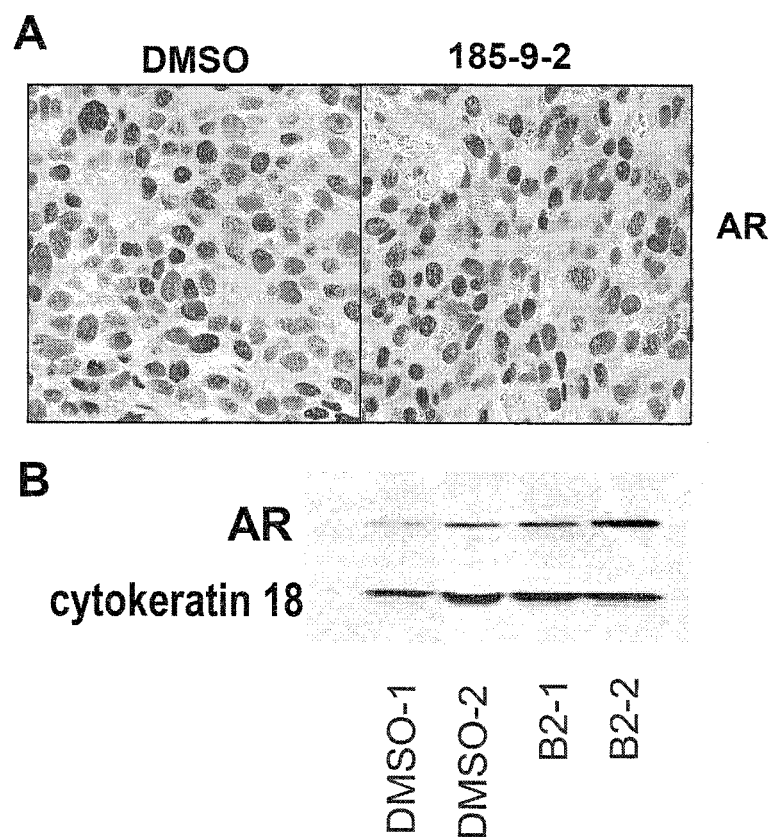
FIG. 17 In vivo, 185-9-2 does not reduce levels of AR protein. A. Xenografts were harvested from animals injected I.V. with 185-9-2 or DMSO (see FIG. 15) and sections were stained for AR using a monoclonal antibody to the NTD. B. Western blot analyses of levels of AR protein in whole cell lysates prepared from xenografts harvested at day 25 from animals injected I.T. with 185-9-2 (see FIG. 14). Lane 1 and 2 are xenografts from 2 different animals treated with DMSO (Control 1 and 2). Lane 3 and 4 are xenografts from 2 different animals treated with 185-9-2 (B2-1 and B2-2). Blots were also stained for cytokeratin 18, a marker of epithelial cells.

IHC (FIG. 17A) and western blot analysis (FIG. 17B) provide evidence that I.V. or I.T delivery of 185-9-2 did not decrease levels of AR protein in xenografts compared to levels of AR protein in vehicle-treated xenografts. Levels of cytokeratin 18 were measured as an indication of amount of epithelial cells in the xenograft samples.

Effects on Angiogenesis

Figure 18:
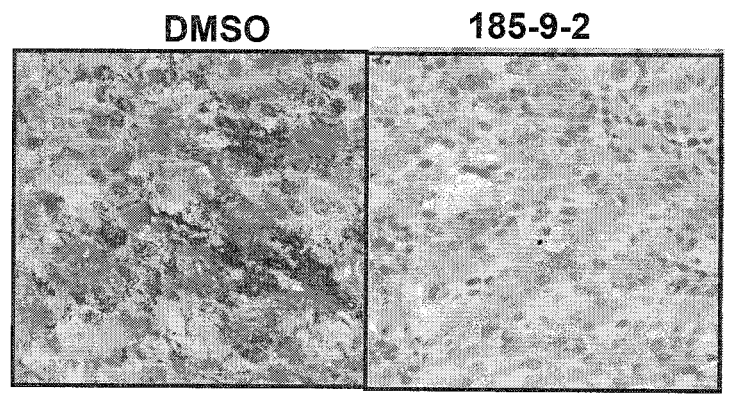
FIG. 18 illustrates that 185-9-2 decreased levels of vascular endothelial growth factor (VEGF) protein in LNCaP xenografts harvested at day 25 from castrated hosts. VEGF is an important growth factor involved in angiogenesis. The left column shows staining of a xenograft treated with vehicle control.

Angiogenesis in prostate cancer is predominantly dependent upon vascular endothelial growth factor (VEGF). Testosterone is a potent inducer of VEGF in the prostate (Häggström et al 1999 *J Urol.* 161, 1620-1625) and re-expression of VEGF in androgen independent tumours is consistent with the re-expression of androgen-regulated genes (Gregory et al 1998 *Cancer Res.* 58, 5718-5724). Expression of VEGF is associated with androgen independence (Mitsiades et al 2001 *Expert Opin Investig Drugs.* 10, 1099-1115) and aggressive metastatic disease (Harper et al 1998 *J Pathol.* 186, 169-177; Balbay et al 1999 *Clin Cancer Res.* 5, 783-789; Melnyk et al 1999 *J Urol.* 161, 960-963). Staining of the harvested tumors for VEGF reveal that PNG01-185-017-9-2 inhibited the expression of VEGF (FIG. 18).

Subcutaneous PC3 Xenograft Models in Non-Castrated Hosts

Figure 19:
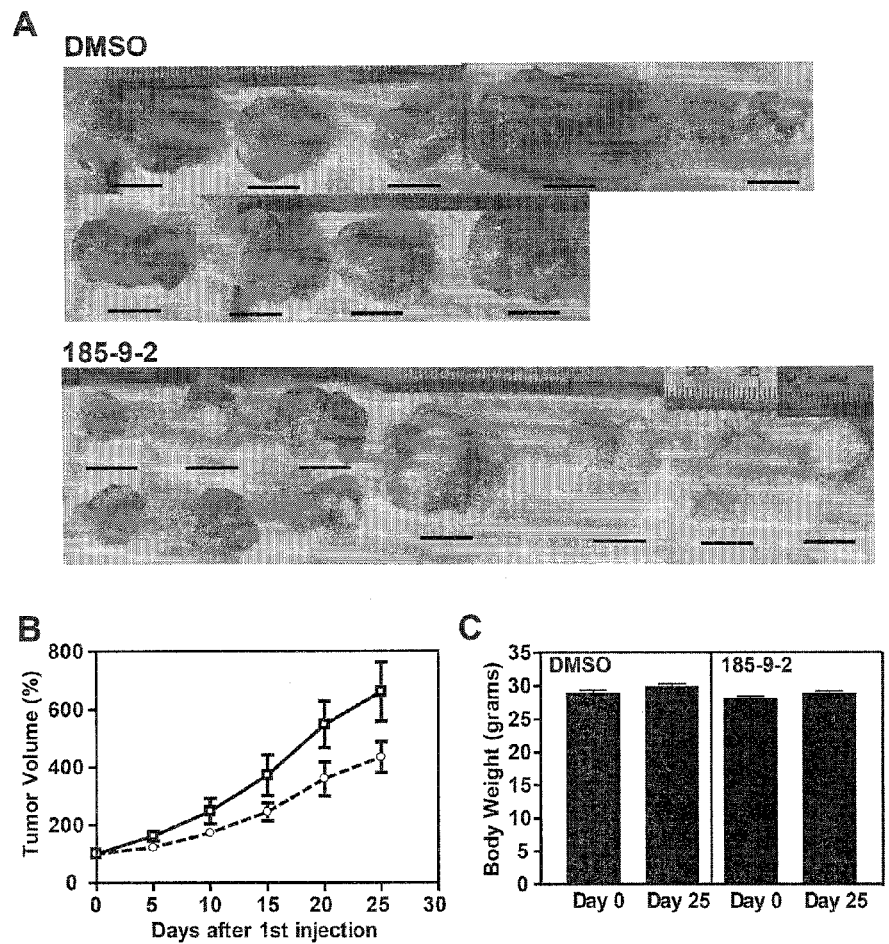
FIG. 19 A. Photographs of a representative harvested PC3 xenografts from day 25 after the 1$^{st}$ intratumorial (I.T.) injection of either DMSO (vehicle) or 185-9-2 (20 mg/kg body weight) in non-castrated animals. The black bar represents 10 mm. B. PNG01-185-017-9-2 had a small effect on PC3 tumor growth but did not reduce tumor burden. Time course showing PC3 xenograft volume over for the duration of the experiment. Tumor volume at the first injection was set to 100%. Solid line represents DMSO-treated and dashed line represents 185-9-2-treated animals. C. 185-9-2 did not reduce body weight. Body weight measured at day 0 and at the end of the experiment at day 25 in mice bearing PC3 xenografts receiving vehicle or small molecule.

The PC3 xenograft model was employed to give an indication of whether endogenous AR must be expressed for the compounds to reduce tumor burden. PC3 are human prostate cancer cells that do not express functional AR and should therefore not respond to therapy with these small molecules that have been selected for their specificity in blocking transactivation of the AR-NTD. PC3 cells were implanted subcutaneously into NOD-SCID male mice. The animals were randomized into two groups when the tumors were approximately 100 mm$^3$ (n=9 and 10; mean tumor volume=112.1±19.7 mm$^3$). Animals were treated every 5 days with a subcutaneous dose of 20 mg/kg body weight of PNG01-185-017-9-2 or matching volume of vehicle (control, DMSO). Tumor volume and body weight were measured every 5 days. In contrast to LNCaP xenografts, PNG01-185-017-9-2 did not reduce tumors but did slightly slow the growth of PC3 xenografts (FIG. 19A, B). Consistent with previous experiments shown here, no toxicity was observed as indicated by animal behavior and measured by body weight over the course of the treatments (FIG. 19C).

Example 5

Figure 20:
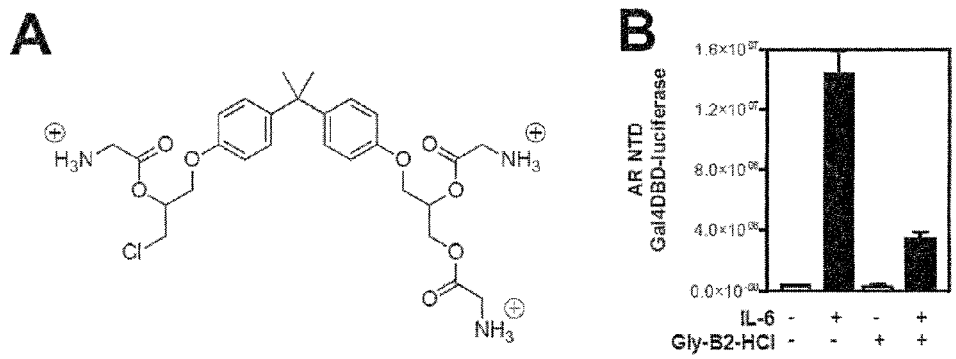
FIG. 20 Glycine ester of the BADGE.HCL.H2O (A) was tested in LNCaP cells transfected with an expression vector for the Gal4DBD-AR$_{1-558}$ chimera protein with a reporter gene containing the Gal4-binding site as cis-acting elements (p5xGal4UAS-TATA-luciferase) (B). The glycine ester, Gly-B2-HCl of 185-9-2 (25 μM) blocked IL-6 (50 ng/ml) induced transactivation of the AR NTD.

To improve the delivery of 185-9-2, a glycine ester derivative of the BADGE.HCL.H2O (FIG. 20A) was made. It is freely water soluble. This compound was submitted for cell-based testing and was observed to inhibit transactivation of the AR NTD induced by interleukin-6 (IL-6) (FIG. 20B, compare lane 2 with lane 4).

The following Table 5 includes experimental data relating to the compounds shown.

TABLE 5

| COMPOUND | EXPERIMENTAL DATA |
|---|---|
| (R)-BADGE x HI x H$_2$O (2-R) BADGE x HI x H$_2$O | 7% inhibition of Fsk activation of Gal4ARN at 20 μM<br>33% inhibition of R1881 activation of p6.1luc at 20 μM and 20% at 12.5 μM |
| Racemic BADGE x 2HCl | 79% inhibition Fsk activation of gal4ARN at 12.5 μM<br>69% inhibition of R1881 activation p6.1luc at 12.5 μM<br>63% inhibition of R1881 activation of p6.1luc at 12.5 μM |
| (R)-BADGE x 2HCl (2-R) isomers BADGE x 2HCl | 88% inhibition of Fsk activation of GalARN at 12.5 μM<br>34.8% inhibition of R1881 activation of p6.1luc<br>55% inhibition of 12.5 μM R1881 activation of p6.1luc at 12.5 μM |

TABLE 5-continued

| COMPOUND | EXPERIMENTAL DATA |
|---|---|
| 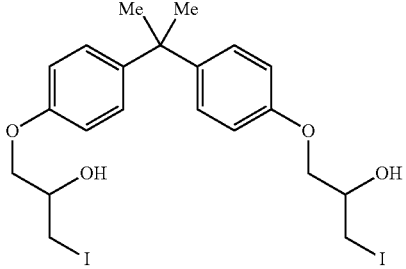<br>Racemic BADGE x 2HI | 33% inhibition of Fsk activation of Gal4ARN at 20 μM<br>35% inhibition of R1881 activation of p6.1luc at 12.5 μM<br>33% inhibition of R1881 activation of p6.1luc at 12.5 μM |
| 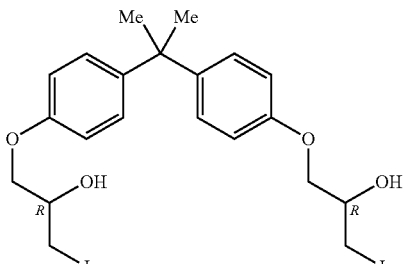<br>(R)-BADGE x 2HI<br>(2-R) Isomers BADGE x 2HI | 42% inhibition of R1881 activation of p6.1luc at 12.5 μM<br>29% inhibition of R1881 activation of p6.1luc at 12.5 μM |
| 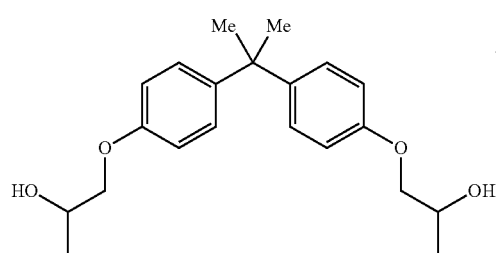<br>Commercially Purchased Compound (Aldrich)<br>PNG01-185-017-9-1<br>PNG01-185-17-9-1<br>185-9-1 | 10% inhibition of R1881 activation of ARR3luc at 50 μM |

Example 6

(R)-BAGE (1)

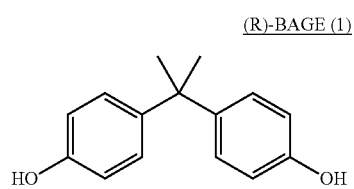

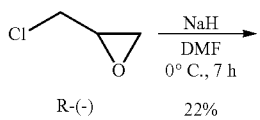

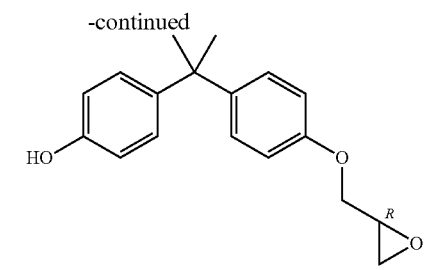

NaH as a 60% dispersion in mineral oil (96 mg, 2.40 mmol, 2.2 equiv) was suspended in anhydrous dimethyl formamide (5 mL) under argon atmosphere. The mixture was cooled to 0° C. and bisphenol A (250 mg, 1.09 mmol, 1 equiv) was added. After 15 min, (R)-epichlorohydrin (214 μL, 2.73 mmol, 2.5 equiv, 99% ee) was added via syringe and the mixture was allowed to react at room temperature for 7 h. Then, the solution was quenched with deionized water (~3 mL) and the mixture was extracted with ethyl acetate (3×3 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane and 2% methanol in dichloromethane) to provide (R)-BAGE (67 mg, 22%) as a white foamy residue.

$^1$H NMR (400 MHz, DMSO-d$_6$): δ 9.13 (s, 1H), 7.09 (d, J=8.8, 2H), 6.97 (d, J=8.4, 2H), 6.83 (d, J=8.8, 2H), 6.63 (d, J=8.8, 2H), 4.25 (dd, J=11.2, 2.8, 1H), 3.78 (dd, J=11.2, 6.4, 1H), 3.29 (m, 1H), 2.82 (t, J=4.8, 1H), 2.68 (dd, J=4.8, 2.4, 1H), 1.54 (s, 6H). $^{13}$C NMR (100 MHz, DMSO-d$_6$): δ 156.5, 155.6, 143.8, 141.3, 128.0, 127.9, 115.2, 114.4, 69.5, 50.4, 44.4, 41.7, 31.4. TLC (5% methanol in dichloromethane), Rf: 0.45 (UV, p-anisaldehyde).

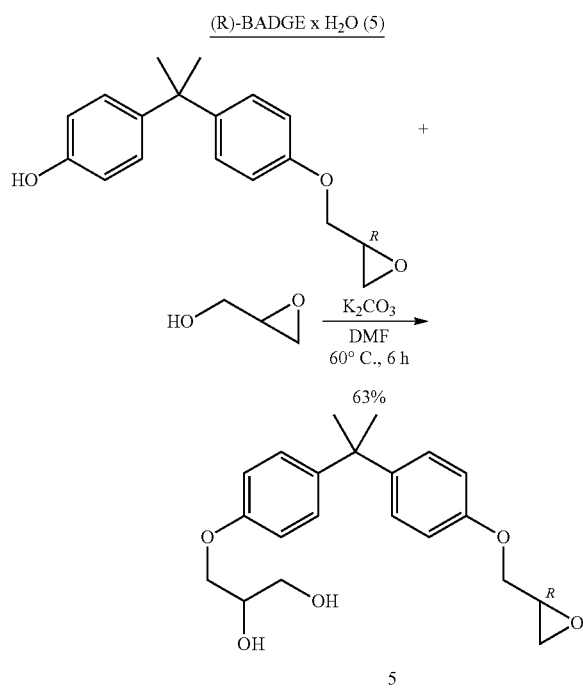

To a stirred solution of (R)-BAGE (13 mg, 0.045 mmol, 1 equiv) in anhydrous dimethyl formamide (0.3 mL) at rt was added K$_2$CO$_3$ (6 mg, 0.045 mmol, 1 equiv) and racemic glycidol (9 μL, 0.135 mmol, 3 equiv). After stirring for 6 h at 60° C., deionized water (0.2 mL) was added to the resulting orange-brown solution. The mixture was extracted with ethyl acetate (3×1 mL) The organic layer was washed with deionized water (2 mL), was dried over anhydrous magnesium sulfate, was filtered, and was concentrated under reduced pressure. The resulting residue was purified by flash column chromatography on silica gel Sep pak 2 g (eluent: dichloromethane and 5% methanol in dichloromethane) to provide (R)-BADGE×H$_2$O (10.3 mg, 63%) as a colourless oil.

$^1$H NMR (400 MHz, DMSO-d$_6$): δ 7.08 (dd, J=8.0, 5.2, 4H), 6.83 (dd, J=10.8, 8, 4H), 4.89 (d, J=5.2, 1H), 4.62 (t, J=5.6, 1H), 4.26 (dd, J=11.6, 2.8, 1H), 3.93 (dd, J=9.6, 4.0, 1H), 3.78 (m, 3H), 3.42 (t, J=5.6, 2H), 3.29 (m, 1H), 2.82 (t, J=4.8, 1H), 2.68 (dd, J =4.8, 2.4 J=11.6, 2.8, 1H), 1.57 (s, 6H). TLC (5% methanol in dichloromethane), Rf: 0.36 (UV, p-anisaldehyde).

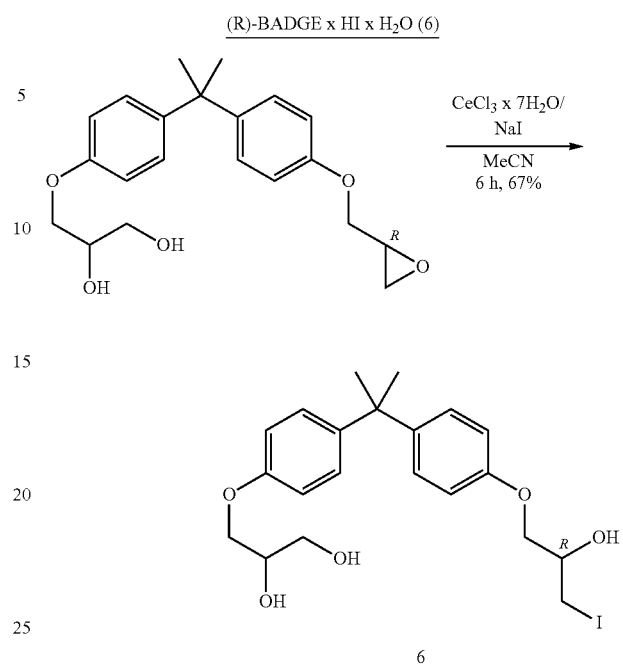

To a solution of (R)-BADGE×H$_2$O (10 mg, 0.029 mmol, 1 equiv) in acetonitrile (0.5 mL) was added CeCl$_3$.7H$_2$O (21 mg, 0.057 mmol, 2 equiv) and NaI (9 mg, 0.057 mmol, 2 equiv). After stirring for 6 h at rt, the resulting yellow suspension was concentrated under reduced pressure. The reaction mixture was dissolved with dichloromethane (2 mL) and washed with H$_2$O (3×0.5 mL), the organic layer was dried over anhydrous MgSO$_4$ and the solvent was removed under reduced pressure. The resulting residue was purified by flash column chromatography on silica gel Sep pak 2 g (eluent: dichloromethane and 10% methanol in dichloromethane) to provide (R)-BADGE×HI×H$_2$O (9 mg, 67%) as a colourless foam.

$^1$H NMR (400 MHz, DMSO-d$_6$): δ 7.09 (m, 4H), 6.81 (m, 4H), 5.52 (d, J=4.8, 1H), 4.86 (d, J=4.8, 1H), 4.59 (t, J=5.6, 1H), 3.88 (m, 3H), 3.75 (m, 3H), 3.40 (m, 3H), 3.31 (m, 1H), 1.57 (s, 6H). $^{13}$C NMR (100 MHz, DMSO-d$_6$): δ 157.1, 156.7, 143.4, 143.0, 128.0, 127.9, 114.5, 114.4, 71.4, 70.6, 70.1, 68.6, 63.4, 41.8, 31.3, 12.7. TLC (5% methanol in dichloromethane), Rf: 0.30 (UV, p-anisaldehyde).

Example 7

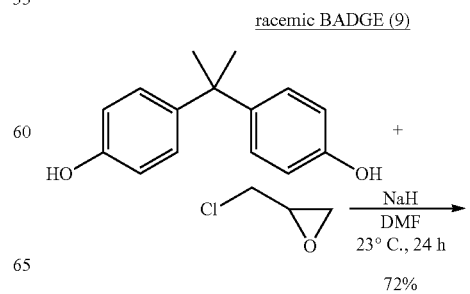

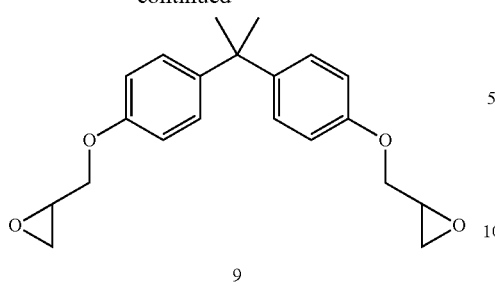

9

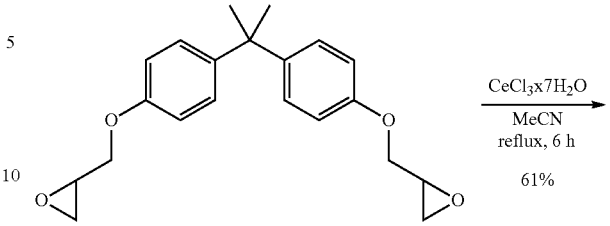

racemic BADGE x 2HCl (11)

A round-bottomed flask was charged sequentially with NaH (200 mg, 4.80 mmol, 2.2 equiv) and bisphenol A (500 mg, 2.18 mmol, 1 equiv), and the contents were placed under an atmosphere of argon. Anhydrous dimethyl formamide (5 mL) was introduced via syringe and the resulting mixture was stirred at room temperature. After 15 min, racemic epichlorohydrin (700 µL, 8.96 mmol, 4.1 equiv) was added via syringe and the mixture was allowed to react at room temperature for 18 h. Then, the solution was quenched with deionized water (~1 mL) and the mixture was extracted with ethyl acetate (3×4 mL). The organic layer was washed with deionized water (2 mL), was dried over anhydrous magnesium sulfate, was filtered, and was concentrated under reduced pressure. The resulting residue was purified by flash column chromatography on silica gel (eluent: dichloromethane) to provide racemic BADGE (536 mg, 72%) as a white foamy residue.

$^1$H NMR (400 MHz, DMSO-d$_6$): δ 7.10 (d, J=8.8, 4H), 6.84 (d, J=8.8, 4H), 4.25 (dd, J=11.6, 2.8, 2H), 3.78 (dd, J=11.2, 6.4, 2H), 3.29 (m, 2H), 2.81 (t, J=4.8, 2H), 2.68 (m, 2H), 1.60 (s, 6H). $^{13}$C NMR (100 MHz, DMSO-d$_6$): δ 156.6, 143.5, 128.0, 114.5, 69.5, 50.3, 44.4, 41.8, 31.3. TLC (5% methanol in dichloromethane), Rf: 0.77 (UV, p-anisaldehyde).

To a solution of racemic BADGE (95 mg, 0.279 mmol, 1 equiv) in acetonitrile (1.0 mL) was added CeCl$_3$.7H$_2$O (208 mg, 0.558 mmol, 2 equiv) and the mixture was refluxed for 6 h. The resulting white paste was filtered with dichloromethane and the clear suspension was concentrated under reduced pressure. The resulting residue was purified by flash column chromatography on silica gel Sep pak 2 g (eluent: dichloromethane and 10% methanol in dichloromethane) to provide racemic BADGE×2HCl (70 mg, 61%) as a colourless foam.

$^1$H NMR (400 MHz, DMSO-d$_6$): δ 7.09 (d, J=8.8, 4H), 6.83 (d, J=8.4, 4H), 5.50 (d, J=5.2, 2H), 3.99 (m, 2H), 3.92 (d, J=5.6, 4H), 3.73 (dd, J=11.2, 4.4, 2H), 3.65 (dd, J=11.2, 5.6, 2H), 1.57 (s, 6H). $^{13}$C NMR (100 MHz, DMSO-d$_6$): δ 156.7, 143.4, 128.0, 114.5, 69.5, 69.3, 47.4, 41.8, 31.3. TLC (5% methanol in dichloromethane), Rf: 0.31 (UV, p-anisaldehyde).

Example 8

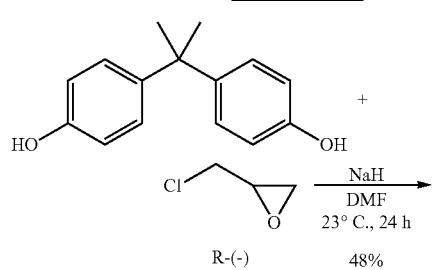

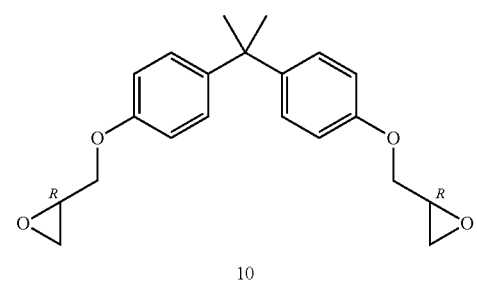

10

Same procedure as previously described for racemic BADGE, but using (R)-epichlorohydrin.

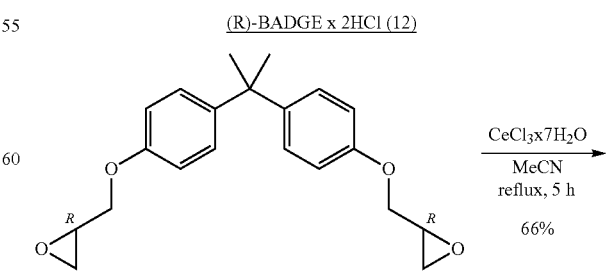

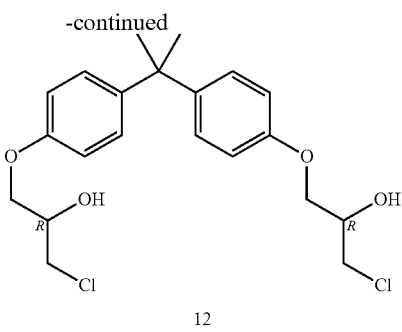

12

Same procedure as previously described for racemic BADGE×2HCl, but using (R)-BADGE as starting material.

Example 9

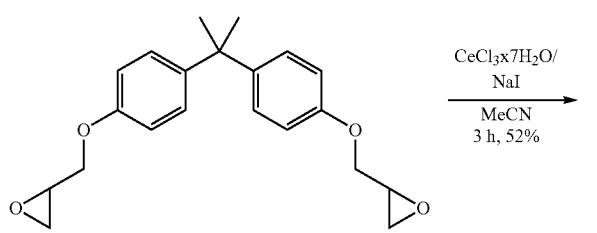

13

To a solution of racemic BADGE (60 mg, 0.176 mmol, 1 equiv) in acetonitrile (1.0 mL) was added CeCl₃.7H₂O (131 mg, 0.352 mmol, 2 equiv) and NaI (53 mg, 0.352 mmol, 2 equiv). After stirring for 3 h at rt, the resulting yellow suspension was concentrated under reduced pressure. The reaction mixture was dissolved with dichloromethane (3 mL) and washed with H₂O (3×1 mL), the organic layer was dried over anhydrous magnesium sulfate and the solvent was removed under reduced pressure. The resulting residue was purified by flash column chromatography on silica gel Sep pak 2 g (eluent: dichloromethane and 10% methanol in dichloromethane) to provide racemic BADGE×2HI (55 mg, 52%) as a brown foam.

$^1$H NMR (400 MHz, DMSO-d$_6$): δ 7.09 (d, J=8.8, 4H), 6.82 (d, J=8.8, 4H), 5.53 (d, J=5.2, 2H), 3.87 (m, 4H), 3.71 (m, 2H), 3.40 (dd, J=10.4, 4.8, 2H), 3.31 (m, 2H), 1.57 (s, 6H). $^{13}$C NMR (100 MHz, DMSO-d$_6$): δ 156.7, 143.5, 128.1, 114.5, 71.4, 68.6, 41.8, 31.3, 12.7. TLC (5% methanol in dichloromethane), Rf: 0.43 (UV, p-anisaldehyde).

Example 10

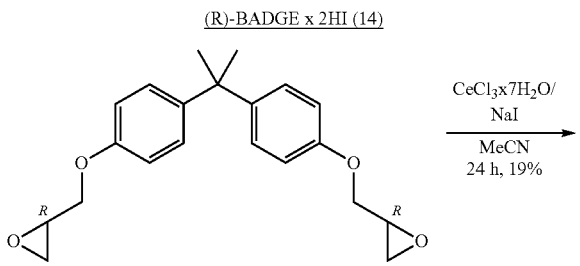

14

Same procedure as previously described for racemic BADGE×2HI, but using (R)-BADGE as starting material.

Example 11

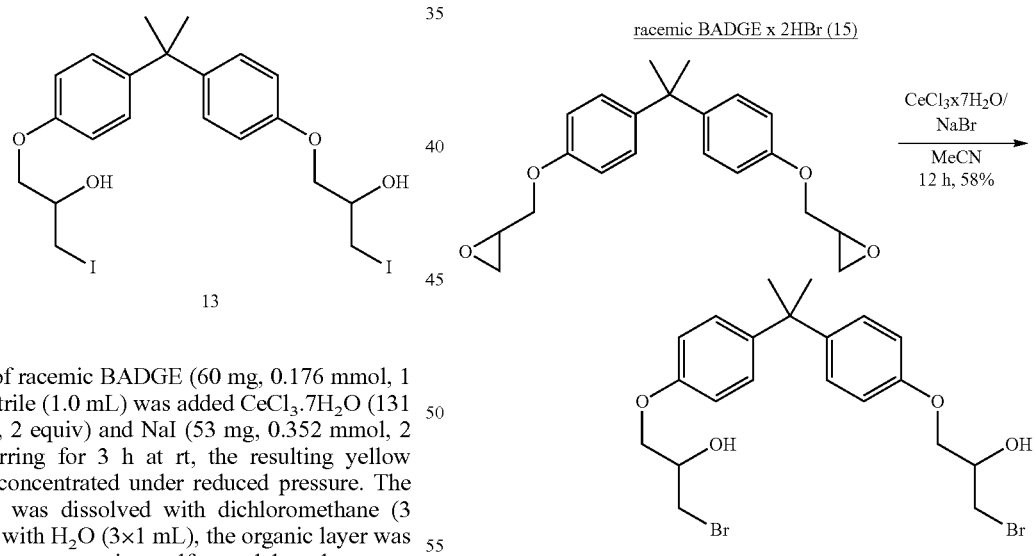

15

To a solution of racemic BADGE (60 mg, 0.176 mmol, 1 equiv) in acetonitrile (1.0 mL) was added CeCl₃.7H₂O (131 mg, 0.352 mmol, 2 equiv) and NaBr (36 mg, 0.352 mmol, 2 equiv). After stirring overnight at rt, the suspension was filtered with dichloromethane (6 mL) and washed with H₂O (3×2 mL), the organic layer was dried over anhydrous magnesium sulfate and the solvent was removed under reduced pressure. The resulting residue was purified by flash column chromatography on silica gel Sep pak 2 g (eluent:

dichloromethane and 5 to 10% methanol in dichloromethane) to provide racemic BADGE x 2HBr (33 mg, 58%) as a colourless foam.

$^1$H NMR (400 MHz, DMSO-d$_6$): δ 7.09 (d, J=8.4, 4H), 6.83 (d, J=8.8, 4H), 5.54 (d, J=5.2, 2H), 3.98 (m, 2H), 3.93 (d, J=5.6, 4H), 3.62 (dd, J=10.0, 4.4, 2H), 3.53 (dd, J=10.4, 5.2, 2H), 1.57 (s, 6H). $^{13}$C NMR (100 MHz, DMSO-d$_6$): δ 156.7, 143.5, 128.1, 114.5, 70.2, 68.8, 41.8, 37.2, 31.3. TLC (5% methanol in dichloromethane), Rf: 0.53 (UV, p-anisaldehyde).

Example 12 racemic BADGE x 2HF (16)

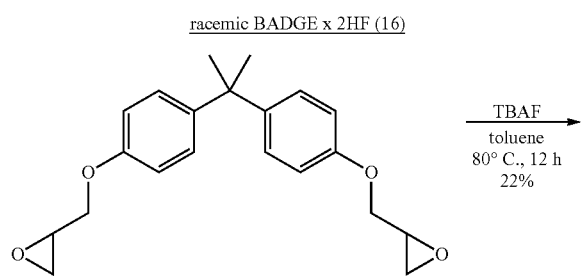

TBAF
toluene
80° C., 12 h
22%

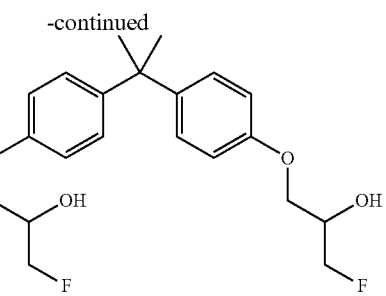

16

To a solution of racemic BADGE (60 mg, 0.176 mmol, 1 equiv) in anhydrous toluene (1.0 mL) was added 1M solution of TBAF in THF (0.88 mL, 0.88 mmol, 5 equiv), and the mixture was allowed to stir at 80° C. for 12 h. The mixture was subjected to a short path column chromatography (eluent: dichloromethane and 5% methanol in dichloromethane) to remove TBAF. The resulting residue was purified by flash column chromatography on silica gel Sep pak 2 g (eluent: 30% ethyl acetate in hexane) to provide racemic BADGE×2HF (14 mg, 22%) as a colourless foam.

$^1$H NMR (400 MHz, DMSO-d$_6$): δ 7.09 (d, J=8.4, 4H), 6.82 (d, J=8.8, 4H), 5.40 (d, J=5.2, 2H), 4.50 (ddd, J=47.6, 9.6, 3.6, 2H), 4.39 (ddd, J=47.6, 9.6, 3.6, 2H), 3.99 (dm, J=20.8, 2H), 3.90 (m, 4H), 1.56 (s, 6H). $^{19}$F NMR (282.4 MHz, DMSO-d$_6$): δ −230.4 (td, J=50.4, 22.2). TLC (5% methanol in dichloromethane), Rf: 0.38 (UV, p-anisaldehyde).

Example 13

Synthesis of the triglycine ester 3 of BADGE·HCl, H$_2$O

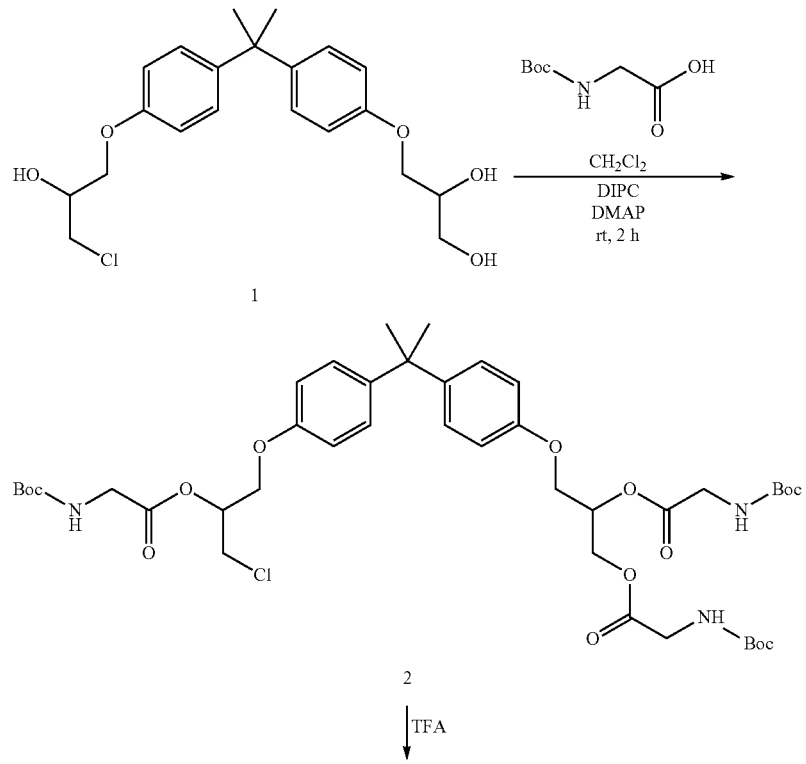

TFA

-continued

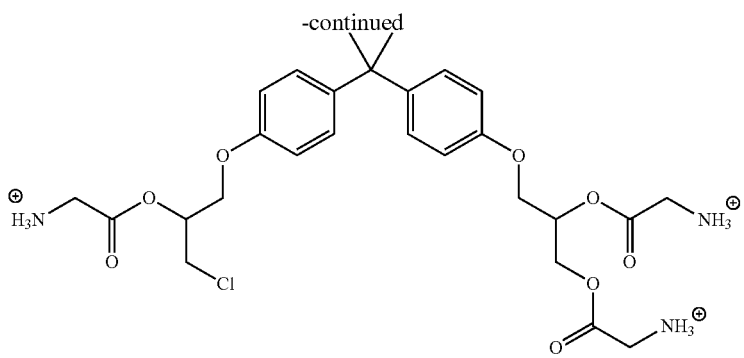

3

Experimental for synthesis of the TFA salt 3 of Tri-Gly-Badge, HCL.H2O (1): To a solution of BADGE.HCL.H$_2$O (1) (8.80 mg, 0.02 mmol) in 1mL of CH$_2$Cl$_2$ was added BOC-GLy-OH (30.8 mg, 0.18 mmol), DMAP (catalytic amount), and DIPC (0.03 mL, 0.18 mmol). The mixture was stirred at room temperature for two hours and then filtered. The filtrate was added to 2 mL of TFA, stirred at room temperature for 2 hours, and then concentrated in vacuo. The residue was partitioned between EtOAc and water and the water layer was concentrated, dried, and then passed through a LH-20 column (elueted with 100% MeOH) to give pure product 3. After the TFA salt product was concentrated, it was dissolved in 2 mL of MeOH, then 2 mL of 2N HCL was added. The mixture was stirred at room temperature for 5 min, concentrated under an N$_2$ stream, and then dried on vacuum for overnight to give the HCl salts.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:
1. A method for modulating androgen receptor (AR) activity for treatment of at least one indication selected from the group consisting of: prostate cancer, breast cancer, ovarian cancer, endometrial cancer, hair loss, acne, hirsutism, ovarian cysts, polycystic ovary disease, precocious puberty, and age-related macular degeneration; wherein, the method comprises administering to a mammalian cell a compound having a structure of Formula II:

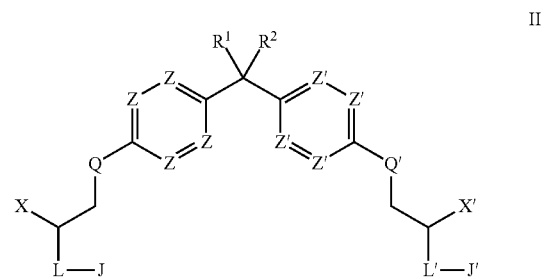

II wherein:
J and J' are each independently H or a moiety selected from:

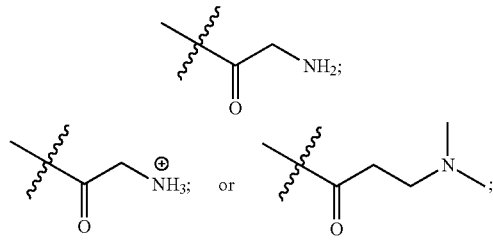

L is O, S, NH, NG, N$^+$H$_2$, or N$^+$HG;
X is H, CH$_3$, CH$_2$F, CHF$_2$, CF$_3$, CHCl$_2$, CCl$_3$, CH$_2$Br, CHBr$_2$, CBr$_3$, CH$_2$I, CHI$_2$, CI$_3$, CH$_2$OJ''', CH$_2$OG, CH$_2$OGOG', GOG', GOG'OG'', CH$_2$SG, CH$_2$NH$_2$, CH$_2$NHG, or CH$_2$NG$_2$;
Q is G, O, CH$_2$, CHG, CG$_2$, S, NH or NG;
each Z is independently N, CH, COH, C—(C$_1$-C$_{10}$ aromatic cyclic or non-aromatic cyclic), C—(C$_1$-C$_{10}$ substituted or unsubstituted unsaturated), CO—(C$_1$-C$_{10}$ aromatic cyclic or non-aromatic cyclic), CO—(C$_1$-C$_{10}$ substituted or unsubstituted unsaturated),CNH$_2$, CNHG, CNG$_2$, COSO$_3$H, COPO$_3$H$_2$; CSG, CSOG, or CSO$_2$G;
R$^1$ and R$^2$ are each independently H, or a branched or unbranched, substituted or unsubstituted C$_1$-C$_{10}$ alkyl or together form a substituted or unsubstituted, saturated, aromatic cyclic or non-aromatic cyclic C$_3$-C$_{10}$ alkyl;

each G, G' and G" is independently a branched, unbranched, or aromatic cyclic or non-aromatic cyclic, substituted or unsubstituted, saturated or unsaturated $C_1$-$C_{10}$ alkyl;

J''' is H or a moiety selected from:

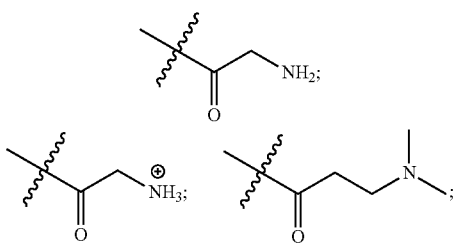

L' is O, S, NH, NG, $N^+H_2$, or $N^+HG$;
each Z' is independently N, CH, C—($C_1$-$C_{10}$ aromatic cyclic or non-aromatic cyclic), C—($C_1$-$C_{10}$ substituted or unsubstituted unsaturated), CO—($C_1$-$C_{10}$ aromatic cyclic or non-aromatic cyclic), CO—($C_1$-$C_{10}$ substituted or unsubstituted unsaturated), $CNH_2$, CNHG, $CNG_2$, $COSO_3H$, $COPO_3H_2$; CSG, CSOG, or $CSO_2G$;
Q' is G, O, $CH_2$, CHG, $CG_2$, S, NH or NG;
X' is H, $CH_3$, $CH_2F$, $CHF_2$, $CF_3$, $CH_2Cl$, $CHCl_2$, $CCl_3$, $CH_2Br$, $CHBr_2$, $CBr_3$, $CH_2I$, $CHI_2$, $CI_3$, G, $CH_2OG$, or $CH_2OGOG'$;
wherein the optional substituent is selected from the group consisting of: oxo, OJ''', COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R is an unsubstituted $C_1$-$C_{10}$ alkyl.

2. The method of claim 1, wherein X is $CH_2F$, $CH_2Br$, $CH_2I$, $CH_2OG$, $CH_2OGOG'$, $CH_2SG$, $CH_2NH_2$, $CH_2NHG$, or $CH_2NG_2$; and
each Z is independently N, CH, or COH and each Z' is independently N or CH.

3. The method of claim 1, wherein each Z and Z' is CH.
4. The method of claim 1, wherein each of Q and Q' are O.
5. The method of claim 1, wherein each of $R^1$ and $R^2$ are independently H, or a branched or unbranched, substituted or unsubstituted, $C_1$-$C_{10}$ alkyl.
6. The method of claim 1, wherein each $R^1$ and $R^2$ is $CH_3$.
7. The method of claim 1, wherein X is H, $CH_3$, $CH_2F$, $CH_2Br$, $CH_2I$, $CH_2OJ'''$, $CH_2OG$, or $CH_2OGOG'$.
8. The method of claim 1, wherein X is $CH_2F$, $CH_2I$, $CH_2Br$, $CH_2OH$, $CH_2OCH_3$, or $CH_2O$(isopropyl), or $CH_2OC_2H_4OC_4H_9$.
9. The method of claim 1, wherein X' is H, $CH_3$, $CH_2F$, $CH_2Cl$, $CH_2Br$, $CH_2I$, $CH_2OG$, $CH_2OGOG'$, GOG', GOG'OG", $CH_2SG$, $CH_2NH_2$, $CH_2NHG$, or $CH_2NG_2$.
10. The method of claim 1, wherein X' is H, $CH_3$, $CH_2F$, $CH_2Cl$, $CH_2Br$, $CH_2I$, $CH_2OG$, or $CH_2OGOG'$.
11. The method of claim 1, wherein X' is $CH_2Cl$, $CH_2F$, $CH_2I$, $CH_2Br$, $CH_2OCH_3$, $CH_2O$(isopropyl), or $CH_2OC_2H_4OC_4H_9$.
12. The method of claim 1, wherein each J, J', and J''', when present is

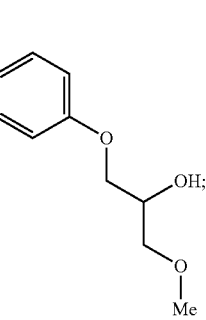

13. The method of claim 1, wherein each J, J' J''', when present, is H.
14. The method of claim 1, wherein each L and L', when present, is independently O, or S.
15. The method of claim 1, wherein each L and L', when present, is O.
16. The method of claim 1, wherein the compound is selected from one or more of the following:

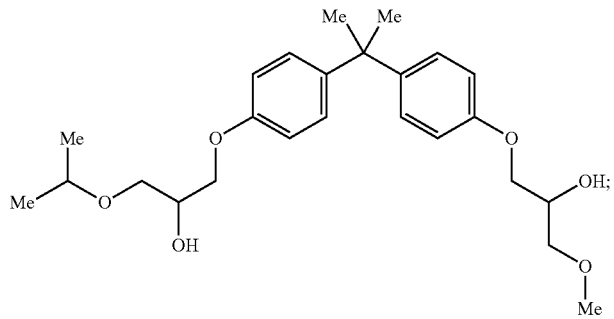

-continued
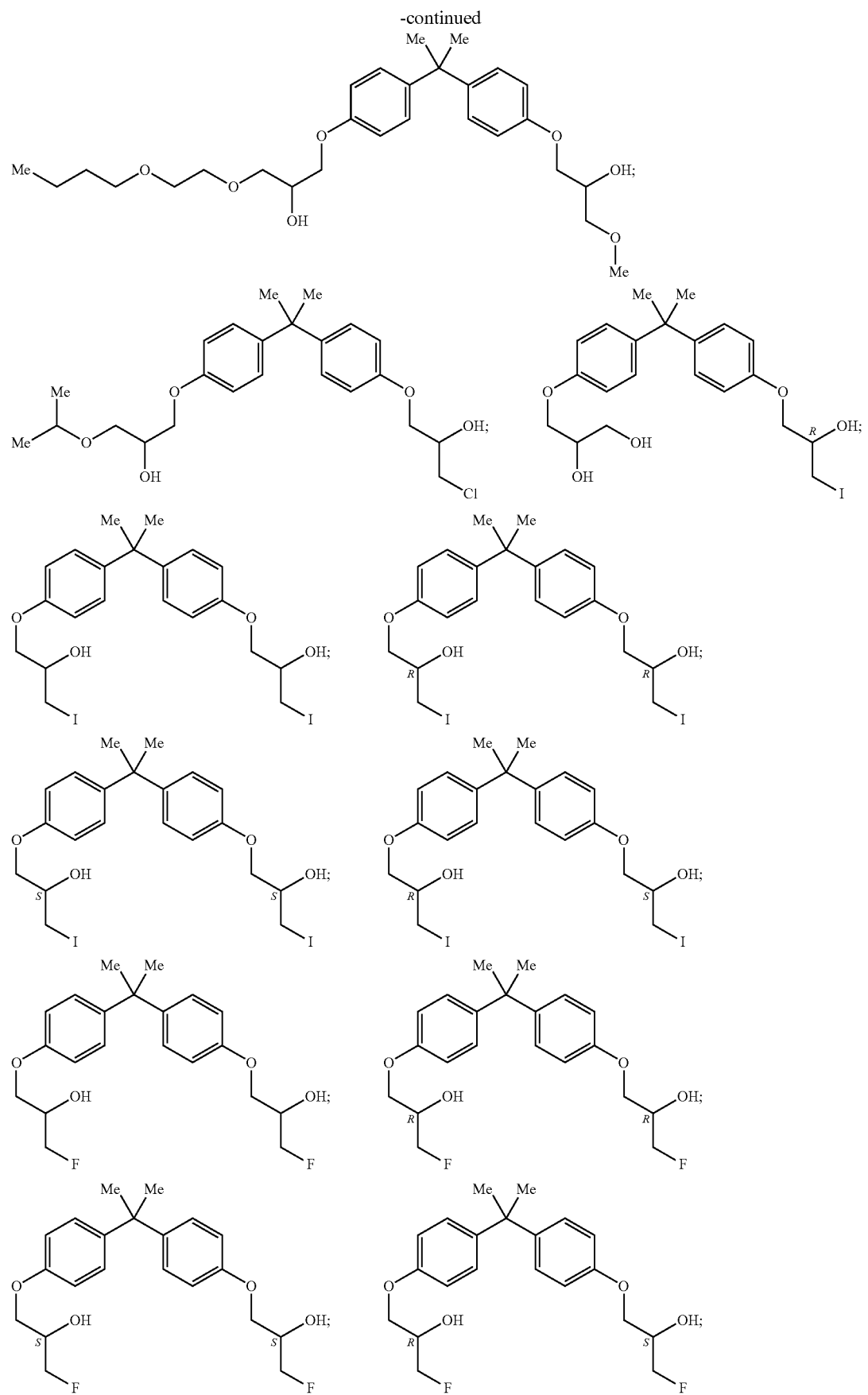

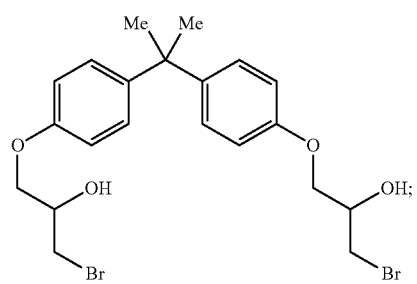 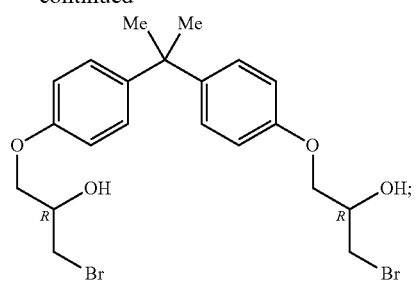
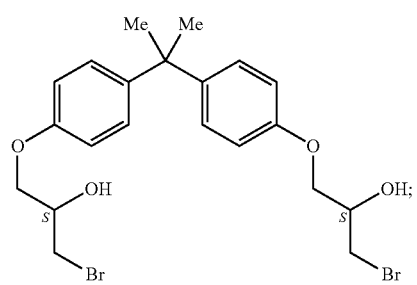 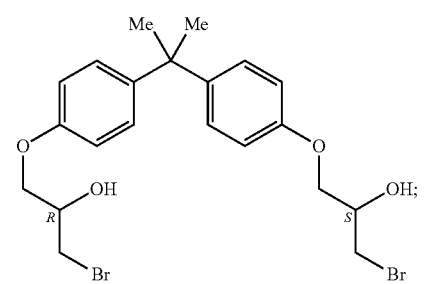
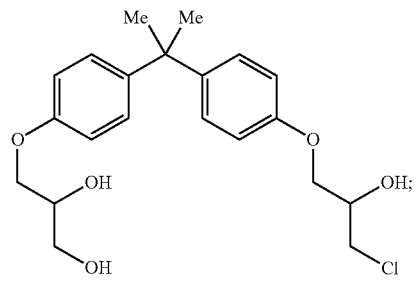 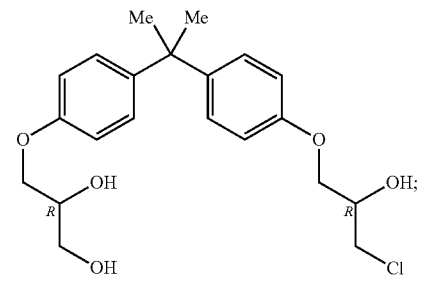
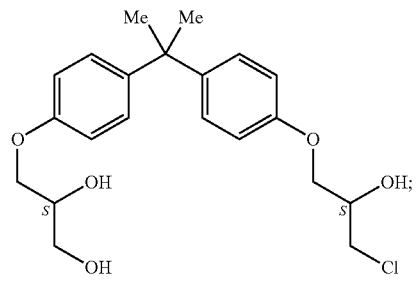 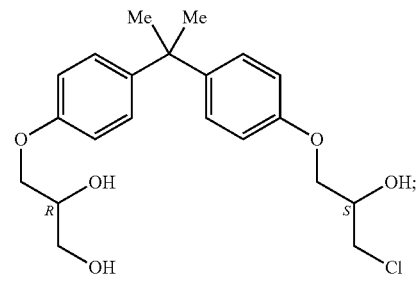
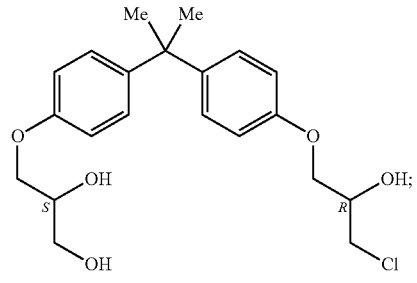 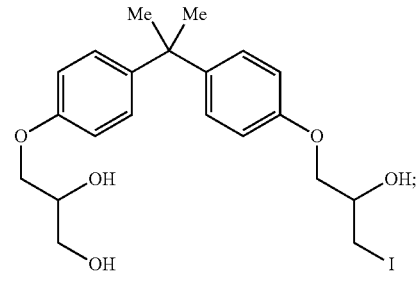
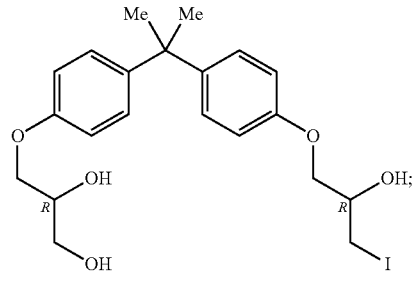 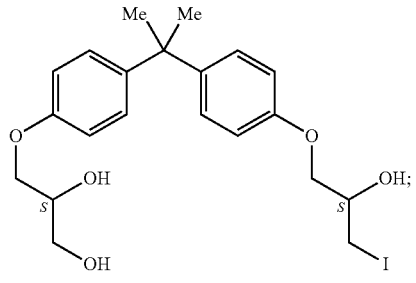

-continued
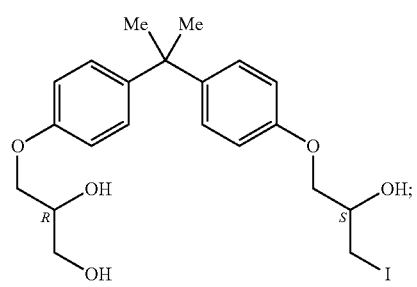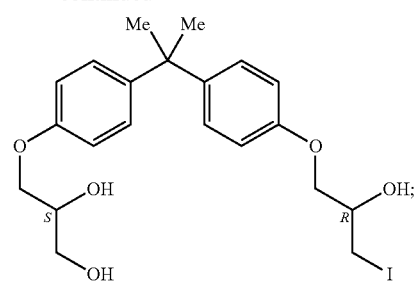
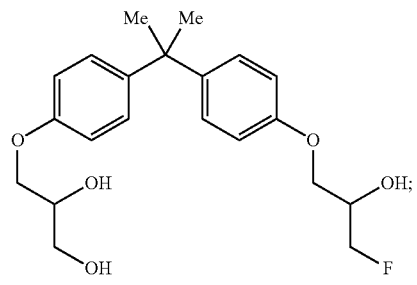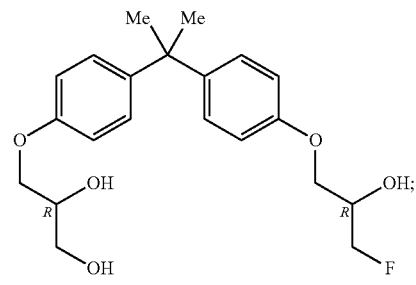
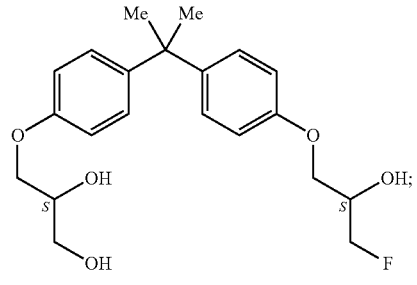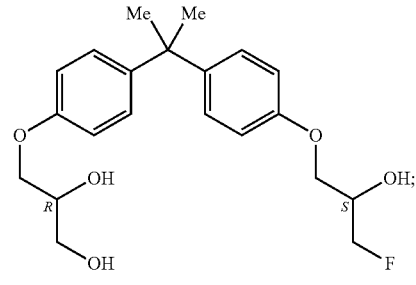
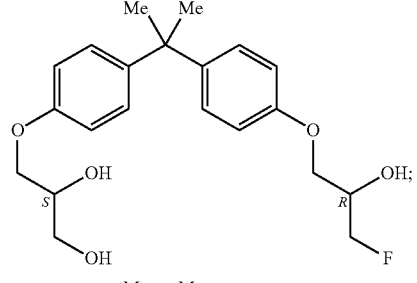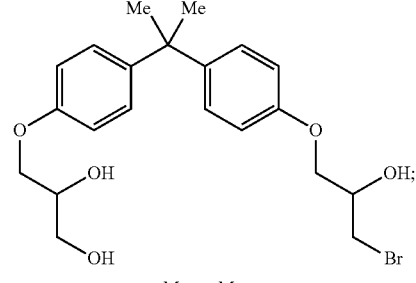
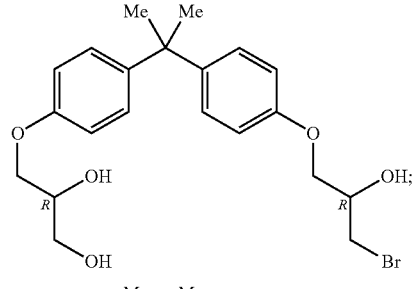and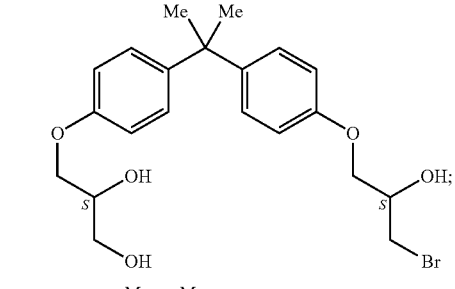
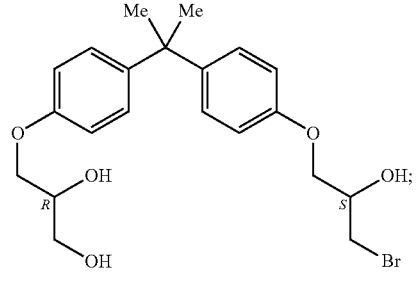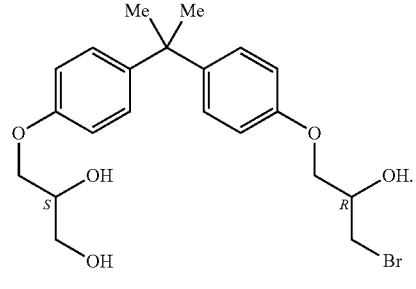

17. The method of claim 1, wherein the mammalian cell is a human cell.

18. The method of claim 1, wherein the modulating AR activity is for inhibiting AR N-terminal domain activity.

19. The method of claim 1, wherein the modulating is in vivo.

20. The method of claim 1, wherein the indication is prostate cancer.

21. The method of claim 20, wherein the prostate cancer is androgen-independent prostate cancer.

22. The method of claim 20, wherein the prostate cancer is androgen-dependent prostate cancer.

23. The method of claim 1, wherein:
L is O, NH, NG, $N^+H_2$, or $N^+HG$; and
L' is O, NH, NG, $N^+H_2$, or $N^+HG$.

24. The method of claim 1, wherein X' is $CH_3$, $CH_2F$, $CH_2Cl$, $CH_2Br$, $CH_2I$, $CH_2OCH_3$, $CH_2O$(isopropyl), or $CH_2OC_2H_4OC_4H_9$.

25. The method of claim 1, wherein each L and L', when present, is independently O, NH or N+$H_2$.

26. A compound having a structure of Formula II

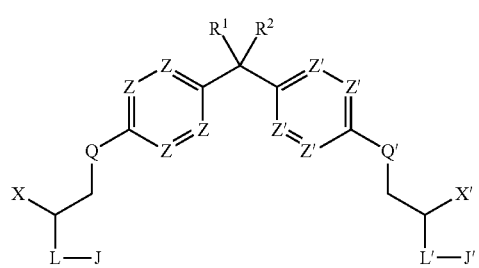

wherein
each J and J' is independently H or a moiety selected from:

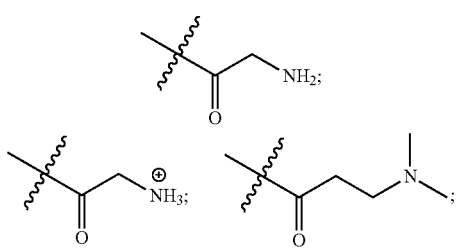

each L and L' is independently O, NH, NG, $N^+H_2$ or $N^+HG$;
each Q and Q' is independently G, O, $CH_2$, CHG, $CG_2$, S, NH or NG;
each Z and Z' is independently N, CH, COH, CF, CCl, CBr, CI, $CNH_2$, CNHG, $CNG_2$, $COSO_3H$, $COPO_3H_2$; CSG, CSOG, or $CSO_2G$;
$R^1$ and $R^2$ are each independently H; or a branched or unbranched, substituted or unsubstituted $C_1$-$C_{10}$ alkyl or together form a substituted or unsubstituted, saturated, aromatic cyclic or non-aromatic cyclic $C_3$-$C_{10}$ alkyl;
X is $CH_2O$(isopropyl), $CH_2OC_2H_4OC_4H_9$, $CH_2SG$, $CH_2NH_2$, $CH_2NHG$, $CH_2I$, $CH_2Br$, $CH_2F$, or $CH_2NG_2$;
X' is H, $CH_3$, $CH_2F$, $CHF_2$, $CF_3$, $CH_2Cl$, $CHCl_2$, $CCl_3$, $CHI_2$, $CI_3$, $CH_2F$, $CHF_2$, $CF_3$, $CH_2OJ'''$, $CH_2OG$, $GOG'$, $CH_2SG$, $CH_2NH_2$, $CH_2NHG$ or $CH_2NG_2$;

J''' is independently H or a moiety selected from:

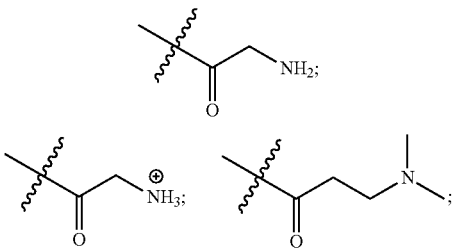

each G and G' is independently, a branched or unbranched, non-aromatic cyclic, substituted or unsubstituted, saturated $C_1$-$C_{10}$ alkyl;
wherein the optional substituent is selected from the group consisting of: oxo, $OJ'''$, COOH, R, OH, OR, F, Cl, Br, I, $NH_2$, NHR, $NR_2$, CN, SH, SR, $SO_3H$, $SO_3R$, $SO_2R$, $OSO_3R$, and $NO_2$ wherein R is an unsubstituted $C_1$-$C_{10}$ alkyl; and
wherein X' is not —$CH_2O(CH_2)_2$—O—$(CH_2)_3CH_3$, —$CH_2O(CH_2)_2CH_3$, —$CH_2O(CH_2)_3CH_3$ or —$CH_2O(CH_2)_3$—O—$CH_3$; and
wherein X is not —$CH_2O(CH_2)_2$—O—$(CH_2)_3CH_3$ when X' is $CH_2OH$.

27. The compound of claim 26 wherein X' is H, $CH_3$, $CH_2F$, $CH_2Cl$, $CH_2OG$, $GOG'$, $CH_2SG$, $CH_2NH_2$, $CH_2NHG$ or $CH_2NG_2$; and
each Z and Z' is independently N, CH or COH.

28. The compound of claim 26, wherein each Z and Z' is CH.

29. The compound of claim 26, wherein each of Q and Q' are O.

30. The compound of claim 26, wherein each of $R^1$ and $R^2$ are independently H, or a branched or unbranched, substituted or unsubstituted $C_1$-$C_{10}$ alkyl.

31. The compound of claim 26, wherein each $R^1$ and $R^2$ is $CH_3$.

32. The compound of claim 26, wherein X is $CH_2I$, $CH_2Br$, $CH_2F$, or $CH_2O$(isopropyl).

33. The compound of claim 26, wherein X' is H, $CH_3$, $CH_2F$, $CH_2Cl$, $CH_2OG$, $GOG'$, $CH_2SG$, $CH_2NH_2$, $CH_2NHG$, or $CH_2NG_2$.

34. The compound of claim 26, wherein X' is H, $CH_3$, $CH_2F$, $CH_2Cl$, or $CH_2OG$.

35. The compound of claim 26, wherein X' is $CH_2F$, $CH_2Cl$ or $CH_2OG$.

36. The compound of claim 26, wherein X' is $CH_2F$, $CH_2Cl$, $CH_2OCH_3$ or $CH_2O$(isopropyl).

37. The compound of claim 26, wherein each J, J' and J''', when present, is H.

38. The compound of claim 26, wherein each L and L', when present, is independently O, NH or $N^+H_2$.

39. The compound of claim 26, wherein each L and L', when present, is O.

40. The compound of claim 26 wherein the compound is selected from one or more of the following:

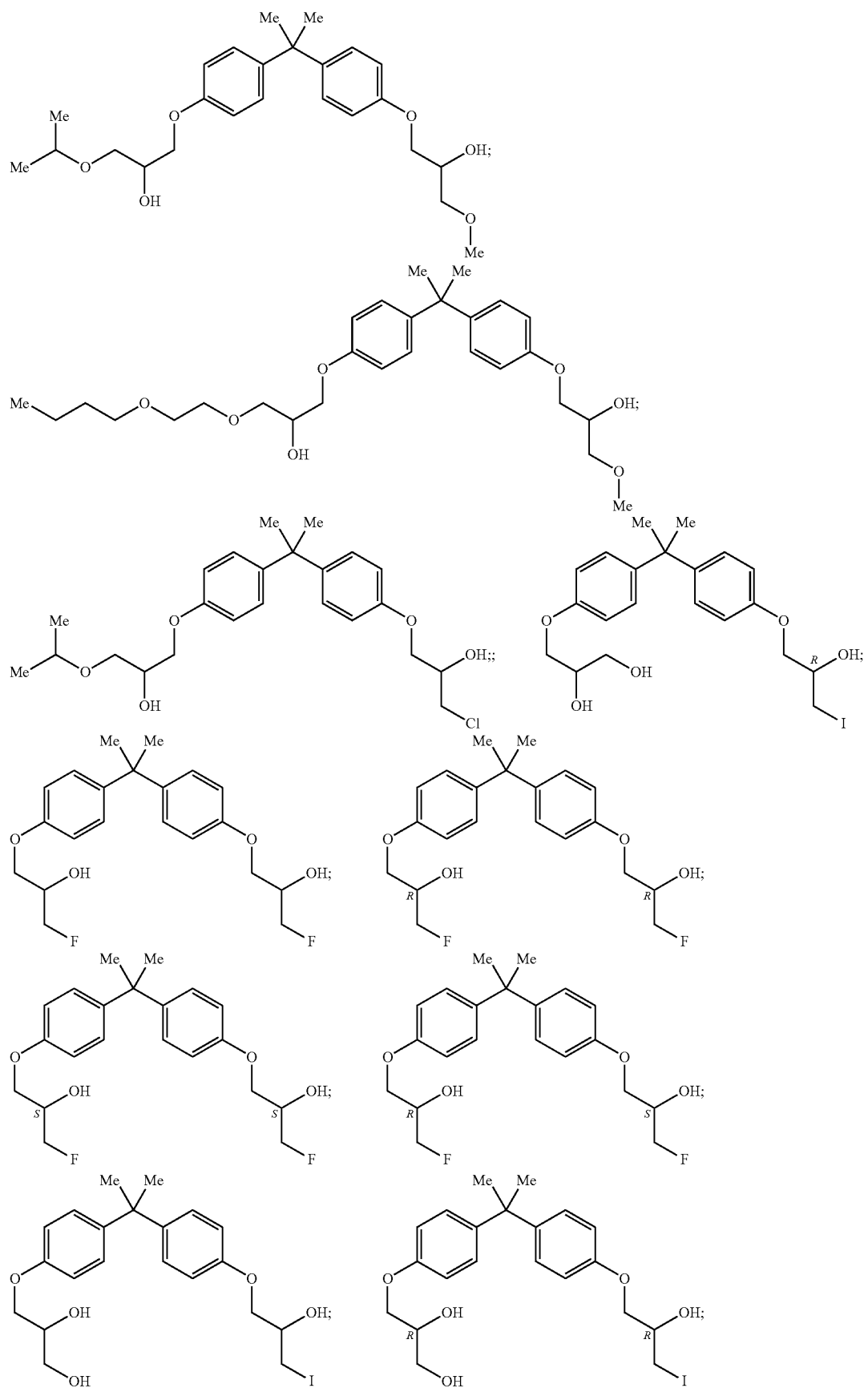

-continued
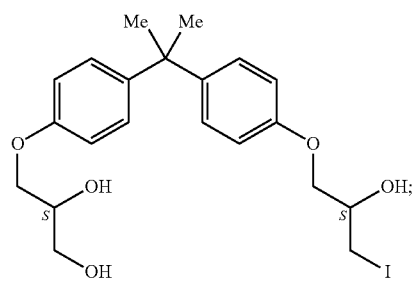
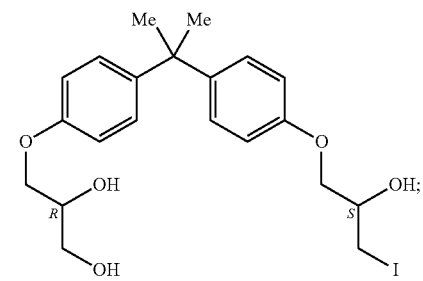
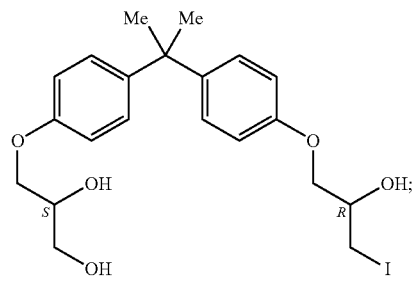
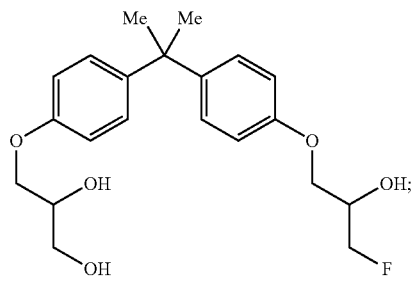
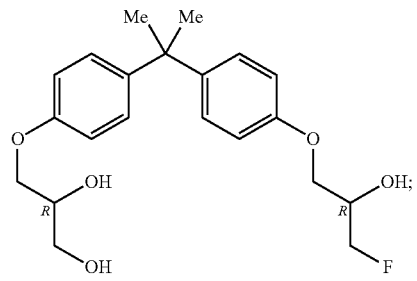
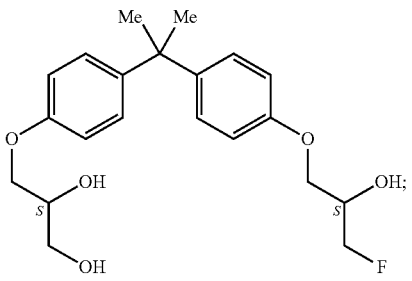
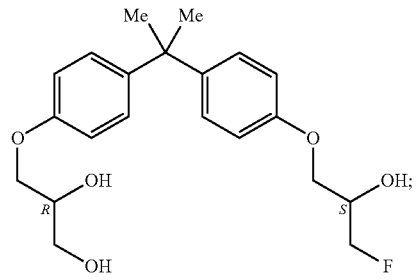
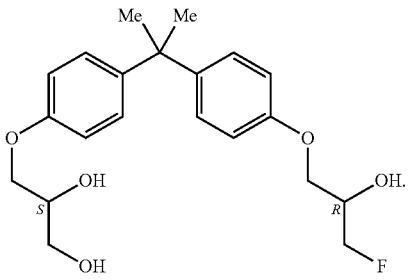
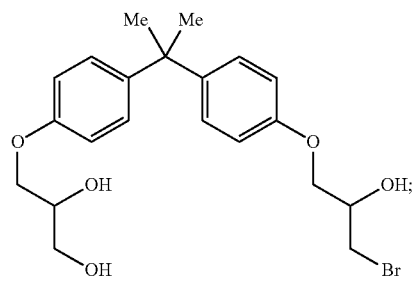
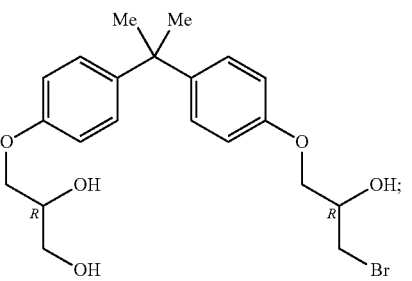
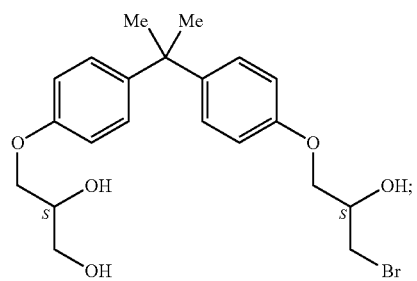
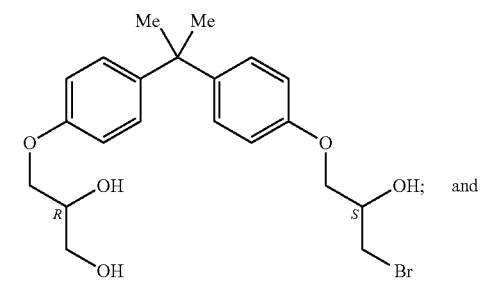

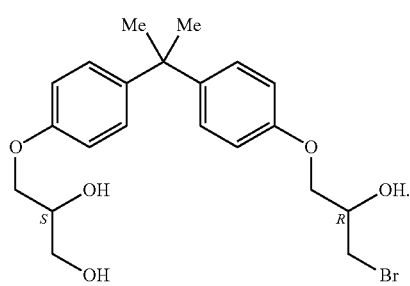

41. A pharmaceutical composition comprising a compound according to claim 26 and a pharmaceutically acceptable excipient.

42. A pharmaceutical composition comprising a compound having a structure of Formula II

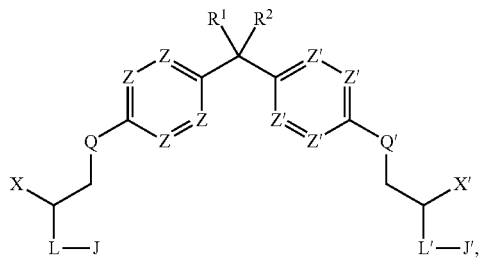

wherein

J and J' are each independently H or a moiety selected from:

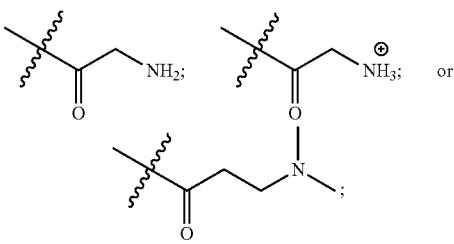

is H or a moiety selected from:

L is O, S, NH, NG, N$^+$H$_2$, or N$^+$HG;

X is H, CH$_3$, CH$_2$F, CHF$_2$, CF$_3$, CH$_2$Cl, CHCl$_2$, CCl$_3$, CH$_2$Br, CHBr$_2$, CBr$_3$, CH$_2$I, CHI$_2$, CI$_3$, CH$_2$OJ''', CH$_2$OG, CH$_2$OGOG', GOG', GOG'OG'', CH$_2$SG, CH$_2$NH$_2$, CH$_2$NHG, or CH$_2$NG$_2$;

Q is G, O, CH$_2$, CHG, CG$_2$, S, NH or NG;

each Z is independently N, CH, COH, CF, CCl, CBr, CI, CNH$_2$, CNHG, CNG$_2$, COSO$_3$H, COPO$_3$H$_2$; CSG, CSOG, or CSO$_2$G;

R$^1$ and R$^2$ are each independently H, or a branched or unbranched, substituted or unsubstituted C$_1$-C$_{10}$ alkyl or together form a substituted or unsubstituted, saturated, aromatic cyclic or non-aromatic cyclic C$_3$-C$_{10}$ alkyl;

each G, G', and G''' is independently a branched or unbranched, aromatic cyclic or non-aromatic cyclic, substituted or unsubstituted, saturated or unsaturated C$_1$-C$_{10}$ alkyl;

L' is O, S, NH, NG, N$^+$H$_2$, or N$^+$HG;

each Z' is independently N, CH, COH, C—(C$_1$-C$_{10}$ aromatic cyclic or non-aromatic cyclic), C—(C$_1$-C$_{10}$ substituted or unsubstituted unsaturated), CO—(C$_1$-C$_{10}$ aromatic cyclic or non-aromatic cyclic), CO—(C$_1$-C$_{10}$ substituted or unsubstituted unsaturated),CNH$_2$, CNHG, CNG$_2$, COSO$_3$H, COPO$_3$H$_2$; CSG, CSOG, or CSO$_2$G;

Q' is G, O, CH$_2$, CHG, CG$_2$, S, NH or NG;

X' is CH$_2$Cl, or CH$_2$Br, wherein the optional substituent is selected from the group consisting of: oxo, OJ''', COOH, R, OH, OR, F, Cl, Br, I, NH$_2$, NHR, NR$_2$, CN, SH, SR, SO$_3$H, SO$_3$R, SO$_2$R, OSO$_3$R, and NO$_2$ wherein R is an unsubstituted C$_1$-C$_{10}$ alkyl;

and a pharmaceutically acceptable excipient.

43. A compound selected from one the following:

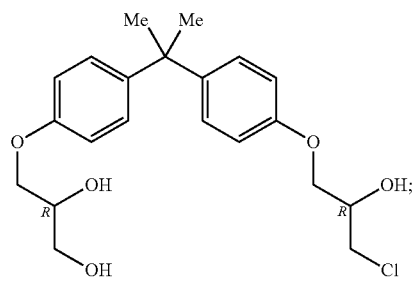

111
-continued
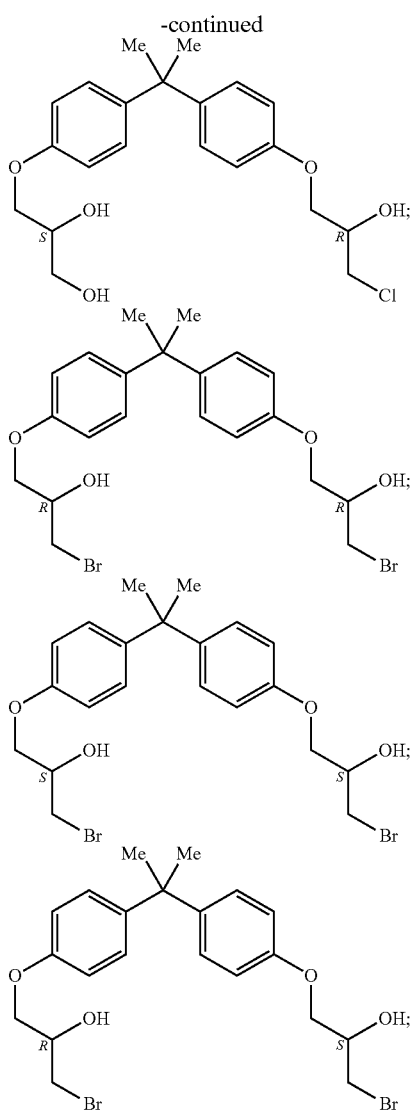
112
-continued
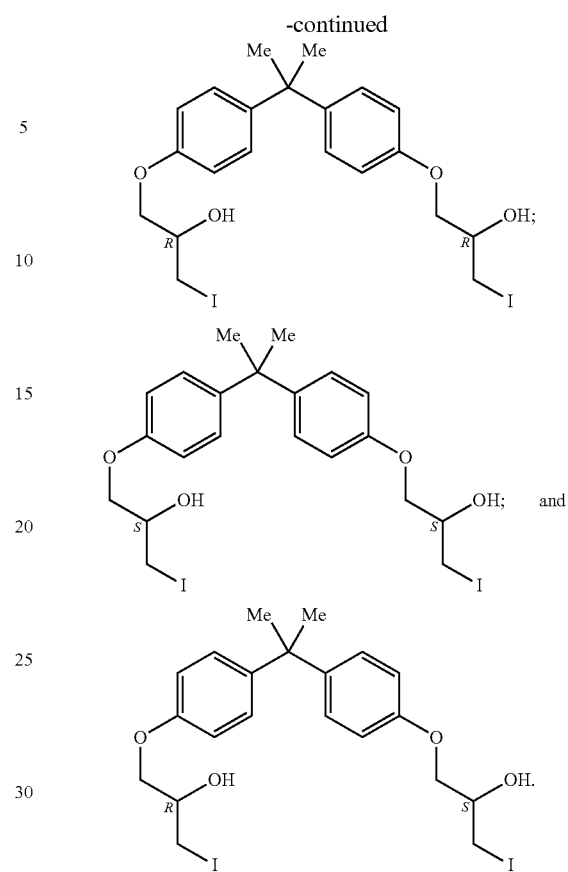
44. A pharmaceutical composition comprising a compound according to claim 43 and a pharmaceutically acceptable excipient.
45. A method for modulating androgen receptor (AR) activity, the method comprising administering to a mammalian cell a compound of claim 43.
* * * * *

UNITED STATES PATENT AND TRADEMARK OFFICE
CERTIFICATE OF CORRECTION

PATENT NO. : 9,862,667 B2  Page 1 of 1
APPLICATION NO. : 12/999037
DATED : January 9, 2018
INVENTOR(S) : Marianne Dorothy Sadar et al.

It is certified that error appears in the above-identified patent and that said Letters Patent is hereby corrected as shown below:

In Claim 13 at Column 96, Lines 31-32, "The method of claim 1, wherein each J, J' J'", when present, is H." should appear as --The method of claim 1, wherein each J, J' and J'", when present, is H.--.

In Claim 40 at Column 105, ";;" should appear as --;--.

In Claim 40 at Column 108, following the fourth structure, "." should appear as --;--.

In Claim 42 at Column 110, Lines 15-25, " 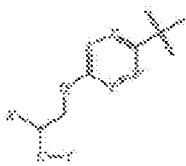 is h or a moiety selected from:" should appear as --is h or a moiety selected from--.

Signed and Sealed this
Nineteenth Day of June, 2018

Andrei Iancu
*Director of the United States Patent and Trademark Office*